US008802390B2

(12) United States Patent
Bertin et al.

(10) Patent No.: US 8,802,390 B2
(45) Date of Patent: *Aug. 12, 2014

(54) ELECTROCHEMICAL ASSAY FOR THE DETECTION OF ENZYMES

(75) Inventors: Paul A. Bertin, Chicago, IL (US); Michael Ahrens, Evanston, IL (US); Dimitra Georganopoulou, Chicago, IL (US); Harry B. Gray, Pasadena, CA (US); Thomas J. Meade, Evanston, IL (US); Markus Franz Wunder, Evanston, IL (US)

(73) Assignee: OHMX Corporation, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/353,001

(22) Filed: Jan. 18, 2012

(65) Prior Publication Data

US 2012/0156709 A1 Jun. 21, 2012

Related U.S. Application Data

(62) Division of application No. 12/253,828, filed on Oct. 17, 2008, now abandoned.

(60) Provisional application No. 60/980,733, filed on Oct. 17, 2007, provisional application No. 61/087,094, filed on Aug. 7, 2008, provisional application No. 61/087,102, filed on Aug. 7, 2008.

(51) Int. Cl.
*C12Q 1/37* (2006.01)

(52) U.S. Cl.
USPC .................................. 435/23; 435/4

(58) Field of Classification Search
CPC ....................................................... C12Q 1/37
USPC ....................................................... 435/4, 23
See application file for complete search history.

(56) References Cited

U.S. PATENT DOCUMENTS

| | | | |
|---|---|---|---|
| 4,304,853 A | 12/1981 | Jozefonvicz et al. |
| 5,834,224 A | 11/1998 | Ruger et al. |
| 6,013,170 A | 1/2000 | Meade |
| 6,013,459 A | 1/2000 | Meade |
| 6,248,229 B1 | 6/2001 | Meade |
| 6,348,319 B1 | 2/2002 | Braach-Maksvytis et al. |
| 6,432,723 B1 | 8/2002 | Plaxco et al. |
| 6,495,336 B1 | 12/2002 | Ludin et al. |
| 6,676,816 B2 | 1/2004 | Mao et al. |
| 6,750,016 B2 | 6/2004 | Mirkin et al. |
| 6,770,190 B1 | 8/2004 | Milanovski et al. |
| 6,927,039 B2 | 8/2005 | Gilardi et al. |
| 6,932,894 B2 | 8/2005 | Mao et al. |
| 6,991,926 B2 | 1/2006 | Schmid et al. |
| 7,018,523 B2 | 3/2006 | Meade |
| 7,267,939 B2 | 9/2007 | Meade |
| 7,384,749 B2 | 6/2008 | Kayyem et al. |
| 7,560,237 B2 | 7/2009 | O'Connor et al. |
| 7,732,140 B2 | 6/2010 | Vandenbark et al. |
| 7,759,114 B2 | 7/2010 | Martin et al. |
| 7,803,572 B2 | 9/2010 | Braven et al. |
| 7,807,835 B2 | 10/2010 | Xie et al. |
| 2005/0123948 A1 | 6/2005 | Claycomb et al. |
| 2005/0136394 A1 | 6/2005 | Fang et al. |
| 2006/0003382 A1 | 1/2006 | Eckermann et al. |
| 2008/0164154 A1 | 7/2008 | Purvis |
| 2008/0248592 A1 | 10/2008 | Bamdad |
| 2010/0204554 A1 | 8/2010 | Say et al. |

FOREIGN PATENT DOCUMENTS

| | | |
|---|---|---|
| EP | 02075339 | 7/2009 |
| WO | WO 97/21431 | 6/1997 |
| WO | WO 98/57158 | 12/1998 |
| WO | WO 98/57159 | 12/1998 |
| WO | 03/019171 | 3/2003 |
| WO | 2008/045799 | 4/2008 |
| WO | 2010/142037 | 12/2010 |
| WO | 2011/041586 | 4/2011 |

OTHER PUBLICATIONS

Kitano et al. "Self-Assembled monolayer of a pepstatin fragment as a sensing element for aspartyl proteases", Anal. Chem. 2005, 77:1588-1595.*
U.S. Appl. No. 60/980,733, filed Oct. 17, 2007, Georganopoulou.
Ahn-Yoon et al., "Ganglioside-liposome immunoassay for the detection of botulinum toxin," *Anal. Bioanat Chem.* 378:68-75 (2004).
Aleksey, et al., "Nanoscale 1,3,5,7-Tetrasubstituted Adamantanes and *p*-Substituted Tetraphenyl-methanes for AFM Applications," *Organic Letters* 4(21):3631-3634 (2002).
Alston et al., "Cyclodextrins as Second Sphere Ligands for Transition Metal Complexes—the X-Ray Crystal Structure of [Rh(cod)(NH$_3$)$_2$ β-cyclodextrin][PF$_6$]·6H$_2$O," *Angew. Chem. Int. Ed. Engl.* 24(9):786-787 (1985).
Amorim et al., "Nuclear Magnetic Resonance Studies of the ProtonationSequence of Some Oxaaza Macrocyclic Compounds," *J. Chem. Soc. Dalton Trans.* 3449-3455 (1990).
Ando, et al., "The effect of second-sphere coordination-II. Adduct formation between [RU(NH$_3$)5L](PF$_6$)$_n$ (n=2 and 3) and 18-crown-6 ether in solution and the effect on redox behaviour," *Polyhedron* 11(18):2335-2340 (1992).
Ando et al., "Effect of Second-Sphere Coordination. 4. Factors Influencing the Electrochemical Behavior of Ruthenium—Ammine Complexes Cause by Second-Sphere Coordination of Crown Ethers," *Inorg. Chem.* 35:3504-3508 (1996).
Ando et al.,"The Effect of Second-Sphere Coordination. 7. Isolation of 18-Crown-6 Ether Adducts of Ruthenium—Ammine Complexes," *Inorg. Chim. Acta.* 282:247-251 (1998) [bb 5001].
Ando, "Hydrogen bonding of 18-crown-6 ether to ruthenium—ammine complexes at second sphere," *Coordination Chemistry Reviews* 248:185-203 (2004).

(Continued)

*Primary Examiner* — Bin Shen
(74) *Attorney, Agent, or Firm* — Wolf, Greenfield & Sacks, P.C.

(57) ABSTRACT

The invention relates to novel compositions and methods for the detection of enzymes using the nuclear reorganization energy, λ, of an electron transfer process.

14 Claims, 15 Drawing Sheets

(56) References Cited

OTHER PUBLICATIONS

Appoh et al., "Electrochemical Investigations into the Binding of Some Nonredox Active Metal Ions to Surface-Bound Glutamic Acid Conjugates," *J. Phys. Chem.* C 111:4235-4245 (2007).
Arion et al., "Potassium—controlled synthesis of heterotopic macrocycles based on isothiosemicarbazide," *Inorg. Chim. Acta* 328:123-133 (2002).
Bottcher et al., "Spectroscopy and Electrochemistry of Cobalt(III) Schiff Base Complexes ," *Inorg. Chem.* 36:2498-2504 (1997).
Bryce, et al., "A New Route to 1,4-Disubstituted Cyclohexa-1,3-diene Derivatives: TheSythesis of a Highly Conjugated Bis(benzothiazoline) Derivative," *J. Org. Chem.* 3399-3401 (1984).
Callahan, et al., "Effects of Weak Metal-Metal Interactions in Ligand-Bridged Complexes of Ruthenium. Dimeric Complexes Containing Ruthenium Ions in Different Coordination Environments," *Inorg. Chem.* 14(7):1443-1453 (1975).
Chidsey et al., "Coadsorption of Ferrocene-Terminatd and Unsubstituted Alkanethiols on Gold: Electroactive Self-Assembled Monolayers," *J. Am. chem. Soc.* 112:4301-4306 (1990).
Clements and Rice, "Some 3,9-Dicarboxylic Acids of 2,4,8,10-Tetroxaspirol[5.5]undecane," *J. Org. Chem.* 24:1958-1961 (1959).
Creutz and Taube, "Binuclear Complexes of Ruthenium Ammines," *J. Am. Chem. Soc.* 95:1086-1094 (1973).
Curtis, et al., "Directed, Intramolecular Electron Transfer in Mixed-Valence Dimers," *Inorg. Chem.* 24:385-397 (1985).
Dong, et al., "Perturbation of the electronic structure of the Creutz-Taube ion via asymmetric encapsulation with macrocyclic ether species," *J. Am. Chem. Soc.* 115:4379-4380 (1993).
Eckermann, et al., "Syntheses of Ru—S Clusters with Kinetically Labile Ligands via the Photolysis of [(cymene)$_3$Ru$_3$S$_2$](PF$_6$)$_2$," *Inorg. Chem.* 40:1459-1465 (2001).
Eskelinen, et al., "The synthesis and electrochemical behavior of ruthenium(III) bipyridine complexes: [Ru(dcbpy)Cl$_4$] (dcbpy=4,4'-dicarboxylic acid-2,2'-bipyridine) and [Ru(bpy)CI$_3$L] (L=CH$_3$OH, PPh$_3$, 4,4'-bpy, CH$_3$CN)," *Journal of Electroanalytical Chemistry* 579:257-265 (2005).
Fu et al., "Terminal Ligand Influence on the Electronic Structure and Intrinsic Redox Properties of the [Fe$_4$S$_4$]$^{2+}$Cubane Clusters," *Inorg. Chem* 43(12):3647-3655 (2004).
Furholz et al., "The Creutz-Taube Complex Revisited," *J. Am. Chem. Soc.* 106:121-123 (1984).
Gebbink, et al., "Fe$_4$S$_4$ Clusters Functionalized with Molecular Receptor Ligands," *Eur. J. Inor. Chem.* 2087-2099 (2000).
Gerhardt and Weck, "Investigations of Metal-Coordinated Peptides as Supramolecular Synthons," *J. Org. Chem.* 71:6333-6341 (2006).
Gianneschi et al., "Signal Amplification and Detection via a Supramolecular Allosteric Catalyst," *J. Am. Chem. Soc.* 127:1644-1645 (2005).
Grancharov, et al., "Individually addressable recessed gold microelectrode arrays with monolayers of thio-cyclodextrin nanocavities," *Analyst* 130:1351-1357(2005).
Gray and Winkler, "Electron Transfer in Proteins," *Ann. Rev. Biochem.* 65:537 561(1996).
Hallis et al., "Development of Novel Assays for Botulinum Type A and B Neurotoxins Based on Their Endopeptidase Activities," *J. Clin. Microbial.* 34:1934-1938 (1996).
Heinze and Schlenker., "Main Chain Ferrocenyl Amides from 1-aminoferrocene-1'-carboxylic Acid," *Eur. J. Inorg. Chem.* 2974-2988 (2004).
Heinze and Schlenker, "Anion-Induced Motion in a Ferrocene Diamide," *Eur. J. Inorg. Chem.* 66-71 (2005).
Holleman and Wiberg, "Inorganic Chemistry," *Academic Press* 1616-1627 (2001).
Illingworth, "Phosphofructokinase regulation," School of Biochemistry and Microbiology, University of Leeds, BIOC2120 Lectures 2007 (Aug. 5, 2007), p. 4-6.
Isied and Taube, "Effects of SO$_2$ , HSO$_3$ , and SO$_3$$^{2-}$ as Auxiliary Ligands on the Reactivity of Ammineruthenium(II)-Ligand Bonds," *Inorg. Chem.* 13(7):1545-1551 (1974).

Isied and Taube, "Rates of Intermolecular Electron Transfer," *J. Am. Chem. Soc.* 95(24):8198-8200 (1973).
Isied and Kuehn, "Peptide Formation in the Presence of a Metal Ion Protecting Group. Pentaamine Cobalt(III)-Peptide Complexes," *J. Am. Chem. Soc.* 100(21):6752-6754 (1978).
Jeffrey and Rauchfuss, "Metal Complexes of Hemilabile Ligands. Reactivity and Structure of Dichlorobi(o-(diphenylphosphino)anisole)ruthenium(II)," *Inorg. Chem.* 18(10):2658-2666 (1979).
Jwo, et al., "Intramolecular Electron Transfer from Pentacyanoferrate(II) to Pentaamminecobalt(III) Mediated by Various 4,4'-Bipyridines," *J. Am. Chem. Soc.* 101:6189-5197 (1979).
Kanatzidis et al., "A New Iron-Sulphide Cluster Containing the 'Prismane' (Fe6(mu-S6]3+ Core. Synthesis, Structure, and Properties of [Et4N]3[FeS6Cl6]," *J. Chem.Soc., Chem. Commun.* 356-358 (1984).
Karyakin, "Prussian Blue and its analogues: electrochemistry and analytical applications," *Electroanalysis,* 13(10):813-819 (2001).
Kothari and Busch, "Cobalt(III) Complexes of Cysteine and Cysteine Derivatives," *Inorg. Chem.* 8:2276-2280 (1969).
Kerman and Kraatz, "Electrochemical detection of kinase-catalyzed thiophosphorylation using gold nanoparticles," *Chem. Commun.* 5019-5021 (2007).
Kerman et al., "An electrochemical approach for the detection of HIV-1 protease," *Chem. Commun.* 3829-3831 (2007).
Khan et al., "Surface Studies of Aminoferrocene Derivatives on Gold: Electrochemical Sensors for Chemical Warfare Agents," *Anal. Chem.* 79(7):2877-2884 (2007).
Lavallee and Fleischer, "Charge Delocalization in Pentaammineruthenium(II)Complexes. I. Spectral Properties, Basicities, and ChargeDensities by Nuclear Magnetic Resonance Spectroscopy," *J. am. Chem. Soc.* 94(8):2583-2599 (1972).
Liu et al., "Protein modulation of electrochemical signals: application to immunobiosensing," *Chem.Commun.* 3670-3872 (2008).
Louie, et al., "A cobalt complex that selectively disrupts the structure and function of zinc fingers," *Proc. Natl. Acad. Sci. USA* 95: 6663-6668 (1998).
Lowe and Garner, "Transition-metal Complexes of Crown Ether Benzodithiolenes. Part 2. The Effects of Alkali-metal Cation Binding," *J. Chem. Soc. Dalton Trans.* 3333-3340 (1993).
Luo and Isied, "Ruthenium Tetraammine Chemistry of Self-Assembled Monolayers on Gold Surfaces: Substitution and Reactivity at the Monolayer Interface," *Langmuir* 14:3602-3606 (1998).
Mahmoud and Kraatz, "A Bioorganometallic Approach for the Electrochemical Detection of Proteins:A Study on the Interaction of Ferrocene-Peptide Conjugates with Papin in Solution and on Au Surfaces," *Chem. Eur. J.* 13:5885-5895 (2007).
Maeda, et al., "Synthesis of Bis[aminomethyl]crown Ethers," *Synthesis Communications* 185-187 (1983).
Masar, et al., "Fine-Tuning the Weak-Link Approach: Effect of Ligand Electron Density on the Formation of Thodium(I) and Iridium(I) Metallomacrocycles," *Inorg. Chem.* 42(21):6851-6858 (2003).
Moscherosch et al., "Tetranuclear Pentaammineruthenium Complexes Bridged by TT-Conjugated Tetracyano Ligands Related to TCNE; Syntheses and Spectroscopy of Different Oxidation States," *Inorg. Chem.* 34:4326-4335 (1995).
Moutet, et al., "Heterodinucleating macrocyclic compounds designed for electrochemical recognition," *Electrochimica Acta* 46:2733-2740 (2001).
Neyhart et al., "Solvent-Induced Electron Transfer and Delocalization in Mixed-Valence Complexes. Electrochemistry, " *J. Am. Chem. Soc.* 118:3724-29 (1996).
Nguyen et al., "An Affinity-Based Method for the Purification of Fluorescently-Labeled Biomolecues," *Bioconjugate Chem.* 17:869-872 (2006).
Orlowski, et al., "Electrodeposition of ferrocenoyl peptide disulfides," *Chem. Commun.,* 1330-1332 (2005).
Orlowski, et al., "Reorganization Energies of Ferrocene-Peptide Monolayers," *Langmuir* 23:12765-12770 (2007).
Peruski et al., "Rapid and sensitive detection of biological warfare agents using time-resolved fluorescence assays," *J. Immunol Methods* 263:35-41 (2002).

(56) References Cited

OTHER PUBLICATIONS

Plumb and Kratz, "Interaction of a Ferrocenoyl-Modified Peptide with Papin:Toward Protein-Sensitive Electrochemical Probes," *Bioconjugate Chem.* 14:601-606 (2003).

Rawls, "Optimistic About Antisense," *C& En* 35-39 (1997).

Ricci and Palleschi, "Sensor and biosensor preparation, optimisation and applications of Prussian Blue modified electrodes," *Biosensors & Bioelectronics* 21(3):389-407 (2005).

Richardson et al., Preparation and Properties of Mixed-Valence (mu-Dinitrogen)bis(pentaamine) Complexes of Osmium and Ruthenium,RAWLS, C & E News p. 35, Jun. 2, 1997 *Inorg. Chem.* 21:3136-3140 (1982).

Richardson and Taube, "Electronic Interactions in Mixed-Valence Molecules as Mediated by Organic Bridging Groups," *J. Am. Chem. Soc.* 105:40-51 (1983) (bb 5001).

Rosa and Coucouvanis, "Crown-Ether-Functionalized Nickel Salicylaldimine Complexes. Structural Characterization of Their Potassium, Cesium, and Hexylammonium Derivatives andTheir Use in the Transport of Amino Acids," *Inorg. Chem.* 37:2328-2329 (1998).

Schiavo et al., "Identification of the Nerve Terminal Targets of Botulinum Neurotoxin Serotypes A,D, and E,"*JBS* 268(32):23784-23787 (1993).

Schiavo et al., "Botulinum neurotoxins seotypes A and E cleave SNAP-25 at distance COOH-terminal peptide bonds," *FEBS Letters* 335(1):99-103 (1993).

Schmidt et al., "Fluorigenic Substrates for the Protease Activities of Botulinum Neuroxtoxins, Serotypes A, B, and F," *Appl. Environ. Microbiol.* 69(1):297-303 (2003).

Shults and Imperiali, "Versatile Fluorescence Probes of Protein Kinase Activity," *J. Am. Chem. Soc.* 125:14248-14249 (2003).

Scott and Nolan, "Stabilization of Organometallic Species Achieved by the Use of N—Heterocyclic Carbene (NHC) Ligands," *Eur. J. Inorg. Chem* 1815:1828 (2005).

Seidel, et al., "Coordination chemistry of N-Alkylbenzamide-2,3-dithiolates as an Approach to Poly(dithiolate) Ligands: 1,4-Bis[(2,3-dimercaptobenzamido)methyl]benzene and Its Chelate Complex with the $(C_5H_5)$Ti Fragment," *Inorg. Chem.* 37:6587-6596 (1998).

Shone, et al., "Proteolytic cleavage of synthetic fragments of vesicle-associated membgrane protein, isoform-2 by botulinum type B neurotoxin," *Eur. J. Biochem* 217:965-972 (1993).

Silverman et al., "Multivalent avimer proteins evolved by exon shuffling of a family of human receptor domains," *Nature Biotechnology* 23:1556-1561 (2005).

Sizova, et al., "Substituents effect on the electronic structure, spectra and photochemistry of $[Ru(NH_3)_5(PY-X)]^{2+\ complexes,"}$ *Inorg. Chim. Acta* 357:354-360 (2004).

Song et al., "Electrochemical detection of kinase-catalyzed phosphorylation using ferrocene-conjugated ATP," *Chem. Commun.* 502-504 (2008).

Sprinzl et al., "Enzymatic Incorporation of ATP and CTP Analogues into the 3' End of tRNA," Eur. J. Biochem. 81:579 (1977).

Stodt et al., "Preparation, Reactivity and Peptide Labelling Properties of $(\eta^6$-Arene)ruthenium(II) Complexes with Pendant Carboxylate Groups," *Euro. J. Inorg. Chem.* 1873-1882 (2003).

Sutton and Taube, Metal to Metal Interactions in Weakly Coupled Mixed-Valence Complexes Based on Ruthenium Ammines, *Inorg. Chem.* 20(10):3125-3134 (1981).

Sutton et al., "Determination of the Comporportionation Constant for a Weakly Coupled Mixed-Valence System by Titration of the Intervalence Treansfer Band: μ-4,4'-Bipyridyl)-bis(pentaam-mineruthenium)(5+)," *Inorg. Chem.* 18(4):1017-1021 (1979).

Syamal et al., "Syntheses and characterization of a chelatingresin containing ONNO donor quadridentate Schiff base and its coordination complexes with copper(II), nickel(II), cobalt(II), iron(III), zinc(II), cadmium(II), molybdenum(VI) and uranium(VI)$^{1,2}$," *Reactive and Functional Polymers* 39:27-35 (1999).

Therrien and Suss-Fink, "New mono and dinuclear arene ruthenium chloro complexes containing ester substituents," *Inorganica Chimica Acta* 359:4350-4354 (2006).

Tom et al., Mixed Valence Complexes of Ruthenium Ammines with 4,4'-Bipyridine as Bridging Ligand, *J. Am. Chem. Soc.* 96(25):7827-7829 (1974).

Volkers, et al., "Coordination Chemistry of 3-Mercapto-2-(Mercaptomethyl)propanoic Acid (Dihydroasparagusic Acid) with Iron and Nickel," *Eur. J. Inorg. Chem.* 4793-4799 (2006).

Wang, et al., "tmtacn,tacn, and Triammine Complexes of $(\eta^6$-arene)Ox$^{II}$: Syntheses, Characterizations, and Photosubstitution Reactions (tmtacn=1,4,7-Trimethyl-1,4,7- triazacyclononane; tacn=1,4,7-Triazacyclononane)," *Inorg. Chem.* 40:593-600 (2001).

Wei, et al., "Diverse Redox-Active Molecules Bearing Identical Thiol-Terminated ripodal Tethers for Studies of Molecular Information Storage," *J. Org. Chem.* 69:1461-1469 (2004).

Adjémian, et al., "Cleavage-Sensing Redox Peptide Monolayers for the Rapid Measurement of the Proteolytic Activity of Trypsin and α-Thrombin Enzymes," *Langmuir* 26(12):10347-10356 (2010).

Ekeroth et al., "Electrochemical Evaluation of the Interfacial Capacitance Upon Phosphorylation of Amino Acid Analogue Molecular Films," Anal. Chem. 2001, 73:4463-4468.

Houseman et al., "Maleimide-Functionalized Self-Assembled Monolayers for the Preparation of Peptide and Carbohydrate Biochips," Langmuir, 2003, 19:1522-1531.

Liu, et al., "Electrochemical Proteolytic Beacon for Detection of Matrix Metalloproteinase Activities," *J. Am. Chem. Soc.* 128:12382-12383 (2006).

Meyerhoff et al. "Novel Nonseparation Sandwich-Type Electrochemical Enzyme Immunoassay System for Detecting Marker Proteins in Undiluted Blood," Clin. Chem., 1995 41(9):1378-1384.

Spinke, J., et al., "Molecular Recognition at selfassembled monolayers: Optimization of surface functionalization," The Journal of Chemical Physics, vol. 99, No. 9, Nov. 1993, pp. 7012-7018.

Spinke, J., et al., "Molecular Recognition at self-assembled monolayers: The construction of multicomponent multilayers," Langmuir, 1993, pp. 1821-1825.

Adjemian, Jocelyne, et al., "Cleavage-Sensing Redox Peptide Monolayers for the Rapid Measurement of the Proteolytic Activity of Trypsin and a-Thrombin Enzymes," Langumuir Article, Jan. 27, 2010, pp. 1-10.

Chin, Curtis D., et al, "Microfluidics-Based Diagnostics of Infectious Diseases in the Developing World," Nature Medicine, Technical Reports, available online Jul. 31, 2011, pp. 1-6.

Gaster, Richard S., et al., "nanoLAB: An Ultraportable, Handheld Diagnostic Laboratory for Global Health," Lab on a Chip, Dynamic Article Links, Jan. 24, 2011, pp. 1-7.

Houseman, Benjamin T., et al., "Peptide Chips for the Quantitative Evaluation of Protein Kinase Activity," Nature Biotechnology, Research Article, Mar. 2002, vol. 20, pp. 270-274.

Kerman, Kagan, et al., "Electrochemical Detection of Kinase-Catalyzed Thiophosphorylation Using Gold Nanoparticles," Chem. Commun. 2007, pp. 5019-5021.

Kerman, Kagan, et al., "Peptide Biosensors for the Electrochemical Measurement of Protein Kinase Activity," Anal. Chem., 2008, vol. 80, pp. 9395-9401.

Kerman, Kagan, et al., "Electrochemical Detection of Protein Tyrosine Kinase-Catalysed Phosphorylation Using Gold Nanoparticles," Biosensors and Bioelectronics, 2009, vol. 24, pp. 1484-1489.

Kim, S.D., et al., "Gold-Film Array-Electrode for Electrochemical ELISA," Sensors and Actuators B, 2005, pp. 463-469.

Labib, Mahmoud, et al., "A Bioorganometallic Approach for Rapid Electrochemical Analysis of Human Immunodeficiency Virus Type-1 Reverse Transcriptase in Serum," Elsevier, Article in Press, Elecrochimica Acta, available online Mar. 22, 2011, pp. 1-7.

Leinonen, J., et al., "Development of Novel Peptide Ligands Modulating the Enzyme Activity of Prostate-Specific Antigen," Scand. J. Clin. Lab. Invest, 2000, pp. 59-64.

Li, Peng, et al., "Development of an Ultrafast Quantitative Heterogeneous Immunoassay on Prefunctionalized Poly (Dimethylsiloxane), Microfluidic Chips for the Next-Generation Immunosensors," Microfluidics and Nanofluidics, vol. 7, No. 4, Mar. 11, 2009.

(56) References Cited

OTHER PUBLICATIONS

Martic, Sanela, et al., "Probing the Role of the Linker in Ferrocene-ATP Conjugates: Monitoring Protein Kinase Catalyzed Phosphorylations Electrochemically," Chemistry a European Journal, 2011, vol. 17, pp. 6744-6752.

Martic, Sanela, et al., "Use of 5-y-Ferrocenyl Adenosine Triphosphate (Fc-ATP) Bioconjugates Having Poly(ethylene glycol) Spacers in Kinase-Catalyzed Phosphorylations," Bioconjugate Chemistry, 2011, pp. 1-10.

Martic, Sanela, et al., "Enzymatically Modified Peptide Surfaces: Towards General Electrochemical Sensor Platform for Protein Kinase Catalyzed Phosphorylations," Analyst, 2011, 136, pp. 107-112.

Nagy, Geza, et al., "Screen-Printed Amperometric Microcell for Proline lminopepfidase Enzyme Activity Assay," Biosensors & Bioelectronics, 2000, vol. 15, pp. 265-272.

Song, Haifeng, et al., "Electrochemical Detection of Kinase-Catalyzed Phosphorylation Using Ferrocene-Conjugated ATP," Chem. Commun., 2008, pp. 502-504.

Vukmirovic-Popovic, Snezana, et al., "Presence and Enzymatic Activity of Prostate-Specific Antigen in Archival Prostate Cancer Samples," Oncology Reports, 2008, vol. 20, pp. 897-903.

Zhou, Ya-Min, et al., "An Amperometric Immunosensor Based on an Electrochemically Pretreated Carbon-Paraffin Electrode for Complement III (C3) Assay," Biosensors and Bioelectronics, 2008, vol. 18, pp. 473-481.

\* cited by examiner

ELECTROCHEMICAL ASSAY FOR THE DETECTION OF ENZYMES

CROSS REFERENCE TO RELATED APPLICATIONS

This application is a Divisional application of U.S. patent application Ser. No. 12/253,828, filed Oct. 17, 2008, which claims the benefit of, and priority to, U.S. Provisional Patent Application Ser. Nos. 60/980,733, filed on Oct. 17, 2007, and 61/087,094 and 61/087,102, filed on Aug. 7, 2008, the entire disclosures of which are hereby incorporated by reference in their entireties.

FIELD OF THE INVENTION

The invention relates to novel compositions and methods for the detection of enzymes using change in $E^0$ of a transitional metal complex.

BACKGROUND OF THE INVENTION

Electron transfer reactions are crucial steps in a wide variety of biological transformations ranging from photosynthesis or aerobic respiration. Studies of electron transfer reactions in both chemical and biological systems have led to the development of a large body of knowledge and a strong theoretical base, which describes the rate of electron transfer in terms of a small number of parameters.

Electronic tunneling in proteins and other biological molecules occurs in reactions where the electronic interaction of the redox centers is relatively weak. Semiclassical theory reaction predicts that the reaction rate for electron transfer depends on the driving force ($-\Delta G°$), a nuclear reorganization parameter ($\lambda$), and the electronic-coupling strength between the reactants and products at the transition state ($H_{AB}$), according to the following equation:

$$k_{ET} = (4\pi^3/h^2 \lambda k_B T)^{1/2} (H_{AB})^2 \exp[(-\Delta G°+\lambda)2/\lambda k_B T]$$

The nuclear reorganization energy, $\lambda$, in the equation above is defined as the energy of the reactants at the equilibrium nuclear configuration of the products. For electron transfer reactions in polar solvents, the dominant contribution to $\lambda$ arises from the reorientation of solvent molecules in response to the change in charge distribution of the reactants. The second component of $\lambda$ comes from the changes in bond lengths and angles due to changes in the oxidation state of the donors and acceptors.

Previous work describes using change in reorganization energy, $\lambda$, as the basis of novel sensor. See for example, U.S. Pat. Nos. 6,013,459, 6,013,170, 6,248,229, and 7,267,939, all herein incorporated by reference in their entirety. The methods generally comprise binding an analyte to or near a redox active complex. The redox active complex comprises at least one solvent accessible redox active molecule and a capture ligand which will bind the target analyte, and the complex is bound to an electrode. Upon analyte binding, the reorganization energy of the redox active molecule decreases to form a solvent inhibited redox active molecule, to allow electron transfer between the solvent inhibited redox active molecule and the electrode.

It is an object of the present invention to provide composition and methods for the detection of target analytes using alteration in the solvent reorganization energy, corresponding to changes in the $E^0$ of redox active molecules.

SUMMARY OF THE INVENTION

The present invention to provide composition and methods for the detection of target analytes using the solvent reorganization energy, the corresponding in $E^0$ of redox active molecules.

In one aspect, the present invention provides a method for detecting a protease in a test sample, said method comprising: (a) adding a test sample comprising a protease to an electrode, said electrode comprises: (i) a self-assembled monolayer (SAM); (ii) a covalently attached eletroactive active moiety (EAM) comprising a transition metal complex with an $E^0$; and (iii) a plurality of proteins attached to said electrode, wherein said proteins comprises a cleavage site of said protease; (b) cleaving a plurality of said proteins with said protease; and (c) determining the presence of said protease by measuring a change of said $E^0$.

In some embodiments, the EAM and the proteins are arranged so that the EAM is at least partially shielded by the proteins from exposing to a solution. In some embodiments, said cleavage site is near the height of said EAM such as when said protein is cleaved at said cleavage site, said EAM is exposed to said solution. In some embodiments, the protease is endopeptidase toxin, such as is an endopeptidase nuerotoxin produced by the bacterium *Clostridium botulinum*, including botulinum toxin A, B, or E.

In some embodiments, the EAM and said proteins are attached separately to said electrode. In some embodiments, the protein comprises a sequence according to any of SEQ ID NO: 1-4.

In some embodiments, said transition metal complex does not comprise a metal selected from the group consisting of: manganese, technetium, rhenium, iron, ruthenium, osmium, cobalt, rhodium, iridium, nickel, palladium, platinum, copper, silver and gold. In some embodiments, said transition metal complex does not comprise a ferrocene.

In another aspect the present invention provides a method for detecting a kinase in a test sample, said method comprising the steps of: (a) adding a test sample comprises a kinase to an electrode comprising: (i) a self-assembled monolayer (SAM); (ii) a covalently attached eletroactive active moiety (EAM) comprising a transition metal complex with an $E^0$; and (iii) a plurality of proteins attached to said electrode, wherein said proteins are first substrates of said kinase; (b) phosphorylating said proteins with said kinase and a second kinase substrate so that said second kinase substrate is covalently attached to said protein; and (c) determining the presence of said kinase by measuring a change of said $E^0$.

In some embodiments, said EAM and said peptides are arranged so that the EAM is at least partially exposed to a solution.

In some embodiments, said first substrate comprises a phosphorylation site which site is near the height of said EAM such that when said in the mixed SAM arrangement, wherein said cleavage site is near the height of said EAM such as such that when the second substrate is attached to the first substrate through said phosphorylating step, said second substrate-coupled first substrate will shield the neighboring EAMs from said solution. The kinase is a protein kinase selected from the group consisting of the kinases listed in Table 2. In some embodiments, the second kinase substrate is a polymer-modified ATP cofactor.

In some embodiments, said transition metal complex does not comprise a metal selected from the group consisting of: manganese, technetium, rhenium, iron, ruthenium, osmium, cobalt, rhodium, iridium, nickel, palladium, platinum, copper, silver and gold. In some embodiments, said transition metal complex does not comprise a ferrocene.

In another aspect, the present invention provides a method for detecting a target enzyme in a test sample, said method comprising: (a) adding a test sample comprises a target enzyme to an electrode comprising: (i) a self-assembled monolayer (SAM); (ii) a covalently attached eletroactive active moiety (EAM) comprising a transition metal complex with an $E^0$; and (iii) a plurality of substrates attached to said electrode, wherein said substrates are substrates of said enzyme; (b) contacting said target enzyme and said substrates to form a plurality of reactants; and (c) determining the presence of said enzyme by measuring a change of said $E^0$.

In some embodiments, said transition metal complex comprises a metal selected from the group consisting of manganese, technetium, rhenium, iron, ruthenium, osmium, cobalt, rhodium, iridium, nickel, palladium, platinum, copper, silver, and gold. In some embodiments, the target enzyme is a hydrolase, preferably is a protease, including peptidase. In some embodiments, the target enzyme is a transferase, preferably a kinase.

BRIEF DESCRIPTION OF THE DRAWINGS

FIG. 3A depicts the situation where a linker is attached at one end to the electrode and the other end terminates in a ligand (L) that provides a coordination atom for the transition metal (TM). The capture substrate (CS) provides an additional ligand (not depicted), and a plurality of other ligands provide the remaining coordination atoms. Upon action by the enzyme, the capture substrate results in a leaving group (X). It should be noted that FIG. 3 depicts a situation where the transition metal utilizes 6 coordination atoms, but other numbers of coordination atoms can be used, depending on the metal. Similarly, FIG. 3 depicts the use of ligands that provide a single coordination atom, but fewer ligands providing multiple coordination atoms (e.g. multidentate) ligands can be used as well. FIG. 3B depicts the situation where the capture substrate and the EAM are attached separately to the electrode. FIG. 3C depicts a similar situation to FIG. 3A, except the capture substrate does not provide a coordination atom to the transition metal. It should be appreciated that solution phase systems can be similar to FIGS. 3A and 3C, in that the electrochemical potential of the EAM in solution can be altered as a result of the enzymatic activity of the target enzyme.

DETAILED DESCRIPTION OF THE INVENTION

Figure 1:
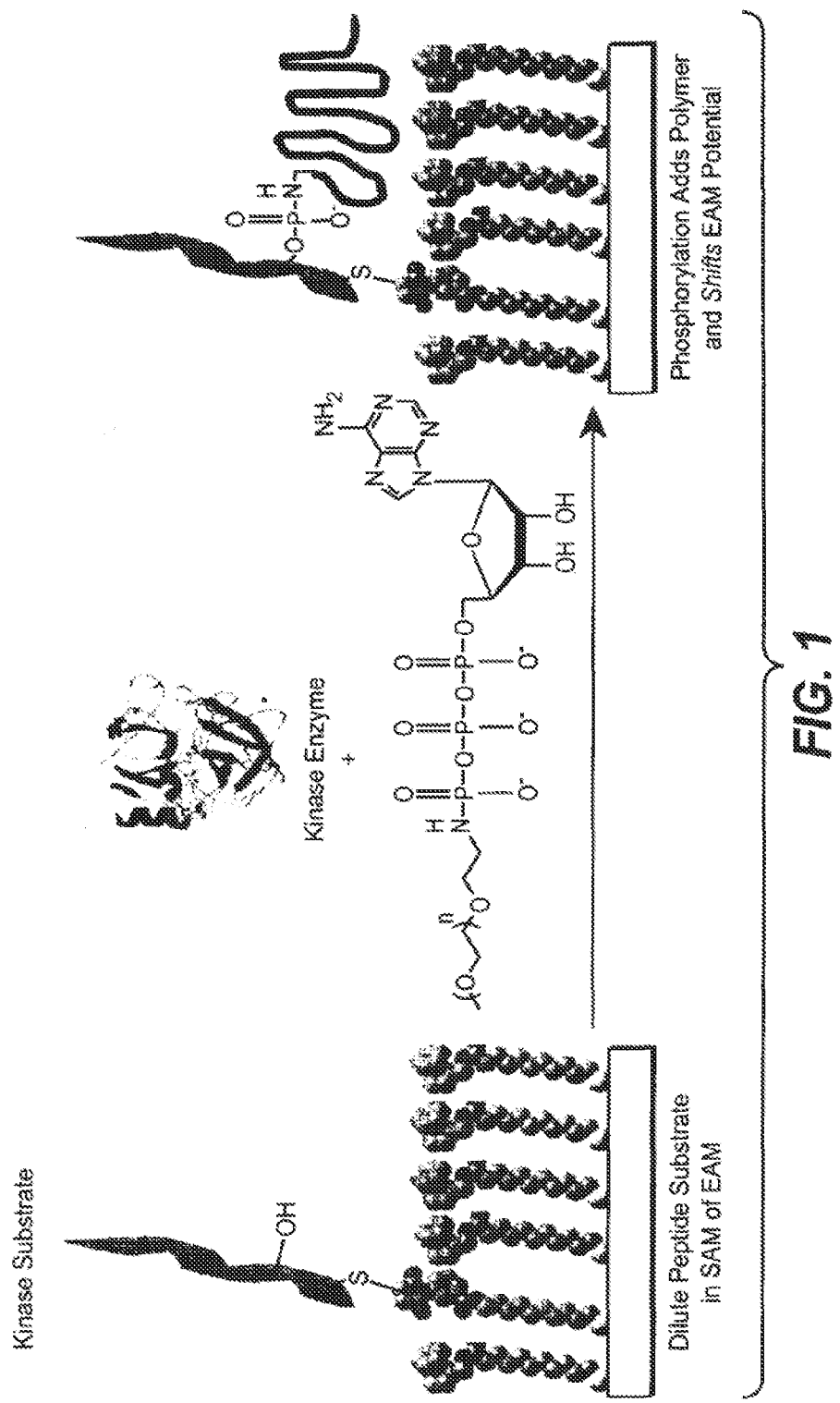
FIG. 1 depicts schematically the electrochemical assay for kinase activity according to some embodiments of the present invention.

The present invention is directed to methods and compositions for detection of analytes, particularly enzymes, based on a change of electrochemical potential, $E^0$, of a redox active molecule either on the surface of an electrode, or in some cases, in solution (while most of the description herein is directed to solid phase assays, as will be appreciated by those in the art, the invention can be used in solution as well, and such description herein is meant to apply as applicable to solution phase assays as well).

The present invention provides methods and compositions for the detection of target analytes using changes in the reorganization energy of redox active molecules upon binding of the analytes, to facilitate or hinder electron transfer between the redox active molecule and an electrode. This invention is based on the fact that when a redox active molecule, such as a transition metal ion, is either oxidized (losing an electron) or reduced (gaining an electron), changes occur in the molecular structure as well as in its immediate solvent environment. These changes in the molecules structure (bond lengths and angles) and in the organization of the solvent molecules surrounding the molecule serve to stabilize the new oxidation state energetically. The sum of these changes constitute the reorganization energy, $\lambda$, of a redox reaction. The intramolecular changes are termed the inner-sphere reorganization energy, $\lambda i$, and the changes in the solvent and environment are termed the outer-sphere or solvent reorganization energy, $\lambda o$.

For the purposes of this invention, the primary focus is on changes in the solvent reorganization energy although changes in the inner-sphere reorganization will also be considered in several embodiments of the invention. It is the intent of this invention to capitalize on changes in reorganization energy of a redox reaction when an electroactive molecule (EAM) is attached to a capture ligand (CL) which can selectively bind to an analyte of interest (e.g., protein or bacteria). Binding of the EAM-CL to the analyte results in a change in the solvent environment of the EAM so that the reorganization energy for a redox reaction involving the EAM is changed. For the case where the redox reaction involves electron transfer between an electrode and the EAM, the standard potential, $E^0$, is changed. Thus, a change in $E^0$ for an EAM-CL complex is an indication that it is bound to the analyte. It is the intent of this invention to detect the change in $E^0$ as an indicator of binding and, consequently, the presence or absence of the analyte.

In conventional methodologies for analyte detection using electron transfer usually employ the EAM as a label or tag attached to one member of a binding pair (e.g., antibody and antigen). In these methods, EAM's are chosen in which the outer sphere solvent effect is minimal, by using electroactive molecules that have minimal solvent reorganization upon oxidation or reduction. Such EAMs generally comprise large hydrophobic ligands which have little interaction with water. Thus, the ligands for the transition metal ions traditionally used are non-polar and are generally hydrophobic, frequently containing organic rings (e.g., bipyridyl and terpyridyl). Such EAMs are chosen because conventionally because the magnitude of the total electron transfer reaction is measured (current) at a predetermined electrode potential.

Without being bound by theory, it is expected that the redox molecules best suited for this invention will be those whose redox reaction has a large solvent reorganization energy in aqueous environments. Solvent reorganization to stabilize an increase or decrease in charge can be attributed to several phenomena. In polar solvents such as water, the charge on a redox molecule is stabilized by orientation of the polar solvent molecules in the environment near the redox molecule. Since polar molecules have slight charge variation on different atoms of the molecule, their orientation around the redox molecule can help to stabilize it. Further, some ligands, such as CN—, themselves are polar and have partial charges on atoms. These polar ligands can themselves induce an orientation of surrounding solvent molecules. Stabilization (or destabilization) of charged redox molecules can also occur by hydrogen bonding of solvent and/or other molecules to the ligands of the transition metal in the redox molecule. Solvent molecules, as well as other molecules in the solvent surrounding a redox molecules can be characterized and compared based on their donor number or acceptor number (Neyhart et al., J. Am. Chem. Soc 118 (1996) 3724-29, incorporated herein by reference). The use of a particular solvent or a particular additive to a solvent of a molecule having a preferred donor or acceptor number would affect the solvent reorganization energy of a redox reaction. Further, a change in the charge of a redox molecule is stabilized by charged ion in the solvent. Thus, changes in solvent reorganization change upon analyte binding can be maximized by the proper choice of an electrolyte, considering the charge on the ions, the concentration of the ions, the size of the ions, and the hydrophobicity of the ions.

Without being bound by theory, it is preferred to maximize the stabilization of the redox molecule (i.e., maximize its solvent reorganization energy) in the solvent system of choice in order that the phenomena which stabilize the redox molecule are disrupted upon binding of the redox molecule/capture ligand complex, EAM-CL to the analyte. Under such conditions, one would expect that the change in reorganization energy, evidenced by a change in $E^0$, would be optimum. It is expected that the binding of the CL to the analyte will "force" the EAM into an environment on the surface or in a cleft or pocket of the analyte (e.g., a protein) which will be less favorable to the optimal organization of the solvent environment. In one embodiment it is expected that binding would cause a shedding of water molecules near the EAM because of steric constraints.

It should be noted, and not being bound by theory, that whether the solvent reorganization energy increases or decreases upon binding (and whether $E^0$ goes to more positive or to more negative potentials is dependent upon the particular charge of the EAM. If the EAM redox reaction being monitored results in an increased charge of the EAM, such as EAM2+ oxidation to EAM3+, then the bound environment of the EAM-CL would be less stabilized by reorganization than the unbound EAM-CL. Hence, one would expect the $E^0$ to move to more positive potentials. Alternatively, if the EAM redox reaction being monitored results in a decreased charge of the EAM, such as EAM2-oxidation to EAM-, then the unbound EAM-CL would be less stabilized by reorganization than the bound EAM-CL. Hence, one would expect the $E^0$ to move to less positive potentials.

Without being bound by theory, there are two general mechanisms which may be exploited in the present invention. The first relates to inner sphere change due to the redox label. In this embodiment, the binding of a target analyte to a capture ligand which is sterically close to an EAM causes one or more of the small, polar ligands of the EAM to be replaced by one or more coordination atoms supplied by the target analyte, causing a change in the inner-sphere reorganization energy for at least two reasons. First, the exchange of a small, polar ligand for a putatively larger ligand will generally exclude more water from the metal, lowering the required solvent reorganization energy (i.e. an inner sphere $\lambda i$ effect). Secondly, the proximity of a generally large target analyte to the relatively small redox active molecule will sterically exclude water within the first or second coordination sphere of the metal ion, also changing the solvent reorganization energy.

Alternatively, the invention relies on substitutionally inert ligand, plus outer sphere effects. In this embodiment exchange of the polar ligands on the metal ion by a target analyte coordination atom. Rather, in this embodiment, the polar ligands are effectively irreversibly bound to the metal ion, and the change in solvent reorganization energy is obtained as a result of the exclusion of water in the first or second coordination sphere of the metal ion as a result of the binding of the target analyte; essentially the water is excluded (i.e. an outer sphere $\lambda o$ effect).

The present invention provides compounds with novel architecture and methods of using these compounds for detection of target analytes.

In some embodiments, the target analyte binds to the capture ligand. In some embodiments, the target analyte can be an enzyme, and the change in $E^0$ is as a result of an enzymatic event, as described in U.S. Patent Application No. 61/087,094, hereby incorporated by reference in its entirety.

In the embodiments of the invention, there is a change in the $E^0$, presumably due to a change in the reorganization energy, upon the introduction of the target analyte. As discussed more fully below, the change may be either a positive or negative shift in $E^0$, depending on a variety of factors. In general, when cyano ligands are used, the change in $E^0$ can be a negative shift in $E^0$, although depending on the system and the other ligands used (if any), the effect of interaction of the target analyte with the capture ligand can result in a positive shift in $E^0$. Surprisingly, shifts of greater than about 50 mV, 100 mV, 150 mV, 200 mV, 250 mV and 300 mV can be seen using cyano ligands.

In general, the invention is sometimes referred to as a "lawnmower" assay and can be described as follows. An electrochemical active molecule (EAM), generally comprising a transition metal and ligands that provide coordination atoms for the transition metal, is attached to the surface of an electrode, generally through a linker as described herein. In addition, the electrode may also optionally comprise a self-assembled monolayer (SAM) as described herein. In the spatial vicinity of the EAM, a capture substrate, corresponding to a substrate of the enzyme to be detected, is also attached. Upon introduction of the target enzyme, the target enzyme acts on the substrate, causing a change in the electrochemical potential of the EAM, which is then detected in a variety of ways. For example, if the enzyme is a hydrolase such as a protease, the capture substrate may be a protein such as a peptide corresponding to the target enzyme. Upon cleavage of the capture substrate, the environment around the EAM is altered, resulting in a change in the electrochemical potential of the molecule. Similarly, if the enzyme is a transferase or an isomerase, the enzymatic reaction on the substrate results in an altered environment around the EAM which again effects a change in the electrochemical potential of the molecule. The assay can also work with ligases, where a solution substrate is used, such that if the ligase is present, the solution substrate is added to the capture substrate and a change is effected.

The "lawnmower assay" describes a method for detecting enzymes that interacts with surface, optionally comprising SAMs, containing EAMs "buried" in a thick "lawn" of neighboring peptide substrates. The catalytic cleavage of synthetic peptides in the SAMs coupled with diffusion of product fragments not bound to the electrode allows for exposure of the EAMs to solvent, triggering a shift in the electrochemical potential and an increase in current.

Figure 2:
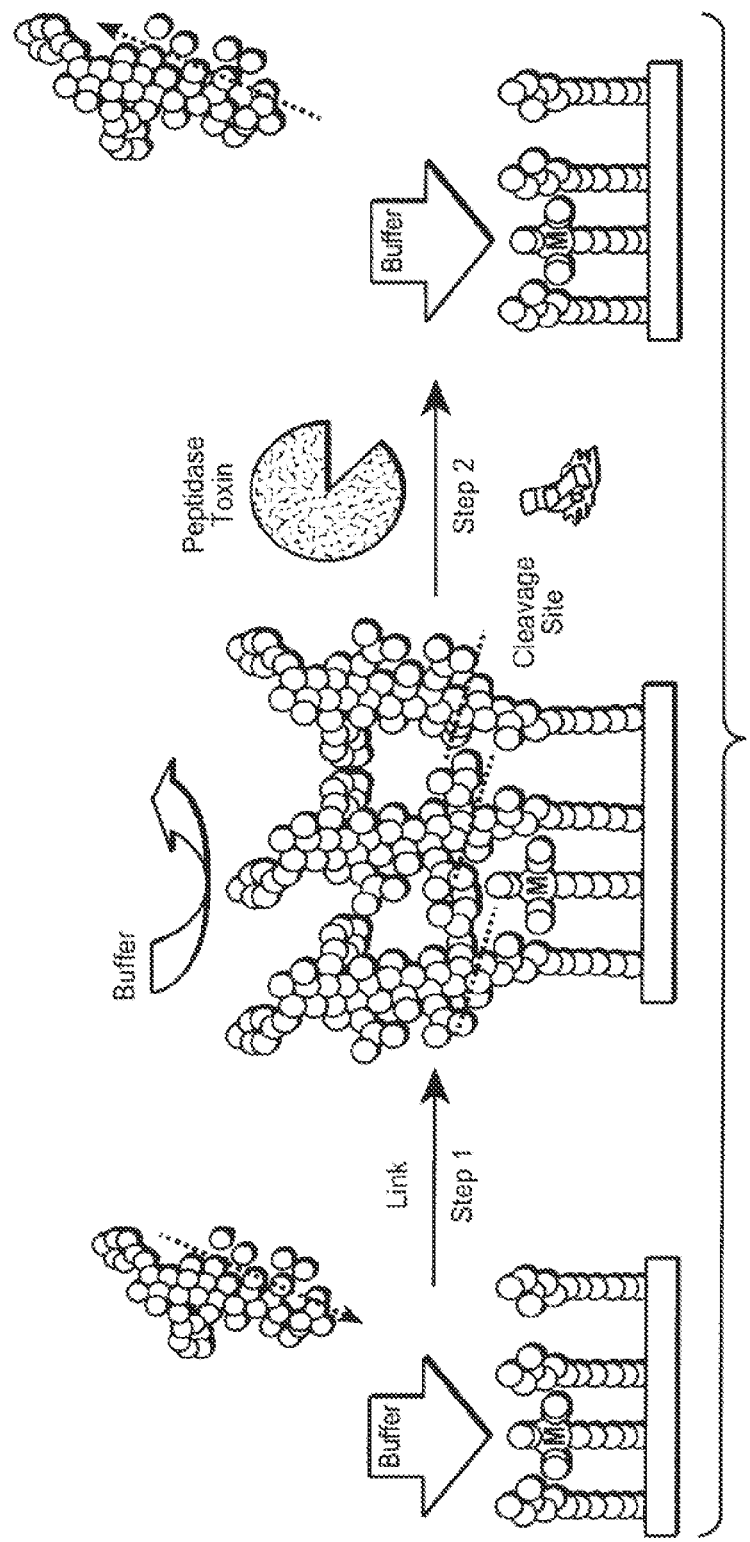
FIG. 2 depicts schematically the electrochemical assay for peptidase toxins according to some embodiments of the present invention.

In some embodiments, the invention embodies a mixed SAM of thiolated EAMs that are "buried" in neighboring capture substrate moieties that are known substrates for a target enzyme. In this arrangement, the EAM is "shielded" from the SAM/solution interface. In the presence of target enzyme, the capture substrate will be catalytically cleaved causing a reduction in SAM height. If the cleavage site is near the height of the EAM in the mixed SAM arrangement, diffusion of the product peptide from the interface will produce "holes" in the monolayer and the EAM component will be exposed to solution. This change in solvation environment of the EAM due to the catalytic "chopping" of neighboring peptides by the target enzyme (like a "lawnmower") will result in a change in potential that can be detected electrochemically. Once a target enzyme is determined and a capture substrate (either synthetic or naturally occurring) identified, the assay can be further optimized by changing the dimensions/concentrations of the EAM and peptide components in the SAM. A graphical representation is shown in FIG. 2. A useful characteristic of the assay is the inherent sensitivity to the enzyme activity, which leads to an amplification of signal per target enzyme molecule.

In some embodiments, the EAM and the capture substrates, the latter comprise a cleavage site, are arranged so that said EAM is at least partially shielded by the substrates from exposing to a solution. Preferably, the cleavage site is near the height of said EAM such as when the substrate is cleaved at the cleavage site, the EAM is exposed to the solution.

In some embodiments, the target enzyme is protease such as a an endopeptidase nuerotoxin produced by the bacterium *Clostridium botulinum*, such as botulinum toxin A, B, or E, as further described below.

One advantage of the present invention is that due to the catalytic nature of enzymes, a single enzyme molecule can result in a number of reactions, thus effectively amplifying the signal and lowering the detection limit.

Figure 3:
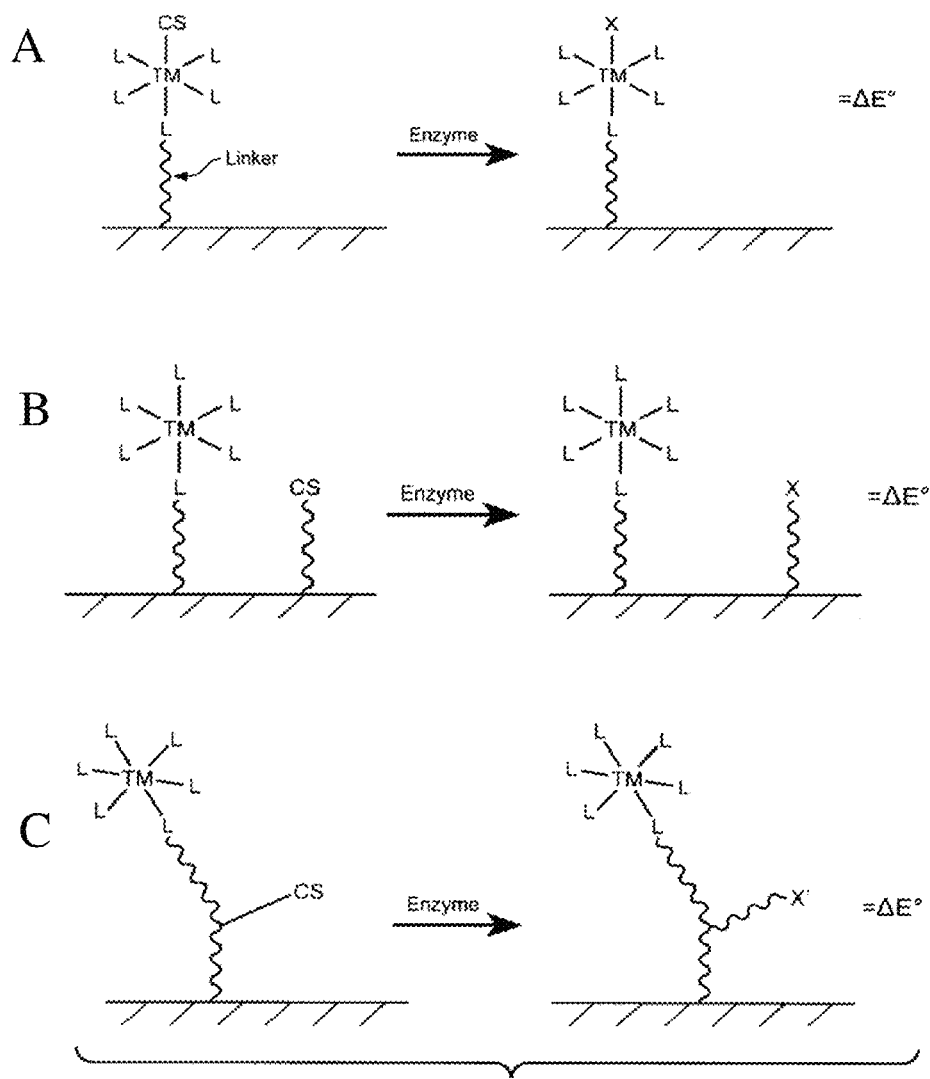
FIG. 3 depicts several schematics of suitable geometries of the present invention.

Several potential schematics of suitable geometries of the invention are shown in FIG. 3.

Figure 7A:
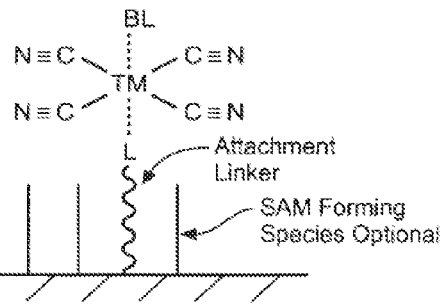
FIGS. 7-9 depict the geometries of exemplary embodiments of the biosensor and schemes of using such biosensor.
Figure 7B:
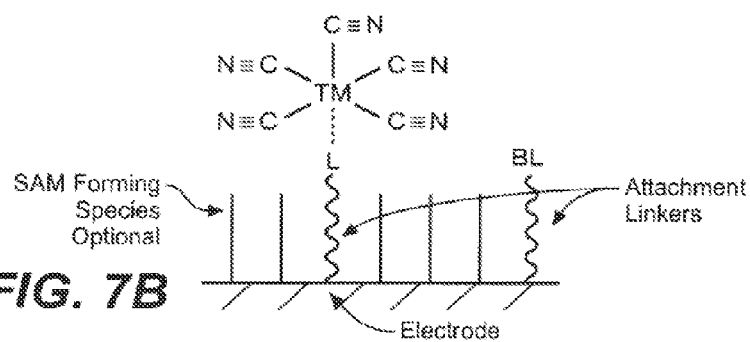
Figure 7C:
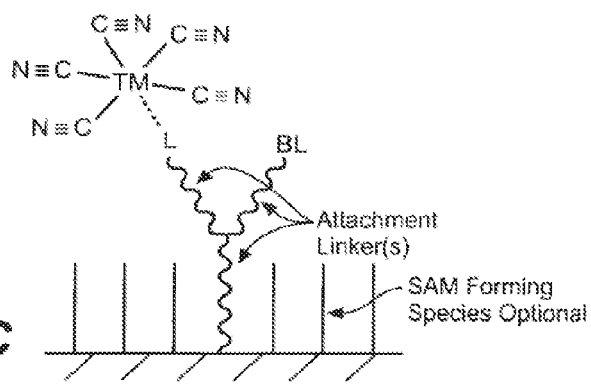
Figure 8:
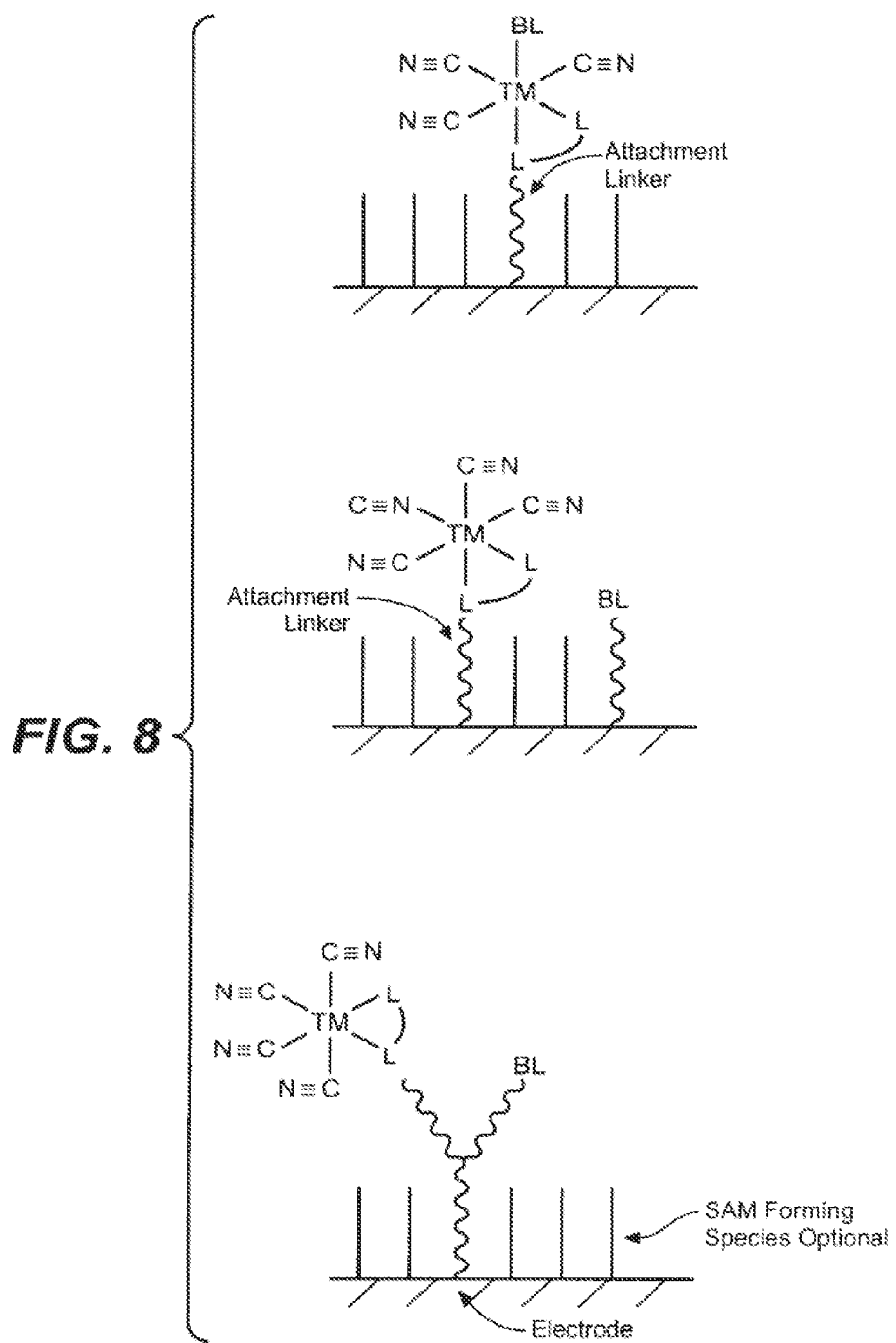
Figure 9:
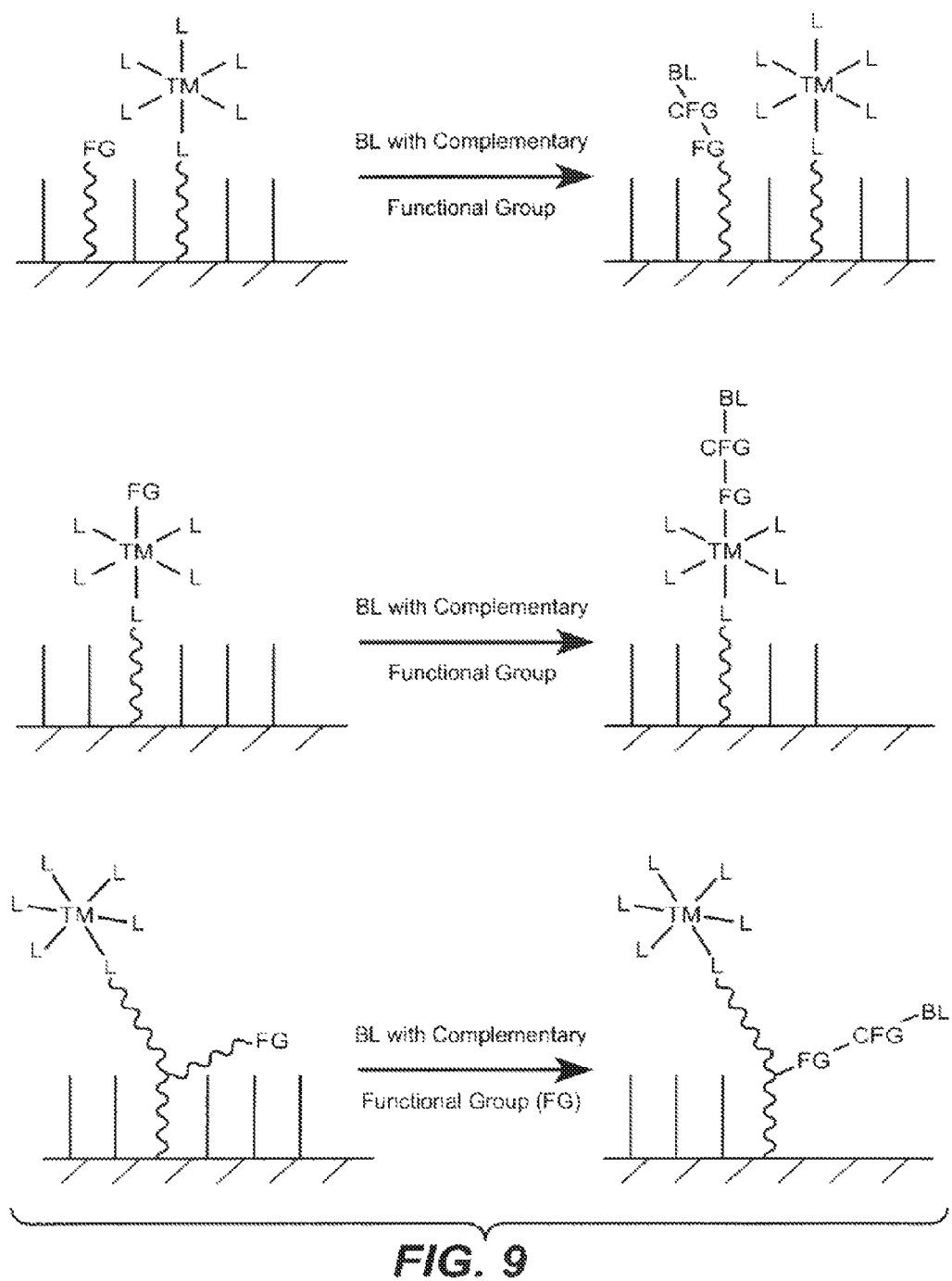

As depicted in FIGS. 7-9, there are three basic geometries for the sensor, although the descriptions herein are not meant to be so limited. In one embodiment, as shown in FIG. 7A, an electroactive moiety (EAM), comprising a transition metal ion and ligands that provide coordination atoms for the transition metal (in some embodiments, at least one of which is a cyano ligand), is attached to an electrode. In addition, a capture ligand (sometimes also referred to as a "binding ligand") that will specifically bind the target analyte is also attached to the electrode. Both species are generally attached to the electrode using an attachment linker as described herein. The two species are attached to the electrode in such a manner that they are spatially close, such that the $E^0$ of the EAM is altered upon binding of a target analyte. It should be noted that a third species, comprising a monolayer forming species, described below, can also be optionally present on the electrode. In this embodiment, the EAM species can have the formula (Ia), the capture ligand species can have the formula (Ib) and the diluent species can have the formula (Ic):

$$AG\text{-Spacer 1-EAM} \tag{Ia}$$

$$AG\text{-Spacer 1-CL} \tag{Ib}$$

$$AG\text{-Spacer 1-TG}_n \tag{Ic}$$

wherein AG is an anchor group, EAM is an electroactive moiety comprises a solvent accessible redox complex, spacer 1 is a SAM forming species described herein, CL is a capture ligand, and TG is a terminal group, with n being 0 or 1.

In a second embodiment, as depicted in FIG. 7B, one of the coordination atoms for the transition metal of the EAM is provided by the capture ligand, forming a "redox active moiety complex", or ReAMC. In this embodiment, the coordination atom can be actually part of the capture ligand (e.g. if the capture ligand is a peptide, an amino group can provide the coordination atom) or part of a linker used to attach the capture ligand (e.g. a pyridine linker, etc.). The ReAMC is attached as a single species, and as above, an additional species, comprising a monolayer forming species, described below, can also be optionally present on the electrode. In this embodiment, the present invention provides a compound having the formula (II):

$$AG\text{-Spacer 1-EAM-(Spacer 2)}_n\text{-CL} \tag{II}$$

wherein AG is an anchor group, EAM is an electroactive moiety comprises a solvent accessible redox complex, CL is a capture ligand, spacer 1 is a SAM forming species described herein, and Spacer 2 is a linker, with n=0 or 1.

In a third embodiment, as depicted in FIG. 7C, there ReAMC is a single species, but the capture ligand does not provide a coordination atom; rather, it is spatially close but distinct from the EAM of the ReAMC. Again, a third species, comprising a monolayer forming species, described below, can also be optionally present on the electrode. In this embodiment, the present invention provides a compound having the formula (III):

$$\begin{array}{c} \text{EAM} \diagdown \quad \diagup \text{CL} \\ S_2 \diagup \diagdown S_3 \\ \text{(branch)} \\ | \\ \text{Spacer 1} \\ | \\ \text{AG} \end{array} \tag{III}$$

wherein AG is an anchor group, EAM is an electroactive moiety comprises a solvent accessible redox complex, CL is a capture ligand, spacer 1 is a SAM forming species described herein, and $S_2$ and $S_3$ are two linkages that link the EAM and CL together with the AG to form a branched structure. $S_2$ and $S_3$ can be different or the same.

In additional, the disclosures of U.S. Pat. Nos. 6,013,459, 6,248,229, 7,018,523, 7,267,939, U.S. patent application Ser. Nos. 09/096,593 and 60/980,733, and U.S. patent application titled "Novel Chemistry In Biosensors" which is filed concurrently with the present application are herein incorporated in their entireties for all purposes.

Accordingly, the present invention provides compositions and methods for electrochemically detecting enzymatic reactions.

I. The Compositions

In one aspect, the present invention provide methods for detecting an enzyme in a test sample using an electrode. The electrode optionally comprises a self-assembled monolayer (SAM) and a covalently attached electroactive active moiety (EAM, also referred to herein as a "redox active molecule" (ReAM)). The EAM comprises a transition metal complex with a first $E^o$. Also attached to the electrode is a plurality of enzyme substrates ("capture substrates", sometimes also referred to herein as "support substrates") of the target enzyme. Thus in this method, the test sample is added to the electrode, the target enzyme and the substrates of the target enzymes form a plurality of reactants. The presence of the enzyme is determined by measuring a change of the $E^o$, resulting from a change in the environment of the EAM.

As is further described below and depicted in FIG. 3. several different geometries can be used in the present invention. In one embodiment, as shown in FIG. 3A, the EAM also includes a capture substrate, forming what is referred to herein as a "redox active moiety complex" or ReAMC. In some embodiments, the capture substrate provides a coordination atom (FIG. 3A); in others, while the ReAMC is a single molecule attached to the electrode, the capture substrate does not provide a coordination atom (FIG. 3C). In other embodiments, as shown in FIG. 3B, there is no ReAMC; rather the EAM and the capture substrate are attached separately to the electrode.

A. Target Enzymes

In one aspect, the present invention provides methods and compositions useful in the detection of target enzymes. By "analyte", "target analyte" or "target enzyme" herein is meant an enzyme to be detected, including, but not limited to, oxoreductases, hydrolases (particularly proteases), lyases, isomerases, transferases (particular kinases), and ligases. See *Enzyme Nomenclature* 1992, Academic Press, San Diego, Calif., with Supplement 1 (1993), Supplement 2 (1994), Supplement 3 (1995), Supplement 4 (1997) and Supplement 5 (in *Eur. J. Biochem.* 1994, 223, 1-5; *Eur. J. Biochem.* 1995, 232, 1-6; *Eur. J. Biochem.* 1996, 237, 1-5; *Eur. J. Biochem.* 1997, 250; 1-6, and *Eur. J. Biochem.* 1999, 264, 610-650; respectively), herein all incorporated by reference in their entirety.

Hydrolase

In some embodiment, the target enzyme is a hydrolase. By "hydrolase" herein is meant an enzyme that catalyzes the hydrolysis of various chemical bonds. They are classified as EC 3 in the EC number classification. Hydrolases include, but are not limited to, enzymes that catalyze ester bonds (esterases, such as nucleases, phophodiesterases, lipases and phosphatases), sugars (carbohydrases including glycosylase/DNA giycosylase, glucoside hydrolase, cellulases, endoglucanases, etc.), ether bonds, peptide bonds (proteases/peptidases), carbon-nitrogen bonds (other than peptide bonds), acid anhydrides (acid anhyride hydrolase, including helicase and GTPase), carbon-carbon bonds, halide bonds, phosphorus-nitrogen bonds, sulfur-nitrogen bonds, carbon-phosphorus bonds, sulfur-sulfur bonds, and carbon-sulfur bonds.

In some embodiments, the hydrolase is a protease (EC 3.4). By "protease" or "proteinase" herein is meant an enzyme that can hydrolyze proteins by hydrolysis of the peptide (amide) bonds that link amino acids. Specifically included within the definition of protease is a peptidase, which specifically refers to an enzyme that hydrolyzes a peptide.

By "proteins" or grammatical equivalents herein is meant proteins, polypeptides, oligopeptides and peptides, derivatives and analogs, including proteins containing non-naturally occurring amino acids and amino acid analogs, and peptidomimetic structures. The side chains may be in either the (R) or the (S) configuration. In a preferred embodiment, the amino acids are in the (S) or L configuration. As discussed below, when the protein is used as a capture substrate it may be desirable to utilize protein analogs to retard degradation by sample contaminants. In general, however, if protein analogues are used as the enzyme substrate, the substrate is still able to be processed by the target enzyme.

Proteases are classified into six groups: serine proteases, threonine proteases, cysteine proteases, aspartic acid proteases, metalloproteases, and glutamic acid proteases. In general, protease can either break specific peptide bonds (e.g. specific segments for limited proteolysis), depending on the amino acid sequence of a protein, or break down a complete protein to amino acids (unlimited proteolysis). The activity can be a destructive change, abolishing a protein's function or digesting it to its principal components; it can be an activation of a function, or it can be a signal in a signaling pathway.

In some embodiments, the target enzyme is an endopeptidase. By "endopeptidase" herein is meant peptidases that break peptide bonds within a protein substrate, in contrast to exopeptidases, which break peptide bonds from one or both termini of the protein substrate. Endopeptidases are divided into subclasses on the basis of catalytic mechanism: the serine endopeptidases, cysteine endopeptidases, aspartic endopeptidases, metalloendopeptidases, and other endopeptidases.

(1). Serine Endopeptidases

This class comprises two distinct families. The chymotrypsin family which includes the mammalian enzymes such as chymotrypsin, trypsin or elastase or kallikrein and the substilisin family which include the bacterial enzymes such as subtilisin. The general three dimensional (3D) structure is different in the two families but they have the same active site geometry and the catalysis proceeds via the same mechanism. The serine endopeptidases exhibit different substrate specificities which are related to amino acid substitutions in the various enzyme subsites interacting with the substrate residues. Some enzymes have an extended interaction site with the substrate whereas others have a specificity restricted to the P1 substrate residue.

(2). Cysteine Endopeptidases

This family includes the plant proteases such as papain, actinidin or bromelain, several mammalian cathepsins, including lysosomal cathepsins and cathepsin B, L, S, H, J, N and O; the cytosolic calpains (calcium-activated) as well as several parasitic proteases (e.g., *Trypanosoma*, *Schistosoma*) and caspases, including interleukin converting enzyme (ICE).

(3). Aspartic Endopeptidases

Most of aspartic endopeptidases belong to the pepsin family. The pepsin family includes digestive enzymes such as pepsin and chymosin as well as lysosomal cathepsins D and processing enzymes such as renin, and certain fungal proteases (penicillopepsin, rhizopuspepsin, endothiapepsin). A second family comprises viral endopeptidases such as the protease from the AIDS virus (HIV) also called retropepsin.

In contrast to serine and cysteine proteases, catalysis by aspartic endopeptidases do not involve a covalent intermediate though a tetrahedral intermediate exists. The nucleophilic attack is achieved by two simultaneous proton transfer: one from a water molecule to the diad of the two carboxyl groups and a second one from the diad to the carbonyl oxygen of the substrate with the concurrent CO—NH bond cleavage.

(4). Metallo Endopeptidases

The metallo endopeptidases are found in bacteria, fungi as well as in higher organisms. They differ widely in their sequences and their structures but the great majority of enzymes contain a zinc atom which is catalytically active. In some cases, zinc may be replaced by another metal such as cobalt or nickel without loss of the activity. Bacterial thermolysin has been well characterized and its crystallographic structure indicates that zinc is bound by two histidines and one glutamic acid. Many enzymes contain the sequence HEXXH, which provides two histidine ligands for the zinc whereas the third ligand is either a glutamic acid (thermolysin, neprilysin, alanyl aminopeptidase) or a histidine (astacin). Other families exhibit a distinct mode of binding of the Zn atom. The catalytic mechanism leads to the formation of a non covalent tetrahedral intermediate after the attack of a zinc-bound water molecule on the carbonyl group of the scissile bond. This intermediate is further decomposed by transfer of the glutamic acid proton to the leaving group.

Of particular interest are metalloenzymes including adenosine deaminase, angiotensin converting enzyme, calcineurin, metallo-beta-lactamase, PDE3, PDE4, PDE5, renal dipeptidase, and urease.

In one embodiment, the metallo endopeptidase is a matrix metalloproteinase, including MMP-1 through MMP-10, particularly MMP-1, MMP-2, MMP-7 and MMP-9.

(5). Bacterial/Toxin Endopeptidases

Toxin endopeptidases, usually of bacterial origin, can have a devastating and sometime lethal impact on host organisms. Some of the better known bacterial endopeptidase toxins are listed below in Table 1.

TABLE 1

Bacterial Endopeptidases

| Organism/ Toxin | Mode of Action | Target (Cleavage Site) | Disease |
|---|---|---|---|
| B. anthracis/ lethal factor | Metalloprotease | MAPKK1/MAPKK2 (multiple) | Anthrax |
| C. botulinum/ neurotxin A | Zinc-metalloprotease | SNAP-25 (ANQ/RAT) | Botulism |
| C. botulinum/ neurotxin B | Zinc-metalloprotease | VAMP/synaptobrevin (ASQ/FET) | Botulism |
| C. botulinum/ neurotxin C | Zinc-metalloprotease | Syntaxin (TKK/AVK) | Botulism |
| C. botulinum/ neurotxin D | Zinc-metalloprotease | VAMP/synaptobrevin (DQK/LSE) | Botulism |
| C. botulinum/ neurotxin E | Zinc-metalloprotease | SNAP-25 (IDR/IME) | Botulism |
| C. botulinum/ neurotxin F | Zinc-metalloprotease | VAMP/synaptobrevin | Botulism |
| C. botulinum/ neurotxin G | Zinc-metalloprotease | VAMP/synaptobrevin (TSA/AKL) | Botulism |
| Yersinia virulence factor YopJ | Cysteine protease | Unknown | |
| Yersinia virulence factor YopT | Cysteine protease | Prenylated cysteine | |
| Salmonella virulence factor AvrA | Unknown | Unknown | Salmonellosis |
| Clostridium tetani/tetanus toxin | Zinc-metalloprotease | VAMP/synaptobrevin (ASQ/FET) | Tetanus |

The *C. botulinum* neurotoxins (BoNTs, serotypes A-G) and the *C. tetani* tetanus neurotoxin (TeNT) are two examples of bacterial toxins that are endopeptidases. BoNTs are most commonly associated with infant and food-borne botulism and exist in nature as large complexes comprised of the neurotoxin and one or more associated proteins believed to provide protection and stability to the toxin molecule while in the gut. TeNT, which is synthesized from vegetative *C. tetani* in wounds, does not appear to form complexes with any other protein components.

BoNTs are highly specific, zinc-dependent endoproteases that specifically cleave small proteins which control the docking of synaptic vesicles with the neural synaptic membrane. BoNT A and BoNT E specifically cleave the 25-kD synaptosomal-associated protein (SNAP-25) with BoNT A cleaves between residues Q197 and R198. SNAP-25 is a presynaptic plasma membrane protein involved in the regulation of neurotransmitter release. Two alternative transcript variants encoding different protein isoforms have been described for this gene in human, SNAP25A (GenBank Accession No. NP_003072) and SNAP25B (GenBank Accession No. NP_70824). BoNT C cleaves the membrane protein syntaxin and SNAP-25. BoNT B, D, F and G are specific for the intracellular vesicle-associated membrane-associated protein (VAMP, also termed synaptobrevin). See Schiavo et al., JBC 266:23784-87 (1995); Schiavo et al., FEBS Letters 335:99-103 (1993), herein are incorporated by reference in their entireties.

Several in vitro assays have been developed based on the cleavage of immobilized synthetic peptide substrates. Halls et al., J Clin Microbiol 34:1934-8 (1996); Witcome et al., Appl Environ Microbiol 65:3787-92 (1999), and Anne et al., Ana Biochem 291:253-61 (2001).

The BoNTs and TeNT are either plasmid encoded (TeNT, BoNTs/A, G, and possibly B) or bacteriophage encoded (BoNTs/C, D, E, F), and the neurotoxins are synthesized as inactive polypeptides of 150 kDa. BoNTs and TeNT are released from lysed bacterial cells and then activated by the proteolytic cleavage of an exposed loop in the neurotoxin polypeptide. Each active neurotoxin molecule consists of a heavy (100 kDa) and light chain (50 kDa) linked by a single interchain disulphide bond. The heavy chains of both the BoNTs and TeNT contain two domains: a region necessary for toxin translocation located in the N-terminal half of the molecule, and a cell-binding domain located within the C-terminus of the heavy chain. The light chains of both the BoNTs and TeNT contain zinc-binding motifs required for the zinc-dependent protease activities of the molecules.

The cellular targets of the BoNTs and TeNT are a group of proteins required for docking and fusion of synaptic vesicles to presynaptic plasma membranes and therefore essential for the release of neurotransmitters. The BoNTs bind to receptors on the presynaptic membrane of motor neurons associated with the peripheral nervous system. Proteolysis of target proteins in these neurons inhibits the release of acetylcholine, thereby preventing muscle contraction. BoNTs/B, D, F, and G cleave the vesicle-associated membrane protein and synaptobrevin, BoNT/A and E target the synaptosomal-associated protein SNAP-25, and BoNT/C hydrolyzes syntaxin and SNAP-25. TeNT affects the central nervous system and does so by entering two types of neurons. TeNT initially binds to receptors on the presynaptic membrane of motor neurons but then migrates by retrograde vesicular transport to the spinal cord, where the neurotoxin can enter inhibitory interneurons. Cleavage of the vesicle-associated membrane protein and synaptobrevin in these neurons disrupts the release of glycine and gamma-amino-butyric acid, which, in turn, induces muscle contraction. The contrasting clinical manifestations of BoNT or TeNT intoxication (flaccid and spastic paralysis, respectively) are the direct result of the specific neurons affected and the type of neurotransmitters blocked.

Of particular interest is BoNT/LC (serotype C), and specifically BoNTC/LC (as compared to other LC serotypes). First, BoNTC/LC poses a particularly significant bioterror threat because it has a long half-life inside human neuronal cells. Second, an in vitro assay for BoNTC/LC does not currently exist, probably because this LC protease appears to require membranes to function. In the neuronal cell environment, BoNTC/LC cleaves syntaxin, a membrane protein required for synaptic vesicle fusion to the presynaptic membrane.

Other examples include the *Yersinia* virulence factors YopJ and YopT, as well as *Salmonella* AvrA.

Transferases

In some embodiments, the target enzyme is a transferase. By "transferase" herein is meant an enzyme that catalyzes the transfer of a functional group (e.g. a methyl or phosphate group) from one molecule (the donor) to another (the acceptor).

Transferases are classified as EC 2 in the EC number classification. Transferases can be further classified into nine subclasses: enzymes that transfer one-carbon groups (methyltransferase), enzymes that transfer aldehyde or ketone groups, acyltransferases, glycosyltransferases, enzymes that transfer alkyl or aryl groups, other than methyl groups, enzymes that transfer nitrogenous groups (transaminase), enzymes that transfer phosphorus-containing groups (phosphotransferase, including polymerase and kinase), enzymes that transfer sulfur-containing groups (sulfurtransferase and sulfotransferase), and enzymes that transfer selenium-containing groups.

In some embodiments, the target enzyme is a kinase, as described herein.

In another aspect, the present invention provides compositions and methods for detecting kinases. Analytical methods to quantify protein kinase activity are critical for understanding their role in the diagnosis and therapy of diseases. The kinase assays provided herein can also be used to screen for drug candidate inhibitors of kinase.

Eukaryotes employ phosphorylation and dephosphorylation of specific proteins to regulate many cellular processes. T. Hunter, *Cell* 80:225-236 (1995); Karin, M., Curr. Opin. Cell Biol. 3:467-473 (1991). These processes include signal transduction, cell division, and initiation of gene transcription. Thus, significant events in an organism's maintenance, adaptation, and susceptibility to disease are controlled by protein phosphorylation and dephosphorylation. These phenomena are so extensive that it has been estimated that humans have around 2,000 protein kinase genes and 1,000 protein phosphatase genes, T. Hunter, Cell 80:225-236 (1995), some of these likely coding for disease susceptibility. For these reasons, protein kinases and phosphatases are good targets for the development of drug therapies.

Some of the frequently used protein kinase screens employ either radioactive ATP or ELISAs. However, the use of radioactive ATP is undesirable due to the attendant costs of record-keeping, waste-disposal, and the fact that the assay format is not homogeneous. ELISAs are undesirable because they have a lower assay throughput due to the extra steps required for both washing and the enzyme reaction.

Fluorescence detection in the visible wavelengths offer an alternative to the use of radiotracers or ELISAs for kinase assays, as fluorescence offers detection limits comparable to those of radioactivity. Furthermore, this eliminates the cost of radioactive waste disposal. However, previously developed fluorometric assays for kinases have not been especially amenable to the requirements of high throughput screening.

Electrochemical detection of kinase activity using a Ferrocene-conjugated ATP (Fc-ATP) has been described. Song et al., Chem. Commun., 502-504 (2008). In this assay, a substrate of protein kinase C (PKC) is immobilized on the surface of an electrode. PKC-catalyzed reaction transfers a γ-phosphate-Fc group to the serine residue of the peptide. The electrode surface-attached Fc groups are detected using electrochemical techniques. Thus in this assay the Ferrocene is not attached to the electrode prior to the phosphorylation; it only attaches to attached to the electrode through the phosphorylation process.

Also has been described is electrochemical detection of protein kinase C (PLC)-catalyzed thiophorylation using gold particle. Kerman and Kraatz, Chem. Commun. 5019-5021 (2007). In this assay, a biotinylated substrate peptide is immobilized on the surface of a streptaavidin-coated carbon electrode. PKC-catalyzed reaction transfers a thiophosphate group to the serine residue of the peptide. The incubation of the thiophosyrrylated peptide with gold particle causes the attachment of gold particle on the surface. The presence of the gold particle is determined by the electrochemical reduction response obtained from the chloride ions on god particle. Thus in this assay the gold particle is not attached to the electrode prior to the phosphorylation; it only attaches to attached to the electrode through the phosphorylation process.

In some embodiment, the target analyte is a protein kinase. By "kinase" or "phosphotransferase" herein is meant an enzyme that transfers phosphate groups from high-energy donor molecules, such as ATP, to specific target molecules (substrates). This process of transfer is termed phosphorylation. Thus, protein kinase catalyzes the transfer of phosphorous from adenosine triphosphate (ATP), or guanosine triphosphate (GTP) to the targeted protein to yield a phosphorylated protein and adenosine diphosphate (ADP) or guanosine diphosphate (GDP), respectively. ATP or GTP is first hydrolyzed to form ADP or GDP and inorganic phosphate. The inorganic phosphate is then attached to the targeted protein. The protein substrate which is targeted by kinases may be a structural protein, found in membrane material such as a cell wall, or another enzyme which is a functional protein.

Due to their physiological relevance, variety and ubiquitousness, protein kinases have become one of the most important and widely studied families of enzymes in biochemical and medical research. Studies have shown that protein kinases are key regulators of many cell functions, including signal transduction, transcriptional regulation, cell motility, and cell division. Several oncogenes have also been shown to encode protein kinases, suggesting that kinases play a role in oncogenesis.

Protein kinases are often divided into two groups based on the amino acid residue they phosphorylate. The first group, called serine/threonine kinases, includes cyclic AMP and cyclic GMP dependent protein kinases, calcium and phospholipid dependent protein kinase, calcium and calmodulin-dependent protein kinases, casein kinases, cell division cycle protein kinases and others. These kinases are usually cytoplasmic or associated with the particulate fractions of cells, possibly by anchoring proteins.

The second group of kinases, called tyrosine kinases, phosphorylate tyrosine residues. They are present in much smaller quantities but play an equally important role in cell regulation. These kinases include several receptors for molecules such as growth factors and hormones, including epidermal growth factor receptor, insulin receptor, platelet derived growth factor receptor and others. Studies have indicated that many tyrosine kinases are transmembrane proteins with their receptor domains located on the outside of the cell and their kinase domains on the inside.

Phosphorylation of serine-, threonine- and tyrosine-containing proteins by kinases is important because the phosphorylated protein products have been implicated in a variety of cellular processes including oncogenesis, cellular transformation, cellular growth and exocytosis.

Oxidoreductases

In some embodiments, the target enzyme is an oxidoreductase. An oxidoreductase is an enzyme that catalyzes the transfer of electrons from one molecule (the oxidant, also called the hydrogen donor or electron donor) to another (the reductant, also called the hydrogen acceptor or electron acceptor). Oxidoreductases are classified as EC 1 in the EC number classification of enzymes. Oxidoreductases can be further classified into 22 subclasses. Many oxidoreductase enzymes are metalloenzymes that contain one or more metal ions. Some examplary enzymes in this group are 4-hydroxyphenylpyruvate dioxygenase, 5-lipoxygenase, alcohol dehydrogenase, aldehyde dehydrogenase, aromatase, cyclooxygenase, cytochrome P450, fumarate reductase, heme oxygenase, lanosterol demethylase, pyruvate:ferredoxin oxidoreductase, ribonucleoside diphosphate reductase, thyroid peroxidase, and xanthine oxidase.

Lyase

In some embodiments, the target enzyme is a lyase. By "lyase" herein is meant an enzyme that catalyzes the breaking of various chemical bonds by means other than hydrolysis and oxidation, often forming a new double bond or a new ring structure.

Lysases are classified as EC 4 in the EC number classification of enzymes. Lyases can be further classified into seven subclasses: (1) lyases that cleave carbon-carbon bonds, such as decarboxylases, aldehyde lyases, and oxo acid lyases; (2) lyases that cleave carbon-oxygen bonds, such as dehydratases; (3) lyases that cleave carbon-nitrogen bonds; (4) lyases that cleave carbon-sulfur bonds; (5) lyases that cleave carbon-halide bonds; (6) lyases that cleave phosphorus-oxygen bonds, such as adenylate cyclase and guanylate cyclase; and (7) other lyases, such as ferrochelatase.

Isomerase

In some embodiments, the target enzyme is an isomerase. By "isomerase" herein is meant an enzyme that catalyses the structural rearrangement of isomers.

Isomerases have their own EC classification of enzymes: EC 5. Isomerases can be further classified into six subclasses: (1) enzymes that catalyze racemization (racemases) and epimerization (epimerases); (2) enzymes that catalyze the isomerization of geometric isomers (cis-trans isomerases); (3) intramolecular oxidoreductases; (4) intramolecular transferases (mutases); (5) intramolecular lyases, and (6) other isomerases (including topoisomerases).

Ligases

In some embodiments, the target enzyme is a ligase. By "ligase" herein is meant an enzyme that catalyzes the joining of two molecules with concomitant hydrolysis of the diphosphate bond in ATP or a similar triphosphate.

Ligases are classified as EC 6 in the EC number classification of enzymes. Ligases can be further classified into six subclasses: (1) enzymes for forming carbon-oxygen bonds (e.g. enzymes acylating a transfer RNA with the corresponding amino acid (amino-acid-tRNA ligases)); (2) enzymes for forming carbon-sulfur bonds (e.g. enzymes synthesizing acyl-CoA derivatives); (3) enzymes for forming carbon-nitrogen bonds (e.g. amide synthases, peptide synthases, enzymes forming heterocyclic rings, enzymes using glutamine as amido-N-donor) and others; (4) enzymes for forming carbon-carbon bonds (the carboxylating enzymes, mostly biotinyl-proteins); (5) enzymes for forming phosphoric ester bonds (e.g. enzymes restoring broken phosphodiester bonds in the nucleic acids (often called repair enzymes)), and (6) enzymes for forming nitrogen-metal bonds (e.g. metal chelation of a tetrapyrrole ring system).

B. Substrates of the Target Enzymes

The substrates being used in the present invention depends on the target enzyme. Enzyme/substrate relationships are generally well known as being characteristics of the relevant target enzyme. As described herein, there are two types of substrates which may find use in the invention, depending on the target enzyme: a "capture substrate" and a "solution substrate".

"Capture substrates" are substrates for the target enzyme, and generally are those that undergo a conformational change based on change in covalent bonds upon contact with the corresponding enzyme. For example, the substrate can be cleaved if the enzyme is a protease, as more fully described below. Similarly, the substrate can under go a spatial rearrangement, such as for the case with transferases and isomerases. It should be understood that "capture substrate" (sometimes referred to herein as "support substrate") need not actually capture the target on the surface, rather, it is attached to the surface. In general, capture substrates are used for enzymes that break covalent bonds, such as hydrolases, isomerases and transferases.

A "solution substrate" is used with target enzymes that synthesize bonds, in enzymatic reactions that result in the addition of two or more substrates to form a single reactant (also referred to as a "product"). For example, ligases can be used to synthesize a longer peptide from two shorter peptides or to ligate two nucleic acids together (e.g. a capture substrate on the surface and a solution substrate in the assay). Another example would be nucleic acid synthesis, where a nucleic acid is on the surface and nucleotides are added to the capture substrate. Kinases also fall into this class, as described herein.

Suitable target enzyme/substrate pairs include, but are not limited to, protease/protein, (including protease/peptide), ligase/nucleic acids, ligase/proteins, lipase/lipid, carbohydrase/carbohydrate, kinase/phosphate groups, etc.

For example, when the target enzyme is a protease, the substrate is generally a protein, including peptides, that is cleaved by the target enzyme. In some embodiments, smaller capture substrates are preferred, such as peptides, although larger proteins can be used as well. Again, what is important is that the electrochemical potential of the nearby ReAM is altered as a result of the action of the enzyme. The substrate preferably also comprises a sequence that can confer specificity to the cleavage, such that each substrate can only be cleaved by one or more specific target enzyme.

For example, when the target enzyme is one of the BoNT, the substrate comprises a sequence derived from as known substrate of BoNT, such as SNAP-25 or VAMP), with or without optimization, such as by genetic engineering.

C. Electrodes

In one aspect, the present invention provides these ligand architectures attached to an electrode. By "electrode" herein is meant a composition, which, when connected to an electronic device, is able to sense a current or charge and convert it to a signal. Preferred electrodes are known in the art and include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide ($Mo_2O_6$), tungsten oxide ($WO_3$) and ruthenium oxides; and carbon (including glassy carbon electrodes, graphite and carbon paste). Preferred electrodes include gold, silicon, carbon and metal oxide electrodes, with gold being particularly preferred.

The electrodes described herein are depicted as a flat surface, which is only one of the possible conformations of the electrode and is for schematic purposes only. The conformation of the electrode will vary with the detection method used. For example, flat planar electrodes may be preferred for optical detection methods, or when arrays of nucleic acids are made, thus requiring addressable locations for both synthesis and detection. Alternatively, for single probe analysis, the electrode may be in the form of a tube, with the components of the system such as SAMs, EAMs and capture ligands bound to the inner surface. This allows a maximum of surface area containing the nucleic acids to be exposed to a small volume of sample.

The electrodes of the invention are generally incorporated into biochip cartridges and can take a wide variety of configurations, and can include working and reference electrodes, interconnects (including "through board" interconnects), and microfluidic components. See for example U.S. Pat. No. 7,312,087, incorporated herein by reference in its entirety.

The biochip cartridges include substrates comprising the arrays of biomolecules, and can be configured in a variety of ways. For example, the chips can include reaction chambers with inlet and outlet ports for the introduction and removal of reagents. In addition, the cartridges can include caps or lids that have microfluidic components, such that the sample can be introduced, reagents added, reactions done, and then the sample is added to the reaction chamber comprising the array for detection.

In a preferred embodiment, the biochips comprise substrates with a plurality of array locations. By "substrate" or "solid support" or other grammatical equivalents herein is meant any material that can be modified to contain discrete individual sites appropriate of the attachment or association of capture ligands. Suitable substrates include metal surfaces such as gold, electrodes as defined below, glass and modified or functionalized glass, fiberglass, teflon, ceramics, mica, plastic (including acrylics, polystyrene and copolymers of styrene and other materials, polypropylene, polyethylene, polybutylene, polyimide, polycarbonate, polyurethanes, Teflon™, and derivatives thereof, etc.), GETEK (a blend of polypropylene oxide and fiberglass), etc, polysaccharides, nylon or nitrocellulose, resins, silica or silica-based materials including silicon and modified silicon, carbon, metals, inorganic glasses and a variety of other polymers, with printed circuit board (PCB) materials being particularly preferred.

The present system finds particular utility in array formats, i.e. wherein there is a matrix of addressable detection electrodes (herein generally referred to "pads", "addresses" or "micro-locations"). By "array" herein is meant a plurality of capture ligands in an array format; the size of the array will depend on the composition and end use of the array. Arrays containing from about 2 different capture substrates to many thousands can be made.

In a preferred embodiment, the detection electrodes are formed on a substrate. In addition, the discussion herein is generally directed to the use of gold electrodes, but as will be appreciated by those in the art, other electrodes can be used as well. The substrate can comprise a wide variety of materials, as outlined herein and in the cited references.

In general, preferred materials include printed circuit board materials. Circuit board materials are those that comprise an insulating substrate that is coated with a conducting layer and processed using lithography techniques, particularly photolithography techniques, to form the patterns of electrodes and interconnects (sometimes referred to in the art as interconnections or leads). The insulating substrate is generally, but not always, a polymer. As is known in the art, one or a plurality of layers may be used, to make either "two dimensional" (e.g. all electrodes and interconnections in a plane) or "three dimensional" (wherein the electrodes are on one surface and the interconnects may go through the board to the other side or wherein electrodes are on a plurality of surfaces) boards. Three dimensional systems frequently rely on the use of drilling or etching, followed by electroplating with a metal such as copper, such that the "through board" interconnections are made. Circuit board materials are often provided with a foil already attached to the substrate, such as a copper foil, with additional copper added as needed (for example for interconnections), for example by electroplating. The copper surface may then need to be roughened, for example through etching, to allow attachment of the adhesion layer.

Accordingly, in a preferred embodiment, the present invention provides biochips (sometimes referred to herein "chips") that comprise substrates comprising a plurality of electrodes, preferably gold electrodes. The number of electrodes is as outlined for arrays. Each electrode preferably comprises a self-assembled monolayer as outlined herein. In a preferred embodiment, one of the monolayer-forming species comprises a capture ligand as outlined herein. In addition, each electrode has an interconnection, that is attached to the electrode at one end and is ultimately attached to a device that can control the electrode. That is, each electrode is independently addressable.

Finally, the compositions of the invention can include a wide variety of additional components, including microfluidic components and robotic components (see for example U.S. Pat. Nos. 6,942,771 and 7,312,087 and related cases, both of which are hereby incorporated by reference in its entirety), and detection systems including computers utilizing signal processing techniques (see for example U.S. Pat. No. 6,740,518, hereby incorporated by reference in its entirety)

(a). Self Assembled Monolayer Spacers

In some embodiments, the electrodes optionally further comprise a SAM. By "monolayer" or "self-assembled monolayer" or "SAM" herein is meant a relatively ordered assembly of molecules spontaneously chemisorbed on a surface, in which the molecules are oriented approximately parallel to each other and roughly perpendicular to the surface. Each of the molecules includes a functional group that adheres to the surface, and a portion that interacts with neighboring molecules in the monolayer to form the relatively ordered array. A "mixed" monolayer comprises a heterogeneous monolayer, that is, where at least two different molecules make up the monolayer. As outlined herein, the use of a monolayer reduces the amount of non-specific binding of biomolecules to the surface, and, in the case of nucleic acids, increases the efficiency of oligonucleotide hybridization as a result of the distance of the oligonucleotide from the electrode. Thus, a monolayer facilitates the maintenance of the target enzyme away from the electrode surface. In addition, a monolayer serves to keep charge carriers away from the surface of the electrode. Thus, this layer helps to prevent electrical contact between the electrodes and the ReAMs, or between the electrode and charged species within the solvent. Such contact can result in a direct "short circuit" or an indirect short circuit via charged species which may be present in the sample. Accordingly, the monolayer is preferably tightly packed in a uniform layer on the electrode surface, such that a minimum of "holes" exist. The monolayer thus serves as a physical barrier to block solvent accesibility to the electrode.

In some embodiments, the monolayer comprises conductive oligomers. By "conductive oligomer" herein is meant a substantially conducting oligomer, preferably linear, some embodiments of which are referred to in the literature as "molecular wires". By "substantially conducting" herein is meant that the oligomer is capable of transferring electrons at 100 Hz. Generally, the conductive oligomer has substantially overlapping TT-orbitals, i.e. conjugated TT-orbitals, as between the monomeric units of the conductive oligomer, although the conductive oligomer may also contain one or more sigma (a) bonds. Additionally, a conductive oligomer may be defined functionally by its ability to inject or receive electrons into or from an associated EAM. Furthermore, the conductive oligomer is more conductive than the insulators as defined herein. Additionally, the conductive oligomers of the invention are to be distinguished from electroactive polymers, that themselves may donate or accept electrons.

A more detailed description of conductive oligomers is found in WO/1999/57317, herein incorporated by reference in its entirety. In particular, the conductive oligomers as shown in Structures 1 to 9 on page 14 to 21 of WO/1999/57317 find use in the present invention. In some embodiments, the conductive oligomer has the following structure:

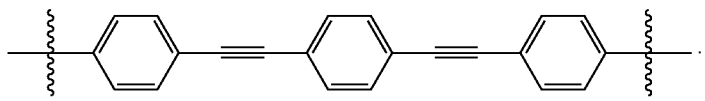 [SMILES: *c1ccc(C#Cc2ccc(C#Cc3ccc(*)cc3)cc2)cc1]

In addition, the terminus of at least some of the conductive oligomers in the monolayer is electronically exposed. By "electronically exposed" herein is meant that upon the placement of an EAM in close proximity to the terminus, and after initiation with the appropriate signal, a signal dependent on the presence of the EAM may be detected. The conductive oligomers may or may not have terminal groups. Thus, in a preferred embodiment, there is no additional terminal group, and the conductive oligomer terminates with a terminal group; for example, such as an acetylene bond. Alternatively, in some embodiments, a terminal group is added, sometimes depicted herein as "Q". A terminal group may be used for several reasons; for example, to contribute to the electronic availability of the conductive oligomer for detection of EAMs, or to alter the surface of the SAM for other reasons, for example to prevent non-specific binding. For example, there may be negatively charged groups on the terminus to form a negatively charged surface such that when the target analyte is nucleic acid such as DNA or RNA, the nucleic acid is repelled or prevented from lying down on the surface, to facilitate hybridization. Preferred terminal groups include —NH, —OH, —COOH, and alkyl groups such as —CH$_3$, and (poly)alkyloxides such as (poly)ethylene glycol, with —OCH$_2$CH$_2$OH, —(OCH$_2$CH$_2$O)$_2$H, —(OCH$_2$CH$_2$O)$_3$H, and —(OCH$_2$CH$_2$O)$_4$H being preferred.

In one embodiment, it is possible to use mixtures of conductive oligomers with different types of terminal groups. Thus, for example, some of the terminal groups may facilitate detection, and some may prevent non-specific binding.

In some embodiments, the electrode further comprises a passivation agent, preferably in the form of a monolayer on the electrode surface. For some analytes the efficiency of analyte binding (i.e. hybridization) may increase when the binding ligand is at a distance from the electrode. In addition, the presence of a monolayer can decrease non-specific binding to the surface (which can be further facilitated by the use of a terminal group, outlined herein. A passivation agent layer facilitates the maintenance of the binding ligand and/or analyte away from the electrode surface. In addition, a passivation agent serves to keep charge carriers away from the surface of the electrode. Thus, this layer helps to prevent electrical contact between the electrodes and the electron transfer moieties, or between the electrode and charged species within the solvent. Such contact can result in a direct "short circuit" or an indirect short circuit via charged species which may be present in the sample. Accordingly, the monolayer of passivation agents is preferably tightly packed in a uniform layer on the electrode surface, such that a minimum of "holes" exist. Alternatively, the passivation agent may not be in the form of a monolayer, but may be present to help the packing of the conductive oligomers or other characteristics.

The passivation agents thus serve as a physical barrier to block solvent accessibility to the electrode. As such, the passivation agents themselves may in fact be either (1) conducting or (2) nonconducting, i.e. insulating, molecules. Thus, in one embodiment, the passivation agents are conductive oligomers, as described herein, with or without a terminal group to block or decrease the transfer of charge to the electrode. Other passivation agents which may be conductive include oligomers of —(CF$_2$)$_n$—, —(CHF)$_n$— and —(CFR)$_n$—. In a preferred embodiment, the passivation agents are insulator moieties.

In some embodiments, the monolayers comprise insulators. An "insulator" is a substantially nonconducting oligomer, preferably linear. By "substantially nonconducting" herein is meant that the rate of electron transfer through the insulator is slower than the rate of electron transfer through the conductive oligomer. Stated differently, the electrical resistance of the insulator is higher than the electrical resistance of the conductive oligomer. It should be noted however that even oligomers generally considered to be insulators, such as —(CH2)16 molecules, still may transfer electrons, albeit at a slow rate.

In some embodiments, the insulators have a conductivity, S, of about 10-7Ω-1 cm-1 or lower, with less than about 10-8Ω-1 cm-1 being preferred. Gardner et al., Sensors and Actuators A 51 (1995) 57-66, incorporated herein by reference.

Generally, insulators are alkyl or heteroalkyl oligomers or moieties with sigma bonds, although any particular insulator molecule may contain aromatic groups or one or more conjugated bonds. By "heteroalkyl" herein is meant an alkyl group that has at least one heteroatom, i.e. nitrogen, oxygen, sulfur, phosphorus, silicon or boron included in the chain. Alternatively, the insulator may be quite similar to a conductive oligomer with the addition of one or more heteroatoms or bonds that serve to inhibit or slow, preferably substantially, electron transfer. In some embodiments the insulator comprises C6-C16 alkyl.

The passivation agents, including insulators, may be substituted with R groups as defined herein to alter the packing of the moieties or conductive oligomers on an electrode, the hydrophilicity or hydrophobicity of the insulator, and the flexibility, i.e. the rotational, torsional or longitudinal flexibility of the insulator. For example, branched alkyl groups may be used. In addition, the terminus of the passivation agent, including insulators, may contain an additional group to influence the exposed surface of the monolayer, sometimes referred to herein as a terminal group ("TG"). For example, the addition of charged, neutral or hydrophobic groups may be done to inhibit non-specific binding from the sample, or to influence the kinetics of binding of the analyte, etc. For example, there may be charged groups on the terminus to form a charged surface to encourage or discourage binding of certain target analytes or to repel or prevent from lying down on the surface.

The length of the passivation agent will vary as needed. Generally, the length of the passivation agents is similar to the length of the conductive oligomers, as outlined above. In addition, the conductive oligomers may be basically the same length as the passivation agents or longer than them, resulting in the binding ligands being more accessible to the solvent.

The monolayer may comprise a single type of passivation agent, including insulators, or different types.

Suitable insulators are known in the art, and include, but are not limited to, —(CH$_2$)$_n$—, —(CRH)$_n$—, and —(CR$_2$)$_n$—, ethylene glycol or derivatives using other heteroatoms in place of oxygen, i.e. nitrogen or sulfur (sulfur derivatives are not preferred when the electrode is gold). In some embodiments, the insulator comprises C6 to C16 alkyl.

In some embodiments, the electrode is a metal surface and need not necessarily have interconnects or the ability to do electrochemistry.

(b). Anchor Groups

The present invention provides compounds comprising an anchor group. By "anchor" or "anchor group" herein is meant a chemical group that attaches the compounds of the invention to an electrode.

As will be appreciated by those in the art, the composition of the anchor group will vary depending on the composition of the surface to which it is attached. In the case of gold electrodes, both pyridinyl anchor groups and thiol based anchor groups find particular use.

The covalent attachment of the conductive oligomer may be accomplished in a variety of ways, depending on the electrode and the conductive oligomer used. Generally, some type of linker is used, as depicted below as "A" in Structure 1, where X is the conductive oligomer, and the hatched surface is the electrode:

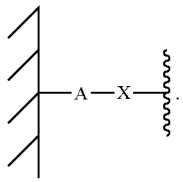

Structure 1

In this embodiment, A is a linker or atom. The choice of "A" will depend in part on the characteristics of the electrode. Thus, for example, A may be a sulfur moiety when a gold electrode is used. Alternatively, when metal oxide electrodes are used, A may be a silicon (silane) moiety attached to the oxygen of the oxide (see for example Chen et al., Langmuir 10:3332-3337 (1994); Lenhard et al., J. Electroanal. Chem. 78:195-201 (1977), both of which are expressly incorporated by reference). When carbon based electrodes are used, A may be an amino moiety (preferably a primary amine; see for example Deinhammer et al., Langmuir 10:1306-1313 (1994)). Thus, preferred A moieties include, but are not limited to, silane moieties, sulfur moieties (including alkyl sulfur moieties), and amino moieties.

In some embodiments, the electrode is a carbon electrode, i.e. a glassy carbon electrode, and attachment is via a nitrogen of an amine group. A representative structure is depicted in Structure 15 of US Patent Application Publication No. 20080248592, hereby incorporated by reference in its entirety but particularly for Structures as described therein and the description of different anchor groups and the accompanying text. Again, additional atoms may be present, i.e. linkers and/or terminal groups.

In Structure 16 of US Patent Application Publication No. 20080248592, hereby incorporated by reference as above, the oxygen atom is from the oxide of the metal oxide electrode. The Si atom may also contain other atoms, i.e. be a silicon moiety containing substitution groups. Other attachments for SAMs to other electrodes are known in the art; see for example Napier et al., Langmuir, 1997, for attachment to indium tin oxide electrodes, and also the chemisorption of phosphates to an indium tin oxide electrode (talk by H. Holden Thorpe, CHI conference, May 4-5, 1998).

In one preferred embodiment, indium-tin-oxide (ITO) is used as the electrode, and the anchor groups are phosphonate-containing species.

1). Sulfur Anchor Groups

Although depicted in Structure 1 as a single moiety, the conductive oligomer may be attached to the electrode with more than one "A" moiety; the "A" moieties may be the same or different. Thus, for example, when the electrode is a gold electrode, and "A" is a sulfur atom or moiety, multiple sulfur atoms may be used to attach the conductive oligomer to the electrode, such as is generally depicted below in Structures 2, 3 and 4. As will be appreciated by those in the art, other such structures can be made. In Structures 2, 3 and 4 the A moiety is just a sulfur atom, but substituted sulfur moieties may also be used.

Thus, for example, when the electrode is a gold electrode, and "A" is a sulfur atom or moiety, such as generally depicted below in Structure 6, multiple sulfur atoms may be used to attach the conductive oligomer to the electrode, such as is generally depicted below in Structures 2, 3 and 4. As will be appreciated by those in the art, other such structures can be made. In Structures 2, 3 and 4, the A moiety is just a sulfur atom, but substituted sulfur moieties may also be used.

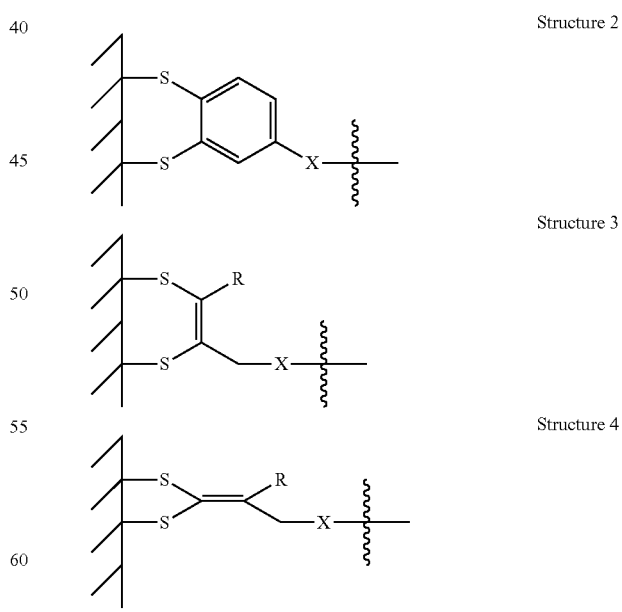

It should also be noted that similar to Structure 4, it may be possible to have a conductive oligomer terminating in a single carbon atom with three sulfur moieties attached to the electrode.

Figure 4A:
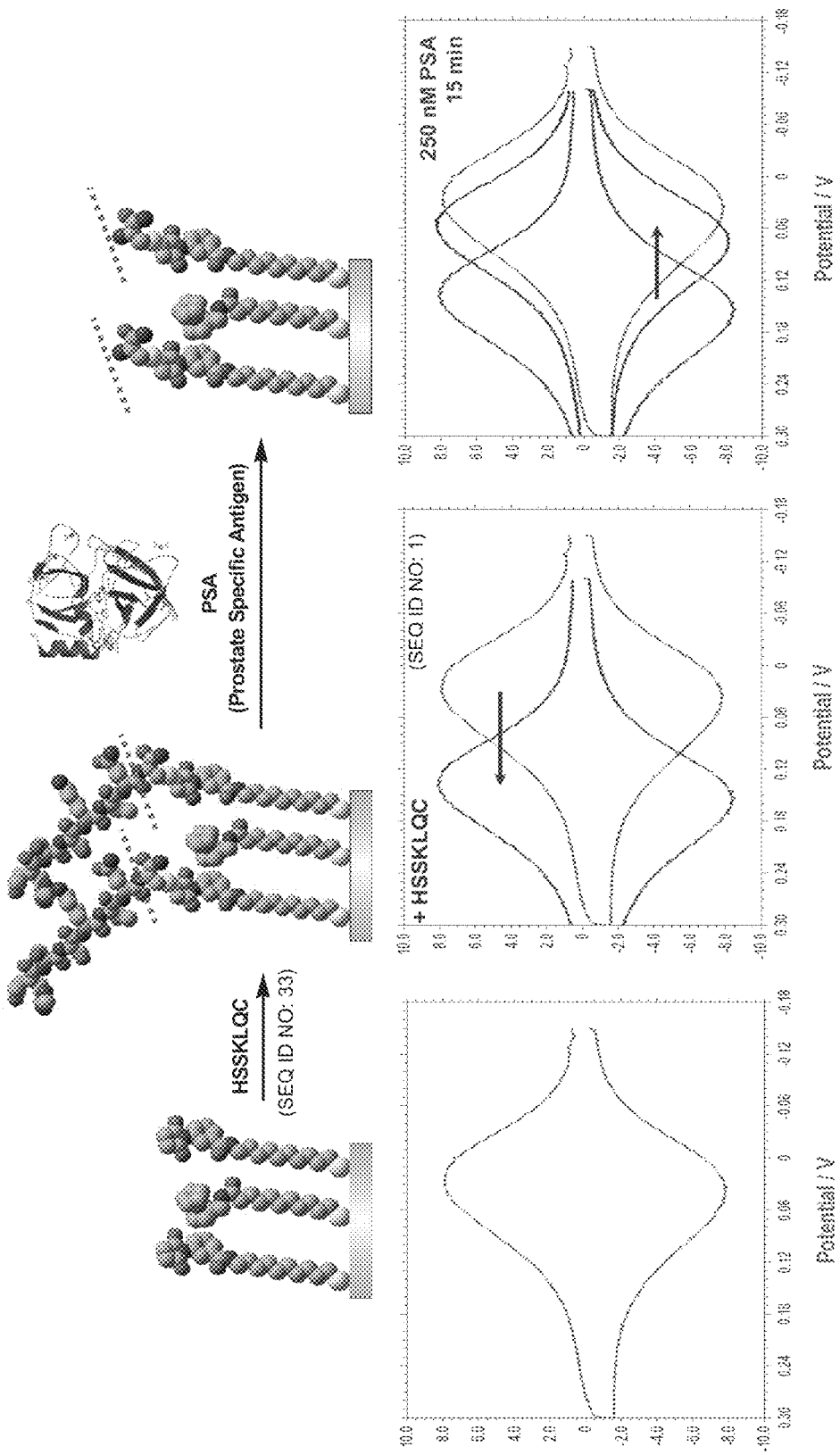
FIGS. 4A and 4B depict an exemplary embodiment for the detection of Prostate Specific Antigen (PSA) activity.
Figure 4B:
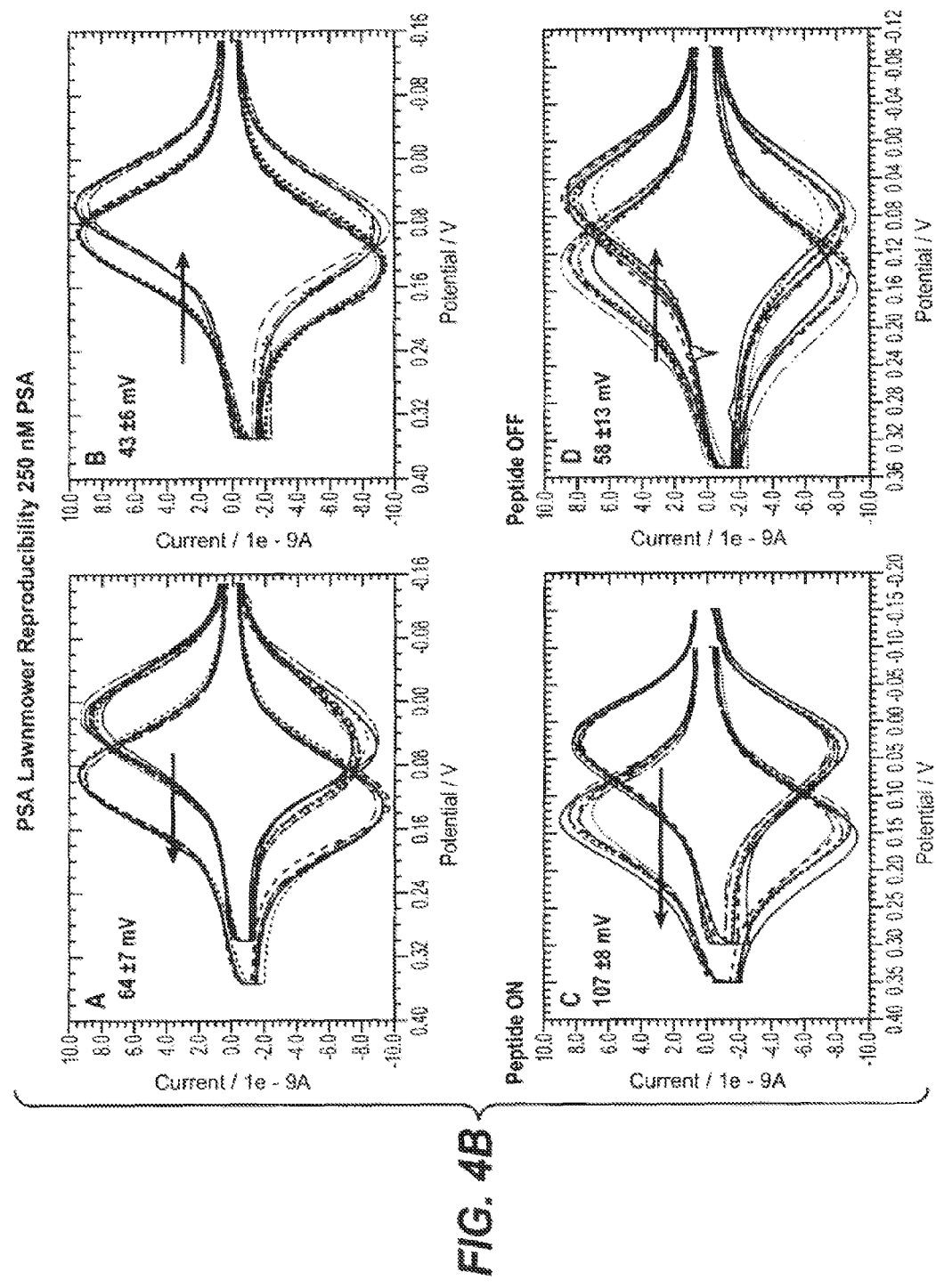
Figure 10A:
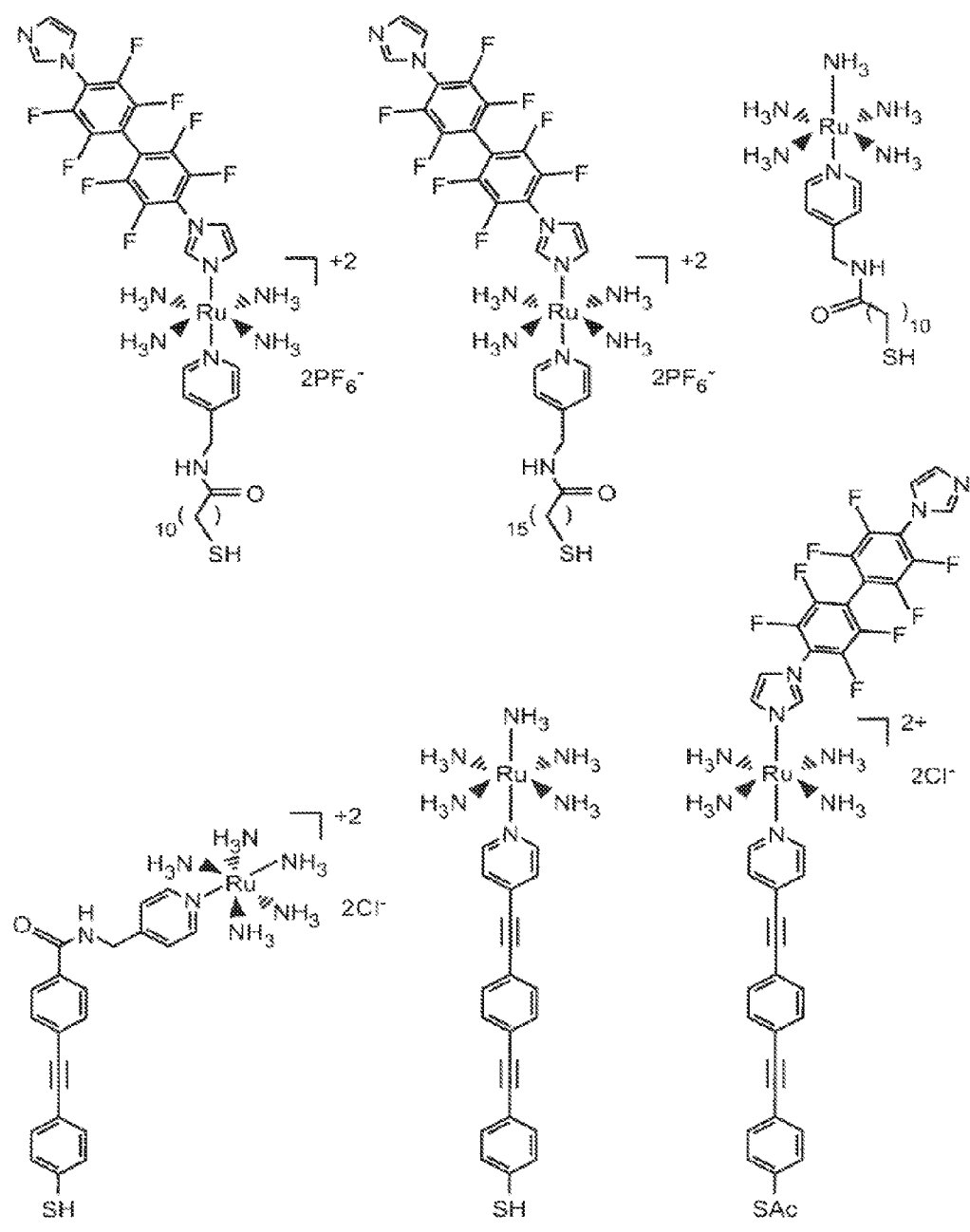
FIG. 10A depicts [BIM-Ru(NH3)4H]2+ complexes with alkylthiol anchors.
Figure 10B:
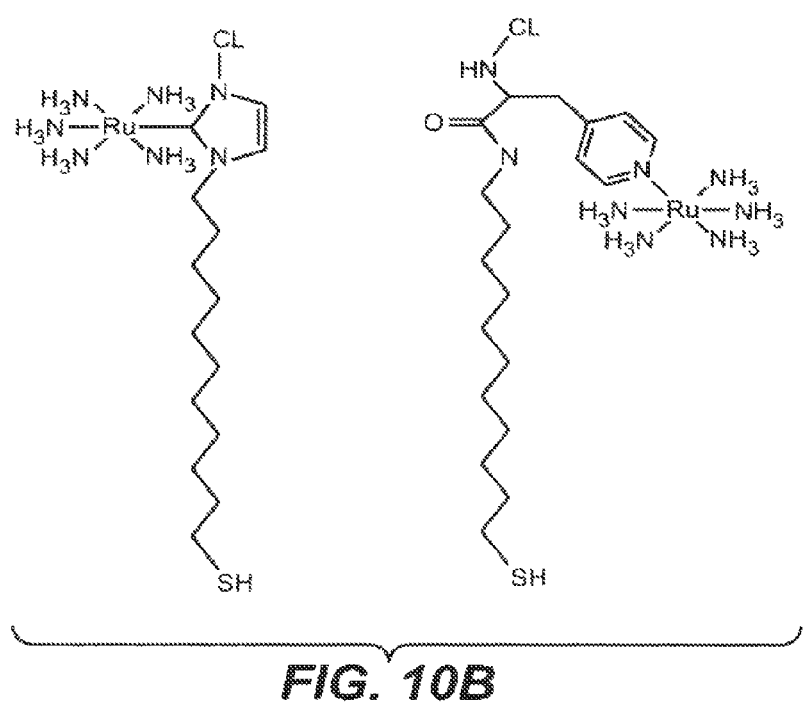
FIG. 10B depicts [Ru(NH3)5L]2+ complexes with conjugated thiol anchors.

In another aspect, the present invention provide anchor comprise conjugated thiols. Some exemplary complexes with conjugated thiol anchors are shown in FIG. 10. In some embodiments, the anchor comprises an alkylthiol group. Some of the examples are shown in FIGS. 10A and 4B. The two compounds depicts in FIG. 10B are based on carbene and 4-pyridylalanine, respectively.

In another aspect, the present invention provides conjugated multipodal thio-containing compounds that serve as anchoring groups in the construction of electroactive moieties for analyte detection on electrodes, such as gold electrodes. That is, spacer groups (which can be attached to EAMs, ReAMCs, or an "empty" monolayer forming species) are attached using two or more sulfur atoms. These mulitpodal anchor groups can be linear or cyclic, as described herein.

In some embodiments, the anchor groups are "bipodal", containing two sulfur atoms that will attach to the gold surface, and linear, although in some cases it can be possible to include systems with other multipodalities (e.g. "tripodal"). Such a multipodal anchoring group display increased stability and/or allow a greater footprint for preparing SAMs from thiol-containing anchors with sterically demanding headgroups.

In some embodiments, the anchor comprises cyclic disulfides ("bipod"). Although in some cases it can be possible to include ring system anchor groups with other multipodalities (e.g. "tripodal"). The number of the atoms of the ring can vary, for example from 5 to 10, and also includes multicyclic anchor groups, as discussed below In some embodiments, the anchor groups comprise a [1,2,5]-dithiazepane unit which is seven-membered ring with an apex nitrogen atom and a intramolecular disulfide bond as shown below:

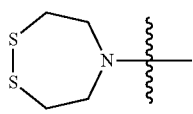

(IIIa)

In Structure (IIIa), it should also be noted that the carbon atoms of the ring can additionally be substituted. As will be appreciated by those in the art, other membered rings are also included. In addition, multicyclic ring structures can be used, which can include cyclic heteroalkanes such as the [1,2,5]-dithiazepane shown above substituted with other cyclic alkanes (including cyclic heteroalkanes) or aromatic ring structures.

In some embodiments, the anchor group and part of the spacer has the structure shown below

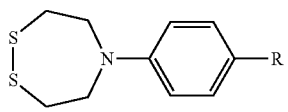

(IIIb)

The "R" group herein can be any substitution group, including a conjugated oligophenylethynylene unit with terminal coordinating ligand for the transition metal component of the EAM.

The anchors are synthesized from a bipodal intermediate (I) (the compound as formula III where R=I), which is described in Li et al., Org. Lett. 4:3631-3634 (2002), herein incorporated by reference. See also Wei et al, J. Org, Chem. 69:1461-1469 (2004), herein incorporated by reference.

The number of sulfur atoms can vary as outlined herein, with particular embodiments utilizing one, two, and three per spacer.

(c). Electroactive Moieties

In addition to anchor groups, the present invention provides compound comprising electroactive moieties. By "electroactive moiety (EAM)" or "transition metal complex" or "redox active molecule" or "electron transfer moiety (ETM)" herein is meant a metal-containing compound which is capable of reversibly or semi-reversibly transferring one or more electrons. It is to be understood that electron donor and acceptor capabilities are relative; that is, a molecule which can lose an electron under certain experimental conditions will be able to accept an electron under different experimental conditions.

It is to be understood that the number of possible transition metal complexes is very large, and that one skilled in the art of electron transfer compounds will be able to utilize a number of compounds in the present invention. By "transitional metal" herein is meant metals whose atoms have a partial or completed shell of electrons. Suitable transition metals for use in the invention include, but are not limited to, cadmium (Cd), copper (Cu), cobalt (Co), palladium (Pd), zinc (Zn), iron (Fe), ruthenium (Ru), rhodium (Rh), osmium (Os), rhenium (Re), platinium (Pt), scandium (Sc), titanium (Ti), Vanadium (V), chromium (Cr), manganese (Mn), nickel (Ni), Molybdenum (Mo), technetium (Tc), tungsten (W), and iridium (Ir). That is, the first series of transition metals, the platinum metals (Ru, Rh, Pd, Os, Ir and Pt), along with Fe, Re, W, Mo and Tc, find particular use in the present invention. Particularly preferred are metals that do not change the number of coordination sites upon a change in oxidation state, including ruthenium, osmium, iron, platinum and palladium, with osmium, ruthenium and iron being especially preferred, and osmium finding particular use in many embodiments. In some embodiments, iron is not preferred. Generally, transition metals are depicted herein as TM or M.

The transitional metal and the coordinating ligands form a metal complex. By "ligand" or "coordinating ligand" (depicted herein in the figures as "L") herein is meant an atom, ion, molecule, or functional group that generally donates one or more of its electrons through a coordinate covalent bond to, or shares its electrons through a covalent bond with, one or more central atoms or ions.

The other coordination sites of the metal are used for attachment of the transition metal complex to either a capture ligand (directly or indirectly using a linker), or to the electrode (frequently using a spacer, as is more fully described below), or both. Thus for example, when the transition metal complex is directly joined to a binding ligand, one, two or more of the coordination sites of the metal ion may be occupied by coordination atoms supplied by the binding ligand (or by the linker, if indirectly joined). In addition, or alternatively, one or more of the coordination sites of the metal ion may be occupied by a spacer used to attach the transition metal complex to the electrode. For example, when the transition metal complex is attached to the electrode separately from the binding ligand as is more fully described below, all of the coordination sites of the metal (n) except 1 (n−1) may contain polar ligands.

Suitable small polar ligands, generally depicted herein as "L", fall into two general categories, as is more fully described herein. In one embodiment, the small polar ligands will be effectively irreversibly bound to the metal ion, due to their characteristics as generally poor leaving groups or as good sigma donors, and the identity of the metal. These ligands may be referred to as "substitutionally inert". Alternatively, as is more fully described below, the small polar ligands may be reversibly bound to the metal ion, such that upon binding of a target analyte, the analyte may provide one or more coordination atoms for the metal, effectively replacing the small polar ligands, due to their good leaving group properties or poor sigma donor properties. These ligands may be referred to as "substitutionally labile". The ligands preferably form dipoles, since this will contribute to a high solvent reorganization energy.

Some of the structures of transitional metal complexes are shown below:

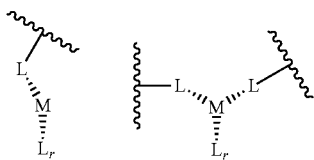

L are the co-ligands, that provide the coordination atoms for the binding of the metal ion. As will be appreciated by those in the art, the number and nature of the co-ligands will depend on the coordination number of the metal ion. Mono-, di- or polydentate co-ligands may be used at any position. Thus, for example, when the metal has a coordination number of six, the L from the terminus of the conductive oligomer, the L contributed from the nucleic acid, and r, add up to six. Thus, when the metal has a coordination number of six, r may range from zero (when all coordination atoms are provided by the other two ligands) to four, when all the co-ligands are monodentate. Thus generally, r will be from 0 to 8, depending on the coordination number of the metal ion and the choice of the other ligands.

In one embodiment, the metal ion has a coordination number of six and both the ligand attached to the conductive oligomer and the ligand attached to the nucleic acid are at least bidentate; that is, r is preferably zero, one (i.e. the remaining co-ligand is bidentate) or two (two monodentate co-ligands are used).

As will be appreciated in the art, the co-ligands can be the same or different. Suitable ligands fall into two categories: ligands which use nitrogen, oxygen, sulfur, carbon or phosphorus atoms (depending on the metal ion) as the coordination atoms (generally referred to in the literature as sigma (σ) donors) and organometallic ligands such as metallocene ligands (generally referred to in the literature as pi (π) donors, and depicted herein as Lm). Suitable nitrogen donating ligands are well known in the art and include, but are not limited to, cyano (C≡N), NH2; NHR; NRR; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetra-azacyclotetradecane (abbreviated cyclam) and isocyanide. Substituted derivatives, including fused derivatives, may also be used. In some embodiments, porphyrins and substituted derivatives of the porphyrin family may be used. See for example, Comprehensive Coordination Chemistry, Ed. Wilkinson et al., Pergammon Press, 1987, Chapters 13.2 (pp 73-98), 21.1 (pp. 813-898) and 21.3 (pp 915-957), all of which are hereby expressly incorporated by reference.

As will be appreciated in the art, any ligand donor(1)-bridge-donor(2) where donor (1) binds to the metal and donor (2) is available for interaction with the surrounding medium (solvent, protein, etc) can be used in the present invention, especially if donor(1) and donor(2) are coupled through a pi system, as in cyanos (C is donor(1), N is donor(2), pi system is the CN triple bond). One example is bipyrimidine, which looks much like bipyridine but has N donors on the "back side" for interactions with the medium. Additional co-ligands include, but are not limited to cyanates, isocyanates (—N=C=O), thiocyanates, isonitrile, N2, O2, carbonyl, halides, alkoxyide, thiolates, amides, phosphides, and sulfur containing compound such as sulfino, sulfonyl, sulfoamino, and sulfamoyl.

In some embodiments, multiple cyanos are used as co-ligand to complex with different metals. For example, seven cyanos bind Re(III); eight bind Mo(IV) and W(IV). Thus at Re(III) with 6 or less cyanos and one or more L, or Mo(IV) or W(IV) with 7 or less cyanos and one or more L can be used in the present invention. The EAM with W(IV) system has particular advantages over the others because it is more inert, easier to prepare, more favorable reduction potential. Generally that a larger CN/L ratio will give larger shifts.

Suitable sigma donating ligands using carbon, oxygen, sulfur and phosphorus are known in the art. For example, suitable sigma carbon donors are found in Cotton and Wilkenson, Advanced Organic Chemistry, 5th Edition, John Wiley & Sons, 1988, hereby incorporated by reference; see page 38, for example. Similarly, suitable oxygen ligands include crown ethers, water and others known in the art. Phosphines and substituted phosphines are also suitable; see page 38 of Cotton and Wilkenson.

The oxygen, sulfur, phosphorus and nitrogen-donating ligands are attached in such a manner as to allow the heteroatoms to serve as coordination atoms.

In some embodiments, organometallic ligands are used. In addition to purely organic compounds for use as redox moieties, and various transition metal coordination complexes with σ-bonded organic ligand with donor atoms as heterocyclic or exocyclic substituents, there is available a wide variety of transition metal organometallic compounds with .pi.-bonded organic ligands (see Advanced Inorganic Chemistry, 5th Ed., Cotton & Wilkinson, John Wiley & Sons, 1988, chapter 26; Organometallics, A Concise Introduction, Elschenbroich et al., 2nd Ed., 1992, VCH; and Comprehensive Organometallic Chemistry II, A Review of the Literature 1982-1994, Abel et al. Ed., Vol. 7, chapters 7, 8, 10 & 11, Pergamon Press, hereby expressly incorporated by reference). Such organometallic ligands include cyclic aromatic compounds such as the cyclopentadienide ion [C5H5 (−1)] and various ring substituted and ring fused derivatives, such as the indenylide (−1) ion, that yield a class of bis(cyclopentadieyl)metal compounds, (i.e. the metallocenes); see for example Robins et al., J. Am. Chem. Soc. 104:1882-1893 (1982); and Gassman et al., J. Am. Chem. Soc. 108:4228-4229 (1986), incorporated by reference. Of these, ferrocene [(C5H5)2Fe] and its derivatives are prototypical examples which have been used in a wide variety of chemical (Connelly et al., Chem. Rev. 96:877-910 (1996), incorporated by reference) and electrochemical (Geiger et al., Advances in Organometallic Chemistry 23:1-93; and Geiger et al., Advances in Organometallic Chemistry 24:87, incorporated by reference) electron transfer or "redox" reactions. Metallocene derivatives of a variety of the first, second and third row transition metals are potential candidates as redox moieties that are covalently attached to either the ribose ring or the nucleoside base of nucleic acid. Other potentially suitable organometallic ligands include cyclic arenes such as benzene, to yield bis(arene)metal compounds and their ring substituted and ring fused derivatives, of which bis(benzene)chromium is a prototypical example. Other acyclic π-bonded ligands such as the allyl(−1) ion, or butadiene yield potentially suitable organometallic compounds, and all such ligands, in conduction with other .pi.-bonded and .delta.-bonded ligands constitute the general class of organometallic compounds in which there is a metal to carbon bond. Electrochemical studies of various dimers and oligomers of such compounds with bridging organic ligands, and additional non-bridging ligands, as well as with and without metal-metal bonds are potential candidate redox moieties in nucleic acid analysis.

When one or more of the co-ligands is an organometallic ligand, the ligand is generally attached via one of the carbon atoms of the organometallic ligand, although attachment may be via other atoms for heterocyclic ligands. Preferred organometallic ligands include metallocene ligands, including substituted derivatives and the metalloceneophanes (see page 1174 of Cotton and Wilkenson, supra). For example, derivatives of metallocene ligands such as methylcyclopentadienyl, with multiple methyl groups being preferred, such as pentamethylcyclopentadienyl, can be used to increase the stability of the metallocene. In a preferred embodiment, only one of the two metallocene ligands of a metallocene are derivatized.

As described herein, any combination of ligands may be used. Preferred combinations include: a) all ligands are nitrogen donating ligands; b) all ligands are organometallic ligands; and c) the ligand at the terminus of the conductive oligomer is a metallocene ligand and the ligand provided by the nucleic acid is a nitrogen donating ligand, with the other ligands, if needed, are either nitrogen donating ligands or metallocene ligands, or a mixture.

As a general rule, EAM comprising non-macrocyclic chelators are bound to metal ions to form non-macrocyclic chelate compounds, since the presence of the metal allows for multiple proligands to bind together to give multiple oxidation states.

In some embodiments, nitrogen donating proligands are used. Suitable nitrogen donating proligands are well known in the art and include, but are not limited to, NH2; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetra-azacyclotetradecane (abbreviated cyclam) and isocyanide. Substituted derivatives, including fused derivatives, may also be used. It should be noted that macrocyclic ligands that do not coordinatively saturate the metal ion, and which require the addition of another proligand, are considered non-macrocyclic for this purpose. As will be appreciated by those in the art, it is possible to covalent attach a number of "non-macrocyclic" ligands to form a coordinatively saturated compound, but that is lacking a cyclic skeleton.

In some embodiments, a mixture of monodentate (e.g. at least one cyano ligand), bi-dentate, tri-dentate, and polydentate ligands (till to saturate) can be used in the construction of EAMs Generally, it is the composition or characteristics of the ligands that determine whether a transition metal complex is solvent accessible. By "solvent accessible transition metal complex" or grammatical equivalents herein is meant a transition metal complex that has at least one, preferably two, and more preferably three, four or more small polar ligands. The actual number of polar ligands will depend on the coordination number (n) of the metal ion. Preferred numbers of polar ligands are (n−1) and (n−2). For example, for hexacoordinate metals, such as Fe, Ru, and Os, solvent accessible transition metal complexes preferably have one to five small polar ligands, with two to five being preferred, and three to five being particularly preferred, depending on the requirement for the other sites, as is more fully described below. Tetracoordinate metals such as Pt and Pd preferably have one, two or three small polar ligands.

It should be understood that "solvent accessible" and "solvent inhibited" are relative terms. That is, at high applied energy, even a solvent accessible transition metal complex may be induced to transfer an electron.

Some examples of EAMs are described herein.

1). Cyano-Based Complexes

In one aspect, the present invention provides EAMs with a transition metal and at least one cyano (—C≡N) ligand. Depending on the valency of the metal and the configuration of the system (e.g. capture ligand contributing a coordination atom, etc.), 1, 2, 3, 4 or 5 cyano ligands can be used. In general, embodiments which use the most cyano ligands are preferred; again, this depends on the configuration of the system. For example, as depicted in FIG. 7, an EAM using a hexadentate metal such as osmium, separately attached from the capture ligand, allows 5 cyano ligands, with the 6th coordination site being occupied by the terminus of the attachment linker. When a hexadentate metal has both an attachment linker and a capture ligand providing coordination atoms, there can be four cyano ligands.

Figure 11:
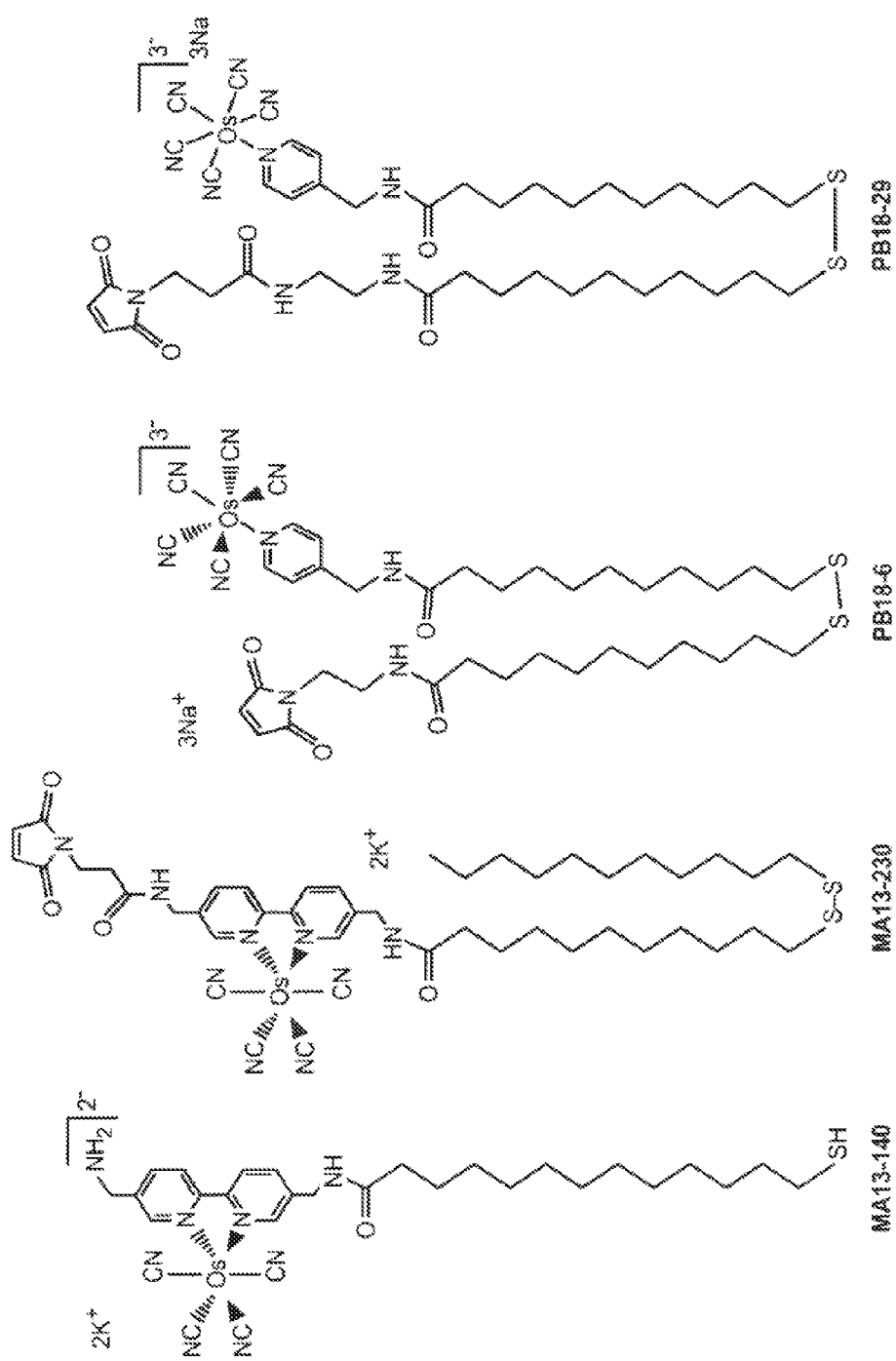
FIG. 11 depicts Osmium-based EAMs.

In some embodiments, such as depicted in the FIGS. 7-9, the attachment linker and/or the capture ligand can provide more than a single coordination atom. Thus, for example, in FIG. 11, the attachment linker comprises a bipyridine which contributes two coordination atoms.

In some embodiments, ligands other than cyano ligands are used in combination with at least one cyano ligand.

2). Ru—N Based Complexes

Figure 12A:
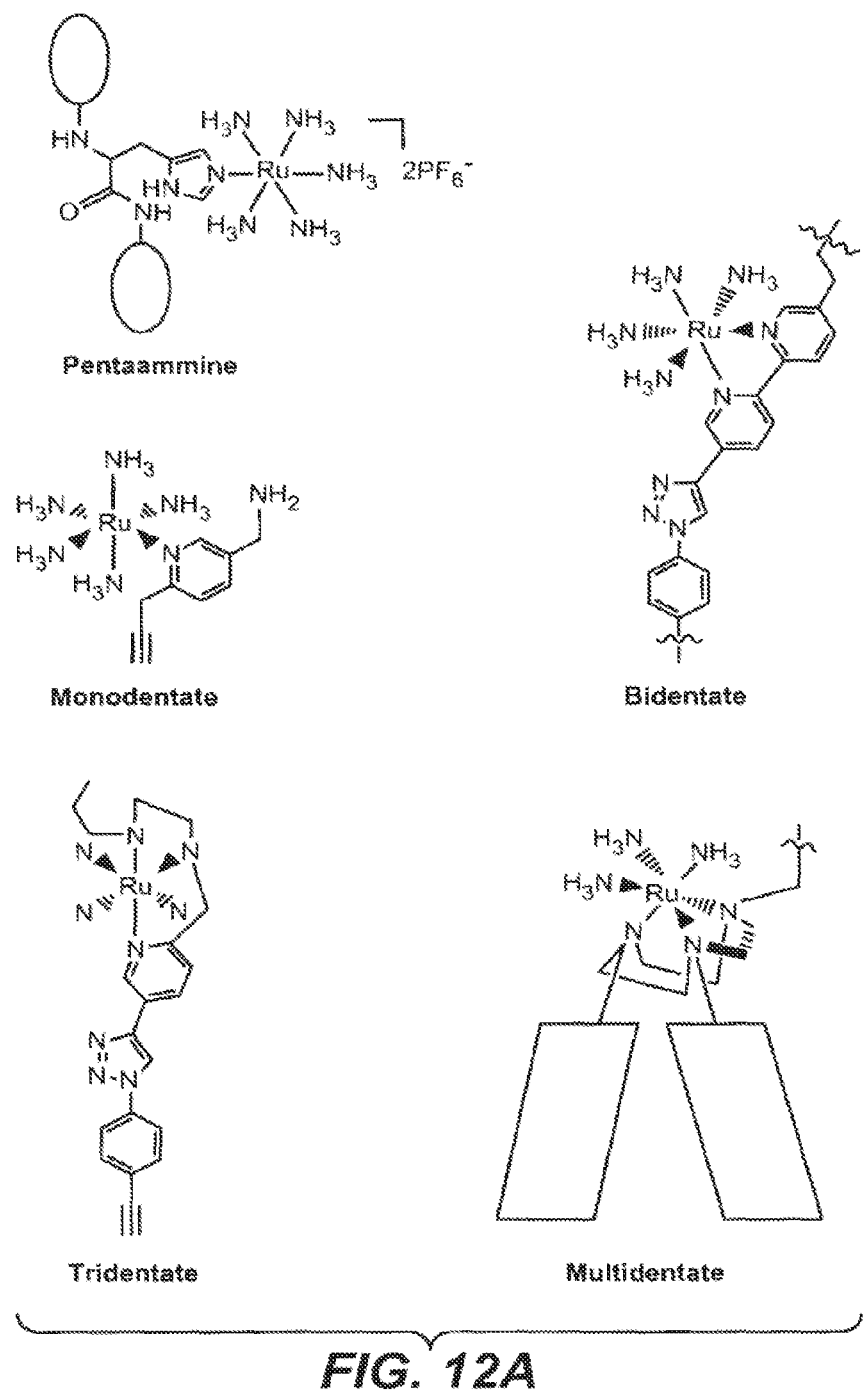
FIG. 12A depicts new architectures for Ru—N based complexes.
Figure 12B:
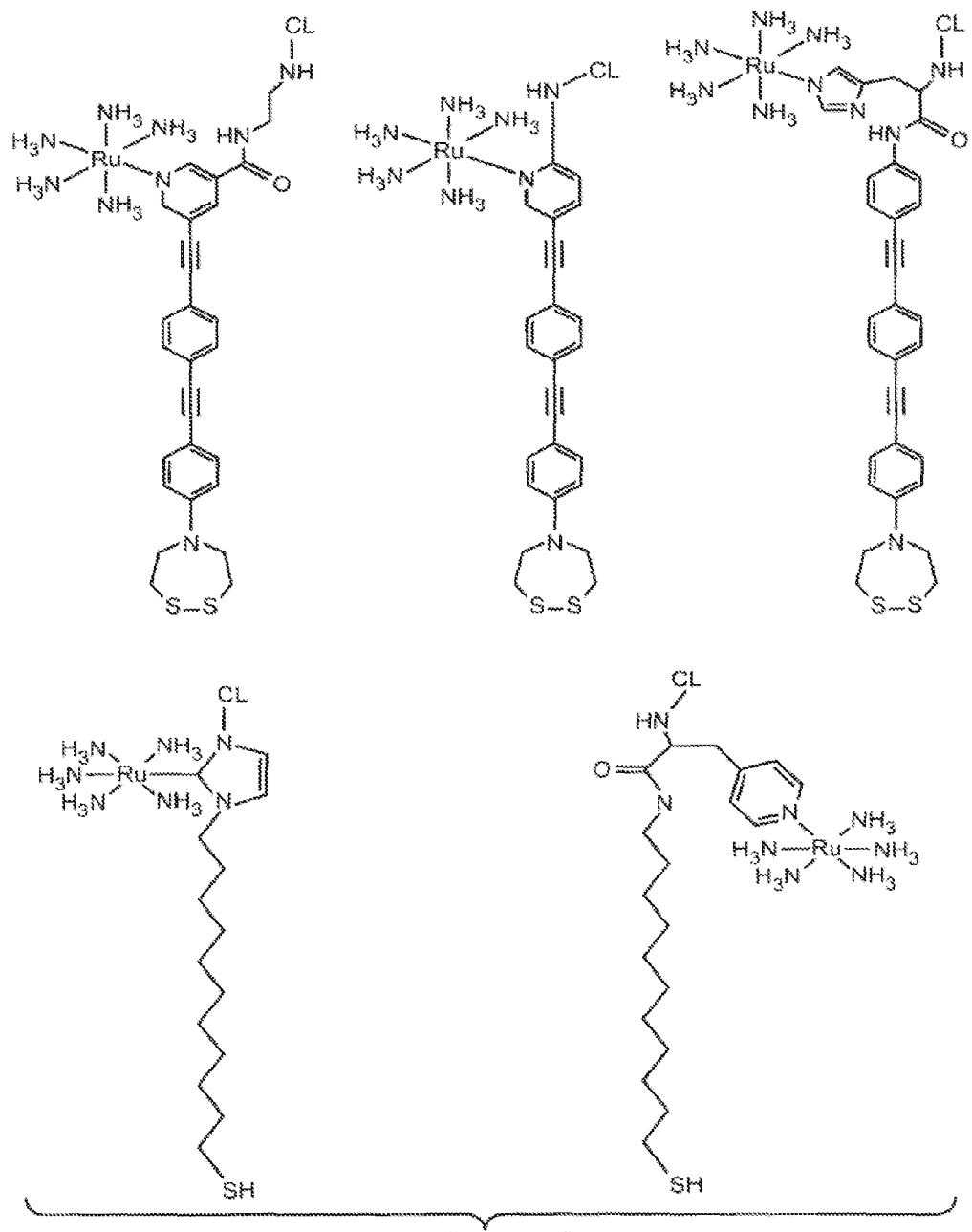
FIG. 12B depicts examples of Ru—N based complexes.

In one aspect, the resent invention provides new architectures for Ru—N based complexes, where the coordination could be monodentate, bidentate, tridentate, or multidendate. Thus the number of coordination ligand L (which covalently connected to the anchor and capture ligand) can be 1, 2, 3, or 4. Some of the examples are shown in FIG. 12A.

The charge-neutralizing ligands can be any suitable ligand known in the art, such as dithiocarbamate, benzenedithiolate, or Schiff base as described herein. The capture ligand and the anchor can be on the same framework or separate.

Figure 5:
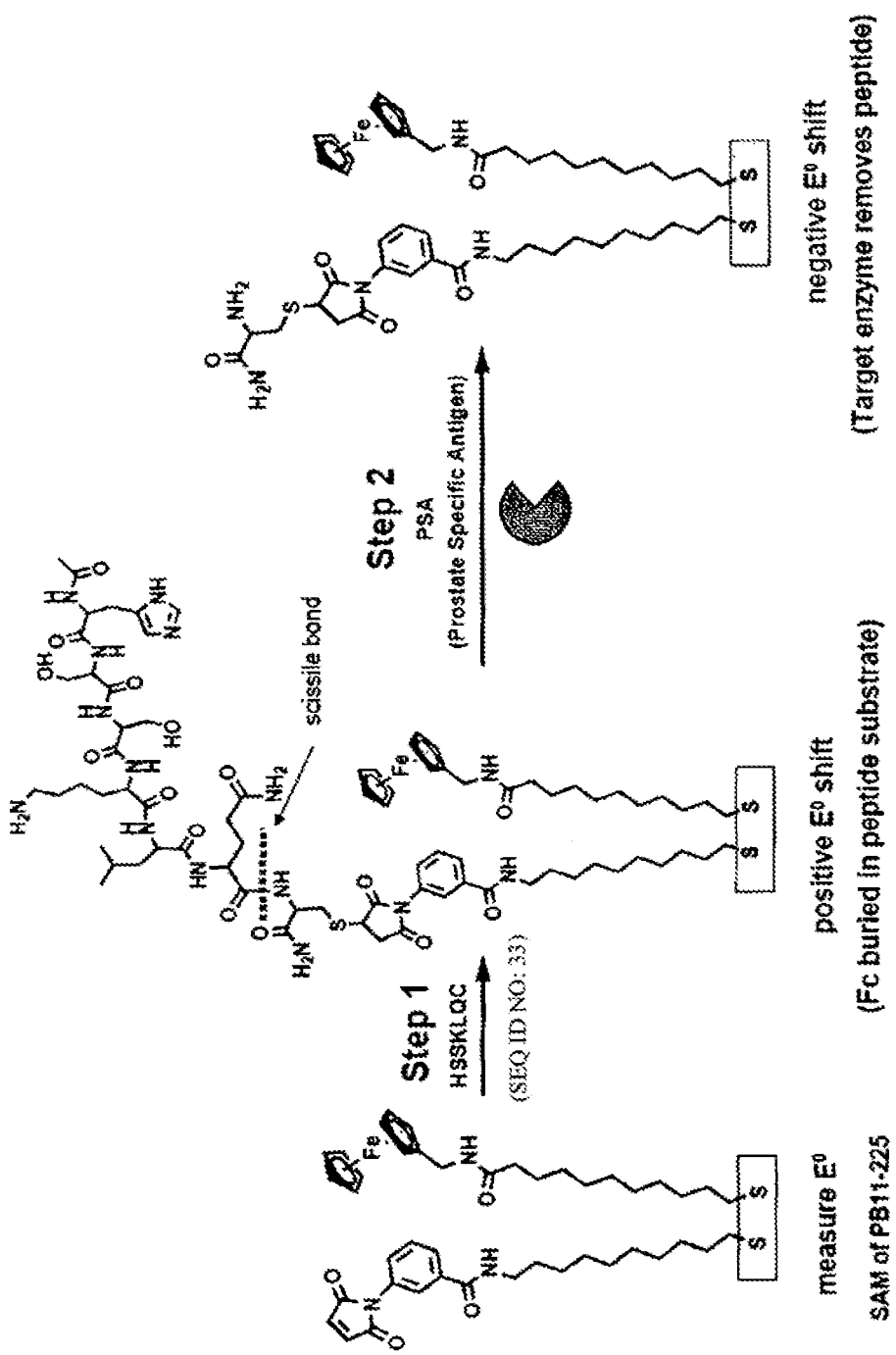
FIG. 5 depicts the structure of an EMA used in one of the exemplary PSA assay.
Figure 6:
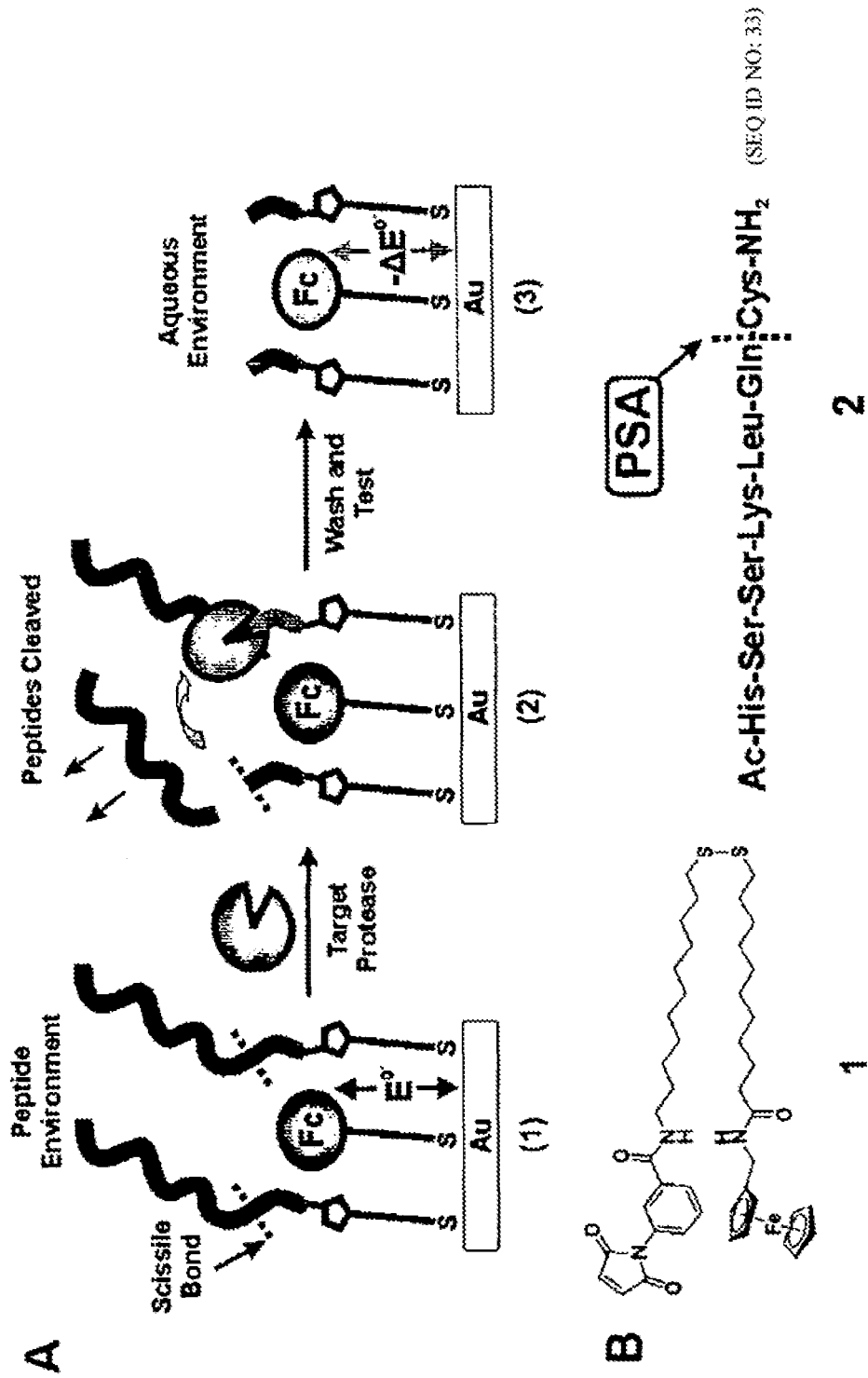
FIG. 6A is a schematic diagram of the electrochemical biosensor platform for detecting protease activity. Steps include: (1) measuring the $E^0$ of ferrocene buried in neighboring protease-removable peptide substrates in a SAM, (2) incubation with target protease which recognizes and cleaves the immobilized peptides, (3) removal of the cleaved peptides by washing, exposing the ferrocene probe to a more aqueous environment causing a negative shift in $E^0$.
FIG. 6B depicts Structure of 1 and the peptide sequence 2 used to transduce the activity of PSA.

In another aspect of the present invention, each component of the EAM ligand architecture is connected through covalent bonds rather than Ru coordination chemistry. The construction of the architectures provide herein relies on modern synthetic organic chemical methodology. An important design consideration includes the necessary orthogonal reactivity of the functional groups present in the anchor and capture ligand component versus the coordinating ligand component. Preferably, the entire compound can be synthesized and the redox active transitional metal coordinated to the ligand near the last step of the synthesis. The coordinating ligands provided herein rely on well-established inorganic methodologies for ruthenium pentaamine precursors. See Gerhardt and Weck, J. Org. Chem. 71:6336-6341 (2006); Sizova et al., Inorg. Chim. Acta, 357:354-360 (2004); and Scott and Nolan, Eur. J. Inorg. Chem. 1815-1828 (2005), all herein incorporated by reference. Some examples of EAM architectures with Ru-pentaamine complexes are shown below in FIG. 5B.

As can be understood by those skilled in the art, the anchor components of the compounds provided herein could be interchanged between alkyl and multipodal-based thiols.

3). Ferrocene-Based EAMs

In some embodiments, the EAMs comprise substituted ferrocenes. Ferrocene is air-stable. It can be easily substituted with both capture ligand and anchoring group. Upon binding of the target protein to the capture ligand on the ferrocene which will not only change the environment around the ferrocene, but also prevent the cyclopentadienyl rings from spinning, which will change the energy by approximately 4kJ/mol. WO/1998/57159; Heinze and Schlenker, Eur. J. Inorg. Chem. 2974-2988 (2004); Heinze and Schlenker, Eur. J. Inorg. Chem. 66-71 (2005); and Holleman-Wiberg, Inorganic Chemistry, Academic Press 34th Ed, at 1620, all incorporated by reference.

In some embodiments, the following restraints are desirable: the metal complex should have small polar ligands that allow close contact with the solvent.

4). Charge-Neutralizing Ligands

In another aspect, the present invention provides compositions having metal complexes comprising charged ligands. The reorganization energy for a system that changes from neutral to charged (e.g. M+<−>M0; M−<−>M0) may be larger than that for a system in which the charge simply changes (e.g. M2+<−>M3+) because the water molecules have to "reorganize" more to accommodate the change to or from an unpolarized environment.

In some embodiments, charged ligand anionic compounds can be used to attach the anchor and the capture ligand to the metal center. A metal complex containing a halide ion X in the inner complex sphere reacts with charged ligands, include but not limited to, thiols (R—SH), thiolates (RS-E; E=leaving group, i.e., trimethylsilyl-group), carbonic acids, dithiois, carbonates, acetylacetonates, salicylates, cysteine, 3-mercapto-2-(mercaptomethyl) propanoic acid. The driving force for this reaction is the formation of HX or EX. If the anionic ligand contains both capture ligand and anchor, one substitu-

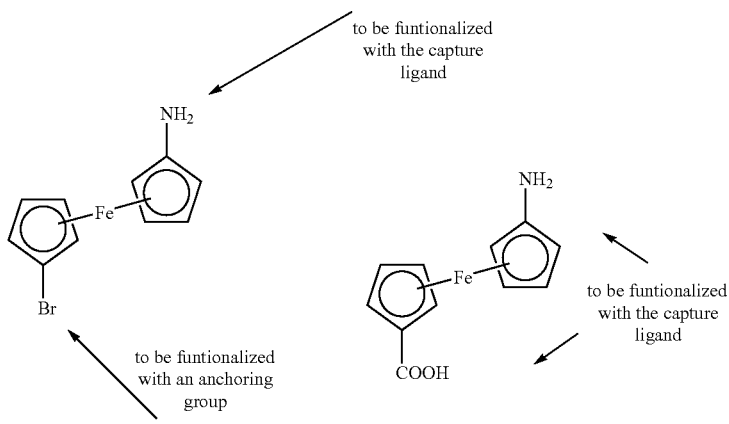

In some embodiments the anchor and capture ligands are attached to the same ligand for easier synthesis. In some embodiments the anchor and capture ligand are attached to different ligands.

There are many ligands that can be used to build the new architecture disclosed herein. They include but not limited to carboxylate, amine, thiolate, phosphine, imidazole, pyridine, bipyridine, terpyridine, tacn (1,4,7-Triazacyclononane), salen (N,N'-bis(salicylidene) ethylenediamine), acacen (N,N'-Ethylenebis(acetylacetoniminate(−)), EDTA (ethylenediamine tetraacetic acid), DTPA (diethylene triamine pentaacetic acid), Cp (cyclopentadienyl), pincer ligands, and scorpionates. In some embodiments, the preferred ligand is pentaamine.

Pincer ligands are a specific type of chelating ligand. A pincer ligand wraps itself around the metal center to create bonds on opposite sides of the metal as well as one in between. The effects pincer ligand chemistry on the metal core electrons is similar to amines, phosphines, and mixed donor ligands. This creates a unique chemical situation where the activity of the metal can be tailored. For example, since there is such a high demand on the sterics of the complex in order to accommodate a pincer ligand, the reactions that the metal can participate in is limited and selective.

Scorpionate ligand refers to a tridentate ligand which would bind to a metal in a fac manner. The most popular class of scorpionates are the tris(pyrazolyl)hydroborates or Tp ligands. A Cp ligand is isolobal to Tp tion reaction is required, and therefore the metal complex, with which it is reacted, needs to have one halide ligand in the inner sphere. If the anchor and capture ligand are introduced separately the starting material generally needs to contain two halide in the inner coordination sphere. Seidel et al., Inorg. Chem 37:6587-6596 (1998); Kathari and Busch, Inorga. Chem. 8:2276-2280 (1978); Isied and Kuehn J. Am. Chem. Soc. 100:6752-6754; and Voikers et al., Eur. J. Inorg. Chem. 4793-4799 (2006), all herein incorporated by reference.

Examples for suitable metal complexes are the following (it should be noted that the structures depicted below show multiple unidentate ligands, and muitidentate ligands can be substituted for or combined with unidentate ligands such as cyano ligands):

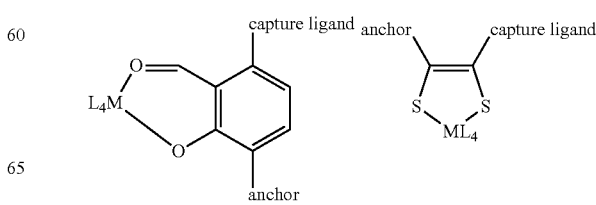

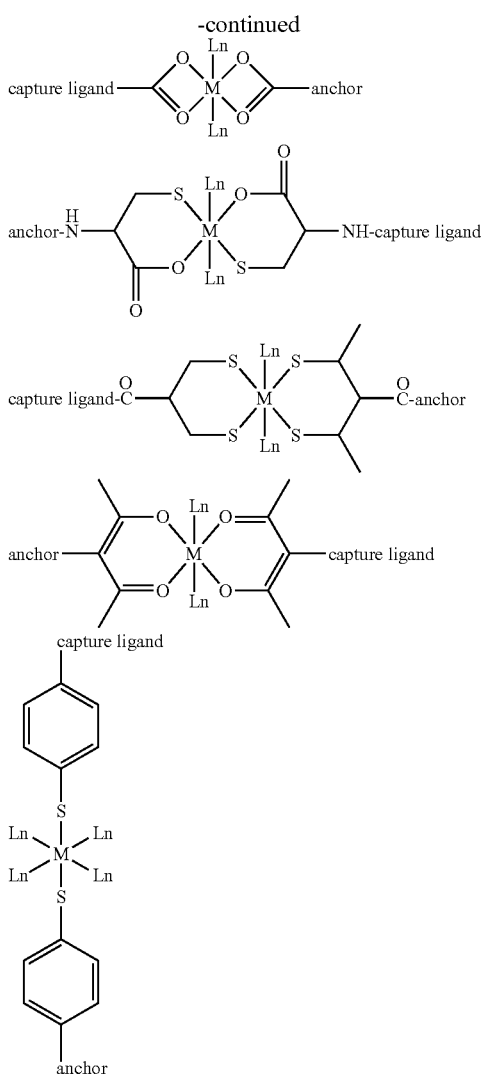

In some embodiments, dithiocarbamate is used as a charge-neutralizing ligand, such as the following example:

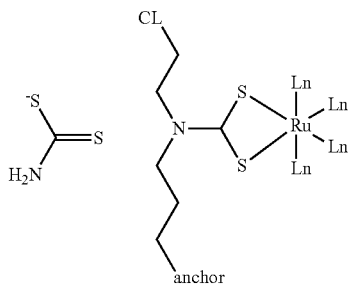

In some embodiments, benzenedithiolate is used as charge-neutralizing ligand, such as the following example:

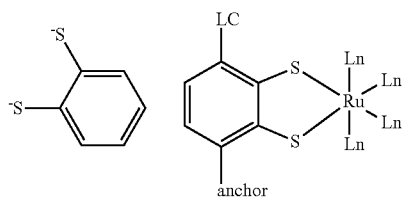

In the above depicted structures, Ln is coordinate ligand and n=0 or 1.

In some embodiments, the EAM comprises Schiff base type complexes. By "Schiff base" or "azomethine" herein is meant a functional group that contains a carbon-nitrogen double bond with the nitrogen atom connected to an aryl or alkyl group—but not hydrogen. Schiff bases are of the general formula R1R2C=N—R3, where R3 is a phenyl or alkyl group that makes the Schiff base a stable imine. Schiff bases can be synthesized from an aromatic amine and a carbonyl compound by nucleophilic addition forming a hemiaminal, followed by a dehydration to generate an imine.

Acacen is a small planar tetradentate ligand that can form hydrogen bonds to surrounding water molecules trough its nitrogen and oxygen atoms, which would enhance the reorganization energy effect. It can be modified with many functionalities, include but not limited to, carboxylic acid and halides, which can be used to couple the acacen-ligand to the capture ligand and to the anchoring group. This system allows a large variety of different metal centers to be utilized in the EAMs. Since the ligand binds with its two oxygen and two nitrogen atoms, only four coordination sites are occupied. This leaves two additional coordination sites open, depending on the metal center. These coordination sites can be occupied by a large variety of organic and inorganic ligands. These additional open sites can be used for inner-sphere substitution (e.g. labile H2O or NH3 can be displaced by protein binding) or outer-sphere influence (e.g. CO, CN can for H-bonds) to optimize the shift of potentials upon binding of the capture ligand to the target. WO/1998/057158, WO/1997/21431, Louie et al., PNAS 95:6663-6668 (1999), and Bottcher et al., Inorg. Chem. 36:2498-2504 (1997), herein all incorporated by references.

In some embodiments, salen-complexes are used as well. Syamal et al., Reactive and Functional Polymers 39:27-35 (1999).

The structures of some acacen-based complexes and salen-based complexes are shown below, where positions on the ligand that are suitable for functionalization with the capture ligand and/or the anchor are marked with an asterisk.

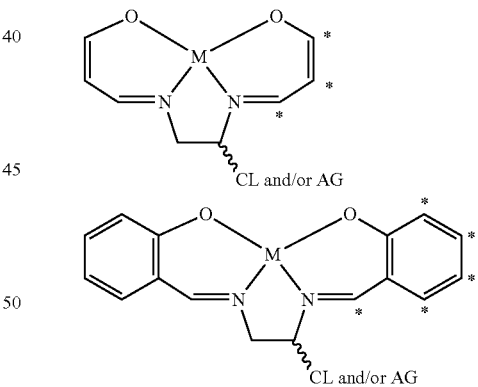

One example of using acacen as ligand to form a cobalt complex is the following:

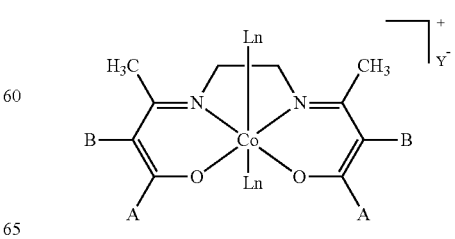

wherein is A and B are substitute groups, Ln is coordinating ligand and n=0 or 1.

5). Sulfato Ligands

In some embodiments, the EAM comprises sulfato complexes, include but not limited to, [L-Ru(III)(NH3)4SO4]+ and [L-Ru(III)(NH3)4SO22]2+. The SO4-Ru(III)-complexes are air stable. The ligand L comprises a capture ligand an anchor. The sulfate ligand is more polar than amine and negatively charged. The surface complexes therefore will be surrounded by a large number of water molecules than both the [L-Ru(NH3)5-L'] and [L-Ru(NH3)5]2+. Isied and Taube, Inorg. Chem. 13:1545-1551 (1974), herein incorporated by reference.

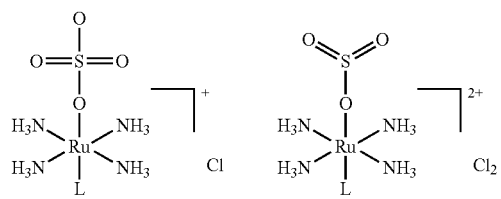

(d). Spacer Groups

In some embodiments, the EAM or ReAMC is covalently attached to the anchor group (which is attached to the electrode) via an attachment linker or spacer ("Spacer 1"), that further generally includes a functional moiety that allows the association of the attachment linker to the electrode. See for example U.S. Pat. No. 7,384,749, incorporated herein by reference in its entirety and specifically for the discussion of attachment linkers). It should be noted in the case of a gold electrode, a sulfur atom can be used as the functional group (this attachment is considered covalent for the purposes of this invention). By "spacer" or "attachment linker" herein is meant a moiety which holds the redox active complex off the surface of the electrode. In some embodiments, the spacer is a conductive oligomer as outlined herein, although suitable spacer moieties include passivation agents and insulators as outlined below. In some cases, the spacer molecules are SAM forming species. The spacer moieties may be substantially non-conductive, although preferably (but not required) is that the electron coupling between the redox active molecule and the electrode (HAB) does not become the rate limiting step in electron transfer.

In addition, attachment linkers can be used to between the coordination atom of the capture ligand and the capture ligand itself, in the case when ReAMCs are utilized. Similarly, attachment linkers can be branched, such as shown in FIGS. 7-9. In addition, attachment linkers can be used to attach capture ligands to the electrode when they are not associated in a ReAMC.

One end of the attachment linker is linked to the EAM/ReAMC/capture ligand, and the other end (although as will be appreciated by those in the art, it need not be the exact terminus for either) is attached to the electrode.

The covalent attachment of the conductive oligomer containing the redox active molecule (and the attachment of other spacer molecules) may be accomplished in a variety of ways, depending on the electrode and the conductive oligomer used. See for example Structures 12-19 and the accompanying text in U.S. Patent Publication No. 20020009810, hereby incorporated by reference in its entirety.

In general, the length of the spacer is as outlined for conductive polymers and passivation agents in U.S. Pat. Nos. 6,013,459, 6,013,170, and 6,248,229, as well as 7,384,749 all herein incorporated by reference in their entireties. As will be appreciated by those in the art, if the spacer becomes too long, the electronic coupling between the redox active molecule and the electrode will decrease rapidly.

II. Method of Making

In another aspect, the present invention provides method of making the compositions as described herein. In some embodiments, the composition are made according to methods disclosed in of U.S. Pat. Nos. 6,013,459, 6,248,229, 7,018,523, 7,267,939, U.S. patent application Ser. Nos. 09/096,593 and 60/980,733, and U.S. Provisional Application No. 61/087,102, filed on Aug. 7, 2008, all are herein incorporated in their entireties for all purposes.

In one embodiments, Compound I (an unsymmetric dialkyl disulfide bearing terminal ferrocene and maleimide groups) as shown below was synthesized and deposited on gold electrodes as described in more detail in the Examples.

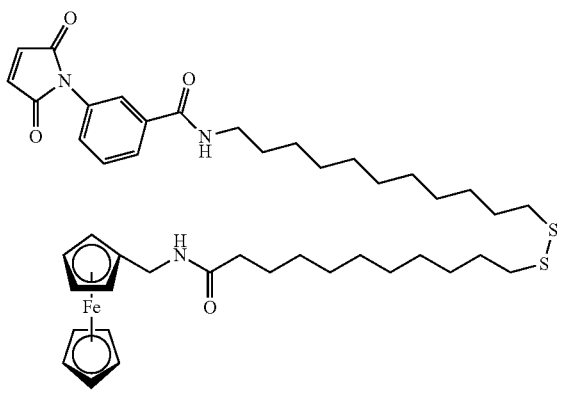

1

III. Methods of Detecting Target Enzymes

Reorganization energy has been explored to develop methods for detecting analytes.

1). Overview

In one aspect, the present invention provides methods for detection of a target enzyme that involves a catalysis (chemical) event—cleaving or transferring of substrate, rather than a binding/dissociation (physical) event, thus producing an amplification effect. In some embodiments, the target analyte may be an enzyme. Upon introduction of the target enzyme, the enzyme associates with the substrate to cleave or otherwise sterically alter the substrate such that the redox active molecule is made solvent accessible. This change can then be detected. This embodiment is advantageous in that it results in an amplification of the signal, since a single enzyme molecule can result in multiple solvent accessible molecules. This may find particular use in the detection of bacteria or other pathogens that secrete enzymes, particularly scavenger proteases or carbohydrases.

2). Sample

In one aspect, the present invention provides a method of detecting a target enzyme in a sample. By "sample" or "test sample" herein is meant a composition that contains the analyte or analytes to be detected. The sample can be heterogeneous, containing a variety of components, i.e. different proteins. Alternatively, the sample can be homogenous, containing one component. The sample can be naturally occurring, a biological material, or man-made material. The material can be in a native or denatured form. The sample can be a single cell or a plurality of cells, a blood sample, a tissue sample, a skin sample, a urine sample, a water sample, or a soil sample. In some embodiments, the sample comprises the contents of a single cell, or the contents of a plurality of cells. The sample can be from a living organism, such as a eukaryote, prokaryote, mammal, human, yeast, or bacterium, or the sample can be from a virus. The samples can be used without any treatment, or with treatment if desired.

Thus, in the present invention, sample or test sample comprises a target enzyme, as described herein.

3). Mechanism

In the assays provided herein, the shift in $E^0$ can due either the removing a moiety from the vicinity the EAM, or the adding of a moiety to the vicinity of the EAM. The moiety can be any size, as long as the removing or adding of such moiety results in a shift of the $E^0$ of EAM that enable the detection of the target enzyme.

In general, the adding of a moiety to the vicinity of the EAM results in a positive shift in the $E^0$ of the EAM. One example is the kinase assay described herein.

In general, the removing of a moiety to the vicinity of the EAM results in a negative shift in the $E^0$ of the EAM. One example is the "lawnmower assay" described herein.

In some embodiments, an assay may involve both the adding and removing moieties to or from the vicinity of the EAM, thus involve the shift of the $E^0$ of the EAM in both directions. One example is the "lawnmower assay" described herein. See FIG. 4A.

4). Applications

The methods and compositions provide herein find use in different applications.

Kinase

In one aspect, the present invention provides methods for detecting kinase, the method comprises: (a) adding a test sample comprises a kinase to an electrode comprising: (i) a self-assembled monolayer (SAM); (ii) a covalently attached eletroactive active moiety (EAM) comprising a transition metal complex with an $E^0$; and (iii) a plurality of proteins attached to said electrode, wherein said proteins are first substrates of said kinase; (b) phosphorylating said proteins with said kinase and a second kinase substrate; and (c) determining the presence of said kinase by measuring a change of said $E^0$.

In some embodiments, the kinase assay employs a mixed self-assembled monolayer (SAM) of thiolated electroactive moieties (EAM) that are sparsely diluted with neighboring oligopeptide sequences that are known substrates for kinase enzymes. In this arrangement, the EAM is "exposed" to the SAM/solution interface. In the presence of kinase target of interest, the oligopeptide in the SAM will be specifically phosphorylated with a polymer-modified ATP cofactor that is present in the sample matrix resulting in an oligopeptide that is modified with a phosphate-terminated polymer. If the phosphorylation site is near the height of the EAM in the mixed SAM arrangement, the polymer-coupled product peptide will "shield" the neighboring EAMs from solvent. This change in solvation environment of the EAM due to the catalytic phosphorylation of the kinase will result in a change in potential that can be detected electrochemically. A graphical representation of some embodiments of the kinase assay is shown in FIG. 1.

As described herein, protein kinase transfers a phosphate from a donor (the second substrate) to an acceptor peptide (the first substrate). In the present invention, the first and second substrate can be either the capture substrate or the solution substrate.

Once a target kinase is determined and a synthetic peptide substrate identified, the assay can be optimized by changing the dimensions/concentrations of the EAM and peptide components in the SAM.

Once the potential shift is optimized for a particular kinase of interest, the assay can be used to screen for drug candidate that inhibit the kinase activity as described herein.

By "first substrate" herein is meant a protein that is capable of being phosphorylated by a kinase. The composition of first substrate depends on the target kinase.

In some embodiments, the target kinase is protein kinase C (PKC) and the first substrate comprise a peptide has the sequence of SEQ ID NO:1 (SIYRRGSRRWRKL).

In some embodiments, the first substrate is from about 10 to 50 amino acids long, preferably from about 15 to 20 amino acids long.

By "second substrate" herein is meant a molecule that provide a phosphate for the phosphorylation by a kinase. In some embodiments, the second substrate is a polymer comprises an ATP. In some embodiments, the second substrate is a polymer comprises a GTP.

In some embodiment, the second substrate is a polymer-modified ATP cofactor.

In some embodiments, the second substrate has the structure of Formula (I):

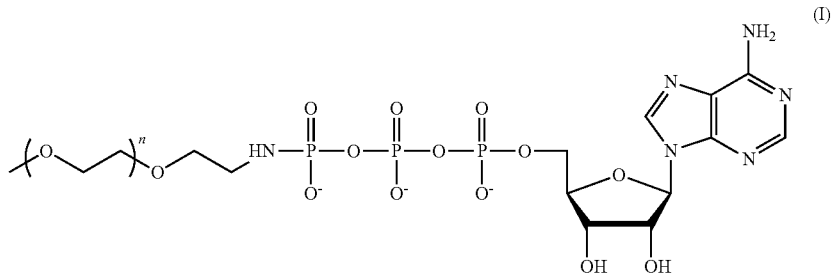

In some embodiment, the EAM and the first substrate peptides are arranged so that the EAM is at least partially exposed to a solution.

Generally, the first substrate comprises a phosphorylation site which site is near the height of the EAM in the mixed SAM arrangement, such that when the second substrate is attached to the first substrate through phosphorylation, the second substrate-coupled first substrate will shield the neighboring EAMs from solution.

The sequence of phosphorylation site depends on the target kinase. For example, a peptide substrate for a serine/threonine kinase has a serine or threonine. Consensus sequences for various protein kinases are known. (Methods in Enzymology 200: 62-81 (1991)). Table 2 shows consensus phosphorylation site motifs for various protein kinases that are suitable for the present invention. An asterisk indicates the phosphorylable residue. An "X" indicates any amino acid.

TABLE 2

| Protein Kinase | Consensus Motifs |
| --- | --- |
| Calmodulin-dependent protein kinase II | XRXXS*/T*; (SEQ ID NO: 7) XRXXS*/T*V (SEQ ID NO: 8) |
| Casein kinase I | S(PO$_3$)XXS*/T* (SEQ ID NO: 9) |
| Casein kinase II | S*/T*XXEX; (SEQ ID NO: 10) S*/T*XXDX (SEQ ID NO: 11) |
| c-AMP-dependent protein kinase | RXS*; (SEQ ID NO: 12) RRXS*; (SEQ ID NO: 13) RXXS*; (SEQ ID NO: 14) KRXXS* (SEQ ID NO: 15) |
| c-GMP-dependent protein kinase | R/KXS*/T*; (SEQ ID NO: 16) R/KXXS*/T*; (SEQ ID NO: 17) R/KR/KXS*/T*; (SEQ ID NO: 18) R/KXXXS*/T*; (SEQ ID NO: 19) S*/T*XR/K (SEQ ID NO: 20) |
| Glycogen synthase kinase-3 | S*XXXS(PO$_3$) (SEQ ID NO: 21) |
| Growth-associated histone H1 kinase (MPF, cdc2$^+$/CDC28 protein kinases) | S*/T*PXK/R; (SEQ ID NO: 22) K/RS*/T*P; (SEQ ID NO: 23) S*/T*PK/R (SEQ ID NO: 24) |
| Phosphorylase kinase | K/RXXS*V/I (SEQ ID NO: 25) |
| Protein kinase C | S*/T*XK/R; (SEQ ID NO: 26) K/RXX S*/T*; (SEQ ID NO: 27) K/RXXS*/T*XK/R; (SEQ ID NO: 28) K/RXS*/T*; (SEQ ID NO: 29) K/RXS*/T*XK/R (SEQ ID NO: 30) |
| Tyrosine kinase/EGF-receptor kinase | XE/DY*X; (SEQ ID NO: 31) XE/DY*I/L/V (SEQ ID. NO: 32) |

The utility of a potential peptide substrate for the kinase assay can be determined by incubating the potential peptide substrate with the kinase under conditions where the kinase is known to be active. Those peptide substrates that are useful in a kinase reaction are those that can be phosphorylated by a kinase of interest. Other preferred peptide substrates are listed in the Examples.

Any kinase recognition motif known in the art can be used in accordance with the present invention. Examples of recognition motifs which can be monitored for phosphorylation using the metal binding amino acids of the present invention are shown in Table 3.

TABLE 3

| Kinase | recognition motif |
| --- | --- |
| Protein kinase C (PKC) | -Ser/Thr-Phe-Arg-Arg-Arg-(SEQ ID NO: 5) |
| cyclic-AMP dependent kinase (PKA) | -Leu-Arg-Arg-Ala-Ser/Thr-Leu-(SEQ ID NO: 6) |
| Abelson kinase (AbI) | -Ile-Tyr-Ala-Ala-Pro-Phe (SEQ ID NO: 7 |

A list of other peptides which can be phosphorylated (and the corresponding kinases) is found in Table I of Pinna & Donella-Deana, Biochemica et Biophysica Acta 1222: 415-431 (1994); incorporated herein by reference in its entirety. Another list can be found at in New England Biolabs Inc. 2005-06 Catalog & Technical Reference, page 198, incorporated herein by reference in its entirety.

Activators can be added to the kinase reaction where desired, e.g., where the kinase under investigation requires an activator. It also may be desirable to add an activator to achieve optimal kinase activity. Activators useful in the kinase reaction include, but are not limited to, calcium, phospholipids and other lipids, and phorbol 12-myristate 13-acetate (PMA) or similar activators for Calcium-phospholipid-dependent protein kinase (PKC), calcium and calmodulin for calmodulin-dependent protein kinase (CaM K), cAMP for cAMP-dependent protein kinase (PKA) holoenzyme, cGMP for cGMP-dependent protein kinase (PKG), DNA for DNA-PK. Activators can be added at nanomolar or higher concentrations and at micromolar or lower concentrations depending on the kinase under investigation. A termination reagent can optionally be added to the system in which the kinase reaction is occurring where an end point is desired, e.g., for measuring and quantitating the activity of protein kinase. The termination reagent usually is a metal chelating reagent added at a concentration that is sufficient to sequester the metal away from the kinase. In addition, any other reagent that terminates the phosphorylation catalyzed by the kinase can be used to terminate the phosphorylation reaction. For example, EDTA, EGTA, and 1,10-phenanthroline are good chelators for magnesium, calcium, and zinc, respectively. Other ion chelating agents may be used. Additionally, kinases can be heat inactivated.

The kinase reaction can also be performed using a phosphopeptide as the phosphate donor and a nucleoside diphosphate (NDP) as the phosphate acceptor, i.e., the reverse of the previously described reaction. In this configuration, the kinase reaction is performed in the same manner as is described above. However, the output that is detected generally will be the inverse of the output for kinase reactions where a phosphopeptide is the phosphate donor. That is, where there is kinase activity in this assay configuration, output will increase when dephosphorylation of the phosphopeptide substrate and phosphorylation of the NDP occur.

Protease and PSA

In some embodiments, the target enzyme is a protease. Proteases represent a broad class of enzymes involved in numerous critical physiological processes and are implicated as diagnostic markers for many disease states, including arthritis, Alzheimer's disease, cancer, and stroke. The development of biosensor platforms for this important class of proteins remains an active area of multidisciplinary research that will facilitate further advances in catalomics, cell biology, drug discovery, and clinical diagnostics.

In some embodiments, the target enzyme is prostate specific antigen (PSA). PSA, also known as kallikrein III, seminin, semenogelase, γ-seminoprotein and P-30 antigen) is a 34 kD glycoprotein manufactured almost exclusively by the prostate gland. PSA is a serine protease (EC 3.4.21.77) enzyme, and is present in small quantities in the serum of normal men, and is often elevated in the presence of prostate cancer and in other prostate disorders. A blood test to measure PSA is the one of the tests currently available for the early detection of prostate cancer. Rising levels of PSA over time are associated with both localized and metastatic prostate cancer (CaP).

On exemplary embodiment is depicted in FIGS. 4A and 4B, and FIGS. 6A and 6B. In this assay, a peptide (HSSKLQC, SEQ ID NO:33) is first attached to a linker. This results in the shift of E$^0$ (a positive shift). When PSA is present in the assay, it cleaves the peptide, results in another shift of E$^0$ (a negative shift).

Peptidase Toxin

In one aspect, the present invention provides compositions and methods for detecting peptidases toxin. The method comprises the steps of: (a) adding a test sample comprising a protease to an electrode, said electrode comprises: (i) a self-assembled monolayer (SAM); (ii) a covalently attached eletroactive active moiety (EAM) comprising a transition metal complex with an E$^0$; and (iii) a plurality of proteins attached to said electrode, wherein said proteins comprises a cleavage site of said protease; (b) cleaving a plurality of said proteins with said protease; and (c) determining the presence of said protease by measuring a change of said $E^o$.

In some embodiments, a substrate of the target peptidase comprises a cleavage site is attached to the electrode. In some embodiments, the substrate comprises a peptide that comprises a cleavage site which can be cleaved by the target peptidase. Preferably, the peptide further comprises an amino acid sequence that can be recognized by the target peptidase (a target recognition sequence), thus confer specificity to the cleaving. The cleavage site and the target recognition sequence can be chosen from those known in the art, such as those described herein, with or without optimization.

In some embodiments, the target peptidase is BoNT A, the substrate comprises residues 187 to 203 of SNAP-25: SNK-TRIDEAN QRATKML (SEQ ID NO:1), or a modified version of it with K189 and K291 substituted with argininies: SNRTRIDEAN QRATRML (SEQ ID NO:2). See Schmidt and Stafford, Applied and Environmental Microbiology, 69:297-303 (2003)

In some embodiments, the target peptidase is BoNT B, the substrate comprises residues 60 to 94 of human VAMP-2 (GenBank Aceesion No: NP_055047): LSELDDRADA LQAGASQFET SAAKLKRKYW WKNLK (SEQ ID NO:3).

In some embodiments, the target peptidase is BoNT F, the substrate comprises residues 37 to 75 of human VAMP-2: AQVDEVVDI MRVNVDKVLE RDQKLSELDD RADALQAGAS (SEQ ID NO:4).

Alternatively, the cleavage site and the target recognition sequence can be designed based on the target peptidase. For example, a library of random peptide can be used to screen for a peptidase substrate.

In some embodiments, the substrate comprise an analogue of a known target peptidase substrate.

The peptide can be made using technique in the art. Peptides can be synthesized chemically. Alternatively, the peptide can be generated by expressing in vitro, such as use *E. coli* or yeast based expression system.

The substrate is attached to the electrode use the attachment linkers as described herein.

Thus, in some embodiments, a test sample comprise the target peptidase is added to an electrode comprises EAM and SAM, and the presence of the target peptidase is determined by measuring the $E^0$ of the EAM, as described herein.

5). Initiation

In one aspect, the present invention provides methods and compositions useful in the detection of target analytes, preferably enzymes.

In some embodiments, the target analyte, contained within a test sample, is added to the electrode containing either a solvent accessible redox active complex or a mixture of solvent accessible redox active molecules and substrates, under conditions that if present, the target enzyme catalyze the substrate. These conditions are generally physiological conditions. Generally a plurality of assay mixtures is run in parallel with different concentrations to obtain a differential response to the various concentrations. Typically, one of these concentrations serves as a negative control, i.e., at zero concentration or below the level of detection. In addition, any variety of other reagents may be included in the screening assay. These include reagents like salts, neutral proteins, e.g. albumin, detergents, etc which may be used to facilitate optimal binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

In some embodiments, upon catalysis of a substrate by the target enzyme, the solvent accessible redox active molecule becomes solvent inhibited. By "solvent inhibited redox active molecule" herein is meant the solvent reorganization energy of the solvent inhibited redox active molecule is less than the solvent reorganization energy of the solvent accessible redox active molecule.

In some embodiments, upon catalysis of a substrate by the target enzyme, the solvent inhibited redox active molecule becomes solvent accessible.

In some embodiments, the required solvent reorganization energy changes sufficiently to result in a change in the $E^0$ of the redox active molecule by at about 100 mV, with at least about 200 mV being preferred, and at least about 300-500 mV being particularly preferred. In some embodiments, when the accessible redox active molecule becomes solvent inhibited, the changes in the $E^0$ of the redox active molecule is a decrease. In some embodiments, when the solvent inhibited redox active molecule becomes solvent accessible, the changes in the $E^0$ of the redox active molecule is a increase.

In some embodiments, the required solvent reorganization energy changes by at least 100 mV, with at least about 200 mV being preferred, and at least about 300-500 mV being particularly preferred.

In some embodiments, the required solvent reorganization energy decreases sufficiently to result in a rate change of electron transfer (kET) between the solvent inhibited redox active molecule and the electrode relative to the rate of electron transfer between the solvent accessible redox active molecule and the electrode. In an embodiment, this rate change is greater than about a factor of 3, with at least about a factor of 10 being preferred and at least about a factor of 100 or more being particularly preferred.

The determination of solvent reorganization energy will be done as is appreciated by those in the art. Briefly, as outlined in Marcus theory, the electron transfer rates (kET) are determined at a number of different driving forces (or free energy, $-\Delta G°$); the point at which the rate equals the free energy is the $\lambda$. This may be treated in most cases as the equivalent of the solvent reorganization energy; see Gray et al. Ann. Rev. Biochem. 65:537 (1996), hereby incorporated by reference.

The solvent inhibited redox active molecule, indicating the presence of a target analyte, is detected by initiating electron transfer and detecting a signal characteristic of electron transfer between the solvent inhibited redox active molecule and the electrode.

Electron transfer is generally initiated electronically, with voltage being preferred. A potential is applied to a sample containing modified nucleic acid probes. Precise control and variations in the applied potential can be via a potentiostat and either a three electrode system (one reference, one sample and one counter electrode) or a two electrode system (one sample and one counter electrode). This allows matching of applied potential to peak electron transfer potential of the system which depends in part on the choice of redox active molecules and in part on the conductive oligomer used.

Preferably, initiation and detection is chosen to maximize the relative difference between the solvent reorganization energies of the solvent accessible and solvent inhibited redox active molecules.

6). Detection

Electron transfer between the redox active molecule and the electrode can be detected in a variety of ways, with electronic detection, including, but not limited to, amperommetry, voltammetry, capacitance and impedance being preferred. These methods include time or frequency dependent methods based on AC or DC currents, pulsed methods, lock-in techniques, and filtering (high pass, low pass, band pass). In some embodiments, all that is required is electron transfer detection; in others, the rate of electron transfer may be determined.

In some embodiments, electronic detection is used, including amperommetry, voltammetry, capacitance, and impedance. Suitable techniques include, but are not limited to, electrogravimetry; coulometry (including controlled potential coulometry and constant current coulometry); voltametry (cyclic voltametry, pulse voltametry (normal pulse voltametry, square wave voltametry, differential pulse voltametry, Osteryoung square wave voltametry, and coulostatic pulse techniques); stripping analysis (aniodic stripping analysis, cathiodic stripping analysis, square wave stripping voltammetry); conductance measurements (electrolytic conductance, direct analysis); time-dependent electrochemical analyses (chronoamperometry, chronopotentiometry, cyclic chronopotentiometry and amperometry, AC polography, chronogalvametry, and chronocoulometry); AC impedance measurement; capacitance measurement; AC voltametry, and photoelectrochemistry.

In some embodiments, monitoring electron transfer is via amperometric detection. This method of detection involves applying a potential (as compared to a separate reference electrode) between the electrode containing the compositions of the invention and an auxiliary (counter) electrode in the test sample. Electron transfer of differing efficiencies is induced in samples in the presence or absence of target analyte.

The device for measuring electron transfer amperometrically involves sensitive current detection and includes a means of controlling the voltage potential, usually a potentiostat. This voltage is optimized with reference to the potential of the redox active molecule.

In some embodiments, alternative electron detection modes are utilized. For example, potentiometric (or voltammetric) measurements involve non-faradaic (no net current flow) processes and are utilized traditionally in pH and other ion detectors. Similar sensors are used to monitor electron transfer between the redox active molecules and the electrode. In addition, other properties of insulators (such as resistance) and of conductors (such as conductivity, impedance and capacitance) could be used to monitor electron transfer between the redox active molecules and the electrode. Finally, any system that generates a current (such as electron transfer) also generates a small magnetic field, which may be monitored in some embodiments.

In some embodiments, the system may be calibrated to determine the amount of solvent accessible redox active molecules on an electrode by running the system in organic solvent prior to the addition of target. This is quite significant to serve as an internal control of the sensor or system. This allows a preliminary measurement, prior to the addition of target, on the same molecules that will be used for detection, rather than rely on a similar but different control system. Thus, the actual molecules that will be used for the detection can be quantified prior to any experiment. Running the system in the absence of water, i.e. in organic solvent such as acetonitrile, will exclude the water and substantially negate any solvent reorganization effects. This will allow a quantification of the actual number of molecules that are on the surface of the electrode. The sample can then be added, an output signal determined, and the ratio of bound/unbound molecules determined. This is a significant advantage over prior methods.

It should be understood that one benefit of the fast rates of electron transfer observed in the compositions of the invention is that time resolution can greatly enhance the signal-to-noise results of monitors based on electronic current. The fast rates of electron transfer of the present invention result both in high signals and stereotyped delays between electron transfer initiation and completion. By amplifying signals of particular delays, such as through the use of pulsed initiation of electron transfer and "lock-in" amplifiers of detection, orders of magnitude improvements in signal-to-noise may be achieved.

Without being bound by theory, it appears that target analytes, bound to an electrode, may respond in a manner similar to a resistor and capacitor in series. Also, the $E^0$ of the redox active molecule can shift as a result of the target analyte binding. Furthermore, it may be possible to distinguish between solvent accessible and solvent inhibited redox active molecules on the basis of the rate of electron transfer, which in turn can be exploited in a number of ways for detection of the target analyte. Thus, as will be appreciated by those in the art, any number of initiation-detection systems can be used in the present invention.

In some embodiments, electron transfer is initiated and detected using direct current (DC) techniques. As noted above, the $E^0$ of the redox active molecule can shift as a result of the change in the solvent reorganization energy upon target analyte binding. Thus, measurements taken at the $E^0$ of the solvent accessible redox active molecule and at the $E^0$ of the solvent inhibited molecule will allow the detection of the analyte. As will be appreciated by those in the art, a number of suitable methods may be used to detect the electron transfer.

In some embodiments, electron transfer is initiated using alternating current (AC) methods. A first input electrical signal is applied to the system, preferably via at least the sample electrode (containing the complexes of the invention) and the counter electrode, to initiate electron transfer between the electrode and the second electron transfer moiety. Three electrode systems may also be used, with the voltage applied to the reference and working electrodes. In this embodiment, the first input signal comprises at least an AC component. The AC component may be of variable amplitude and frequency. Generally, for use in the present methods, the AC amplitude ranges from about 1 mV to about 1.1 V, with from about 10 mV to about 800 mV being preferred, and from about 10 mV to about 500 mV being especially preferred. The AC frequency ranges from about 0.01 Hz to about 10 MHz, with from about 1 Hz to about 1 MHz being preferred, and from about 1 Hz to about 100 kHz being especially preferred In some embodiments, the first input signal comprises a DC component and an AC component. That is, a DC offset voltage between the sample and counter electrodes is swept through the electrochemical potential of the second electron transfer moiety. The sweep is used to identify the DC voltage at which the maximum response of the system is seen. This is generally at or about the electrochemical potential of the redox active molecule. Once this voltage is determined, either a sweep or one or more uniform DC offset voltages may be used. DC offset voltages of from about −1 V to about +1.1 V are preferred, with from about −500 mV to about +800 mV being especially preferred, and from about −300 mV to about 500 mV being particularly preferred. On top of the DC offset voltage, an AC signal component of variable amplitude and frequency is applied. If the redox active molecule has a low enough solvent reorganization energy to respond to the AC perturbation, an AC current will be produced due to electron transfer between the electrode and the redox active molecule.

In some embodiments, the AC amplitude is varied. Without being bound by theory, it appears that increasing the amplitude increases the driving force. Thus, higher amplitudes, which result in higher overpotentials give faster rates of electron transfer. Thus, generally, the same system gives an improved response (i.e. higher output signals) at any single frequency through the use of higher overpotentials at that frequency. Thus, the amplitude may be increased at high frequencies to increase the rate of electron transfer through the system, resulting in greater sensitivity. In addition, as noted above, it may be possible to distinguish between solvent accessible and solvent inhibited redox active molecules on the basis of the rate of electron transfer, which in turn can be used either to distinguish the two on the basis of frequency or overpotential.

In some embodiments, measurements of the system are taken at least two separate amplitudes or overpotentials, with measurements at a plurality of amplitudes being preferred. As noted above, changes in response as a result of changes in amplitude may form the basis of identification, calibration and quantification of the system.

In some embodiments, the AC frequency is varied. At different frequencies, different molecules respond in different ways. As will be appreciated by those in the art, increasing the frequency generally increases the output current. However, when the frequency is greater than the rate at which electrons may travel between the electrode and the redox active molecules, higher frequencies result in a loss or decrease of output signal. At some point, the frequency will be greater than the rate of electron transfer through even solvent inhibited redox active molecules, and then the output signal will also drop.

In addition, the use of AC techniques allows the significant reduction of background signals at any single frequency due to entities other than the covalently attached nucleic acids, i.e. "locking out" or "filtering" unwanted signals. That is, the frequency response of a charge carrier or redox active molecule in solution will be limited by its diffusion coefficient. Accordingly, at high frequencies, a charge carrier may not diffuse rapidly enough to transfer its charge to the electrode, and/or the charge transfer kinetics may not be fast enough. This is particularly significant in embodiments that do not utilize a passivation layer monolayer or have partial or insufficient monolayers, i.e. where the solvent is accessible to the electrode. As outlined above, in DC techniques, the presence of "holes" where the electrode is accessible to the solvent can result in solvent charge carriers "short circuiting" the system. However, using the present AC techniques, one or more frequencies can be chosen that prevent a frequency response of one or more charge carriers in solution, whether or not a monolayer is present. This is particularly significant since many biological fluids such as blood contain significant amounts of redox active molecules which can interfere with amperometric detection methods.

In some embodiments, measurements of the system are taken at least two separate frequencies, with measurements at a plurality of frequencies being preferred. A plurality of frequencies includes a scan. In a preferred embodiment, the frequency response is determined at least two, preferably at least about five, and more preferably at least about ten frequencies.

7). Signal Processing

After transmitting the input signal to initiate electron transfer, an output signal is received or detected. The presence and magnitude of the output signal will depend on the overpotential/amplitude of the input signal; the frequency of the input AC signal; the composition of the intervening medium, i.e. the impedance, between the electron transfer moieties; the DC offset; the environment of the system; and the solvent. At a given input signal, the presence and magnitude of the output signal will depend in general on the solvent reorganization energy required to bring about a change in the oxidation state of the metal ion. Thus, upon transmitting the input signal, comprising an AC component and a DC offset, electrons are transferred between the electrode and the redox active molecule, when the solvent reorganization energy is low enough, the frequency is in range, and the amplitude is sufficient, resulting in an output signal.

In some embodiments, the output signal comprises an AC current. As outlined above, the magnitude of the output current will depend on a number of parameters. By varying these parameters, the system may be optimized in a number of ways.

In general, AC currents generated in the present invention range from about 1 femtoamp to about 1 milliamp, with currents from about 50 femtoamps to about 100 microamps being preferred, and from about 1 picoamp to about 1 microamp being especially preferred.

IV. Apparatus

The present invention further provides apparatus for the detection of analytes using AC detection methods. The apparatus includes a test chamber which has at least a first measuring or sample electrode, and a second measuring or counter electrode. Three electrode systems are also useful. The first and second measuring electrodes are in contact with a test sample receiving region, such that in the presence of a liquid test sample, the two electrodes may be in electrical contact.

In yet another embodiment, the first measuring electrode comprises a redox active complex, covalently attached via a spacer, and preferably via a conductive oligomer, such as are described herein. Alternatively, the first measuring electrode comprises covalently attached redox active molecules and binding ligands.

The apparatus further comprises a voltage source electrically connected to the test chamber; that is, to the measuring electrodes. Preferably, the voltage source is capable of delivering AC and DC voltages, if needed.

In a embodiment, the apparatus further comprises a processor capable of comparing the input signal and the output signal. The processor is coupled to the electrodes and configured to receive an output signal, and thus detect the presence of the target analyte.

V. Applications

In another aspect, the present invention provides methods of screening for protease or kinase inhibitors.

By "inhibitor" herein is meant a molecule that is capable of inhibiting a target enzyme. By "inhibit" herein meant to decrease the activity of the target enzyme, as compared to the activity in the absence of the inhibitor. In this case, "inhibit" is generally at least a 5-20-25% decrease in the activity, with over 50-75% being useful in some embodiments and a 95-98-100% loss of activity being useful as well. The activity of each target enzyme may vary, and is described in more details A. Methods of Screening for BoNT Inhibitors In another aspect, the present invention provides assays for the identification of inhibitors of endopeptidase toxins. In some embodiments the assay is a cell-based assay for identifying peptidase inhibitor. U.S. Patent Publication No. 20050136394, herein is incorporated for its entirety.

B. Methods of Screening for Kinase Inhibitors In one aspect, the present invention provide a kinase assay to screen for kinase inhibitors. Such inhibitors can be used as drug candidates. US. Patent Publication No. 20080113396, herein is incorporated for its entirety.

A further embodiment of the invention is an assay to screen for alterations in or to a kinase reaction. Alterations include, but are not limited to, activations or inhibitions of a kinase reaction. For this, a test substance that is a potential activator or inhibitor of a kinase is added to the assay along with the kinase. An assay typically includes a buffer, a cation, NTP, peptide substrate, and 0.05 units or greater of the kinase of interest.

The potential inhibitor or activator is added to the reaction to determine whether a compound inhibits or stimulates the phosphorylation reaction. In addition, a peptidase is added to the reaction as detailed above. The potential inhibitor or activator can produce a change in the detectable output from the reporter compound. For example, where a potential inhibitor is included in the assay, typically an increase in the detectable output from the reporter compound indicates inhibition of the kinase. This increase would be due to inhibition of the kinase, leading to reduced phosphorylation of the peptide substrate. With fewer amino acids of the peptide substrate phosphorylated, the peptidase can cleave more molecules of the peptide substrates to liberate more reporter compound than a non-inhibited kinase reaction. Conversely, where a potential enhancer is included in the assay, a decrease in output from the reporter compound when compared to a control reaction without the potential enhancer indicates the enhancement of the kinase.

in a preferred embodiment, output from a test sample contacted with a test substance is compared to output of a control sample that has not been contacted with the test substance. Preferably, a ratio is calculated from these detected outputs. The ratio is a measure of the phosphorylation (or lack thereof) of the reporter compound by the kinase.

In some embodiments, a kinase reaction includes a buffer, a source of metal or divalent cation, a nucleotide triphosphate (NTP), which can act as a phosphate donor, a peptide substrate, and, optionally, an activator of the kinase. The buffer, cation, NTP, and peptide substrate are selected based on the protein kinase under investigation, as is explained below. If desired, an activator of the kinase, can also be added. The sample is added to the reaction.

If the sample contains a protein kinase, the protein kinase can catalyze the transfer of the phosphate group from the NTP to phosphorylate the peptide substrate. Kinase reactions can be incubated at a temperature at which the enzyme is active. Preferably, the temperature is about 21° C. or higher. Also preferred is a temperature of 37° C. or lower. Incubation time preferably is 5 seconds or more. Also preferred is an incubation time of one hour or less. However, the incubation time may be longer than one hour, as long as the reaction time is not longer than the transferase remains active under assay conditions. Incubation time may be optimized depending on, e.g., the incubation temperature, the stability and amount of kinase under investigation, and the amount of peptide substrate. The reaction is instantaneous, so measurement can be taken as soon as is practicable.

Buffers useful in a kinase reaction include, but are not limited to, Tris(hydroxymethyl)aminomethane hydrochloride (Tris-HCl), N-(2-Hydroxyethyl)piperazine-N'-(2-ethanesulfonic acid) (HEPES), 4-(2-Hydroxyethyl)piperazine-1-ethanesulfonic acid) (HEPES), 2-(N-Morpholino) ethanesulfonic acid (MES), at concentrations and pH levels that are optimal for the particular enzyme under investigation. Preferably, the buffer concentration is 10 mM or higher. Also preferred is a buffer concentration of 100 mM or lower. The pH of the kinase reaction preferably is 7.0 or higher. Also preferred is a pH of 9.0 or lower.

A preferred divalent cation for the kinase reaction is magnesium. Other divalent cations, such as manganese, calcium, nickel, and the like, can substitute for magnesium. In addition, these other divalent cations can be combined with magnesium. Notably, some of the other divalent cations can be added for optimal activity of the kinase. Preferably, the divalent cation is added at a 1 mM or higher concentration. Also preferred is adding magnesium at a concentration 50 mM or lower concentration. Other divalent cations can be added in the micromolar to millimolar ranges.

The NTP added to the kinase reaction typically is ATP or GTP. As is known in the art, the choice of which NTP is added to the kinase reaction depends on the kinase used in the assay. A preferred concentration of NTP in a kinase reaction is about 1 uM or higher, and is also preferred at 1 mM or lower, and more preferably is 100 uM.

EXAMPLES

Example 1

Synthesis of Compound 1

General Considerations.

All synthetic manipulations (Schemes S1) were performed under a dry argon atmosphere using standard Schlenk techniques, unless otherwise noted. For reaction media, solvents were dried over neutral alumina via the Dow-Grubbs solvent system[1] acquired from Glass Contours (Laguna Beach, Calif.). These solvents were degassed with argon prior to use. All flash chromatography was carried out using silica gel 60 (particle size: 40-63 microns) (EMD Chemicals, Gibbstown, N.J.) under a positive pressure of lab air. $^1$H and $^{13}$C NMR spectra were recorded on a Varian INOVA 500 FT-NMR spectrometer (500 MHz for $^1$H NMR, 125 MHz for $^{13}$C NMR). $^1$H NMR data are reported as follows: chemical shift {multiplicity (b=broad, s=singlet, d=doublet, t=triplet, q=quartet, pt=pseudo triplet from a non-resolved doublet of doublets, and m=multiplet), integration, and peak assignments}. $^1$H and $^{13}$C chemical shifts are reported in ppm downfield from tetramethylsilane (TMS). Matrix-assisted laser desorption ionization time-of-flight (MALDI-TOF) mass spectrometry was obtained on a Perspective Biosystems Voyager DE-Pro mass spectrometer. Elemental analyses were performed by Quantitative Technologies, Inc. (Whitehouse, N.J.). X-ray crystallography was performed on a Bruker SMART 1000 X-ray diffractometer equipped with a CCD detector. Electrochemical experiments were carried out with a CHI model 660A electrochemical analyzer (CHI Instruments Inc.) in a three-electrode system, with a Ag/AgCl reference wire, a platinum wire as counter electrode (Bioanalytical Systems) and evaporated gold substrates as the working electrode. Electrochemical measurements in solution were carried out using a freshly cleaned platinum microdisc electrode (CHI Instruments). Absorbance spectra were collected using an Ocean Optics S200 Dual Channel spectrometer equipped with a DH-2000-BAL light source.

Materials.

Compound 3 and 11-aminoundecanethiol.HCl were synthesized as previously described.[2,3] Chloroform-d$_1$ was purchased from Cambridge Isotope Laboratories. All other reagents were purchased from commercial sources and used without further purification unless otherwise noted. Reactions were monitored by TLC (aluminum backed silica gel sheets 60 $F_{254}$; EMD Chemicals, Inc., Gibbstown, N.J.) and spots were visualized by fluorescence quenching upon exposure to UV light. For the electrochemical measurements, de-ionized water was used after it was passed through an Aqua Solutions system equipped with a combined reverse osmosis deionized system and a UV sterilization lamp, for a final product that has a resistivity of 18.0 MΩ cm.

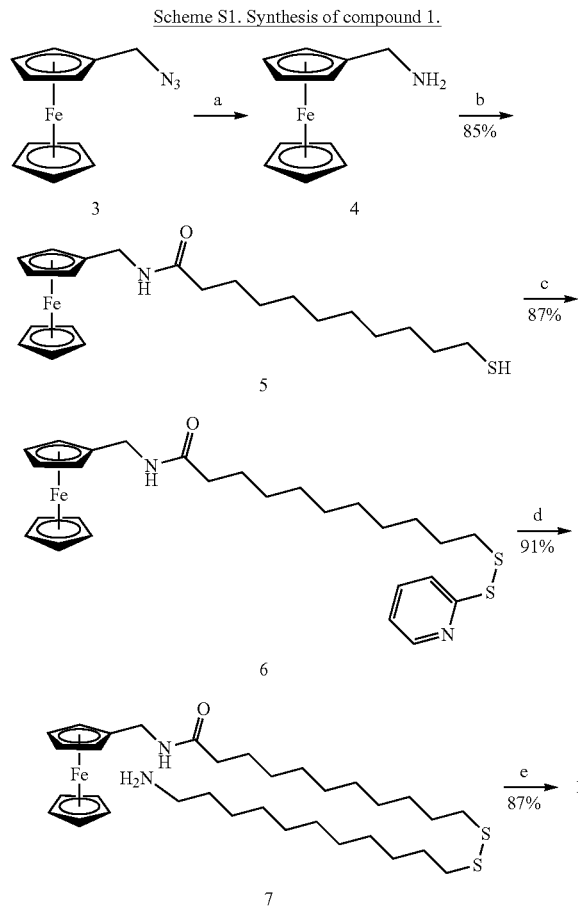

Scheme S1. Synthesis of compound 1.

Reaction Conditions:
(a) $PPh_3/NH_4OH$; (b) DCC, HOBt, 11-mercaptoundecanoic acid; (c) Aldrithiol™-2, TEA; (d) 11-aminoundecanethiol-HCl, DMAP; (e) 3-maleimidobenzoic acid N-hydroxysuccinimide ester, TEA.

Ferrocene Methylamine (4).

Compound 3 (0.226 g, 0.940 mmol) was dissolved in THF (4 mL) and cooled to 4° C. in an ice bath. Lithium aluminum hydride (0.053 mg, 1.40 mmol) was added slowly as a solid and the reaction stirred at 4° C. for 1 h and warmed to r.t. for another 2 h. The reaction was cooled in an ice bath and quenched with sat. $Na_2SO_{4(aq)}$ (5 mL). After 10 min, the mixture was poured into $NaOH_{(aq)}$ (0.1 M, 100 mL) and extracted with DCM (3×50 mL). The organic phase was dried over $Na_2SO_4$, filtered, and concentrated to an orange solid (0.177 g, 0.820 mmol, 87%). $^1H$ NMR consistent with the structure of 4.

11-Mercaptoundecanoic acid ferrocenylmethyl-amide (5). Compound 4 (0.175 g, 0.81 mmol), N,N'-dicyclohexylcarbodiimide (0.169 g, 0.82 mmol), 1-hydroxybenzotriazole (0.126 g, 0.82 mmol), and 11-mercaptoundecanoic acid (0.179 g, 0.82 mmol) were combined in degassed acetone (12 mL). The solution was stirred at r.t. for 18 h under an atmosphere of Ar. The reaction mixture was concentrated in vacuo and dissolved in dichloromethane (100 mL). After washing with water (3×50 mL), the organic phase was dried over $Na_2SO_4$, filtered, and concentrated to a crude residue that was purified by column chromatography on silica gel (2:3, EtOAc:hexanes) to yield the pure product as a pale orange solid (0.288 g, 0.69 mmol, 85%). $^1H$ NMR ($CDCl_3$): δ 1.25-1.38 (m, 13H, $(CH_2)_6$+SH), 1.57-1.66 (m, 4H, $COCH_2CH_2$+$CH_2CH_2SH$) 2.17 (t, $J_{H-H}$=7.8 Hz, 2H, $COCH_2$), 2.51 (psuedo dt, $J_{N-H}$=7.3 Hz, 7.4 Hz, 2H, $CH_2SH$), 4.13-4.15 (m, 4H, $NHCH_2$+ferrocene-H), 4.16 (bs, 5H, ferrocene-H), 4.18 (pt, 2H, ferrocene-H), 5.56 (bs, 1H, NH). $^{13}C\{^1H\}$ NMR ($CDCl_3$): δ 24.9, 26.0, 28.6, 29.2, 29.5, 29.5, 29.6, 29.6, 34.2, 37.0, 39.0, 68.4, 68.5, 68.8, 85.0, 172.6.

11-(Pyridin-2-yldisulfanyl)-undecanoic acid ferrocenylmethyl-amide (6). Compound 5 (0.288 g, 0.69 mmol) was dissolved in methanol (8 mL) and dichloromethane (2 mL). Aldrithiol™-2 (0.304 g, 1.38 mmol) followed by triethylamine (0.192 mL, 1.38 mmol) were added and the reaction set to stir at r.t. for 15 h under an atmosphere of Ar. The solvent was removed in vacuo and the crude residue was purified by column chromatography on silica gel (2:3, EtOAc:hexanes) to yield the pure product as an orange oil (0.316 g, 0.60 mmol, 87%). $^1H$ NMR ($CDCl_3$): δ 1.25-1.39 (m, 12H, $(CH_2)_6$), 1.60-1.71 (m, 4H, $COCH_2CH_2$+$CH_2CH_2SS$), 2.16 (t, $J_{H-H}$=7.8 Hz, 2H, $COCH_2$), 2.79 (t, $J_{H-H}$=7.4 Hz, $CH_2CH_2SS$), 4.13-4.15 (m, 4H, $NHCH_2$+ferrocene-H), 4.16 (bs, 5H, ferrocene-H), 4.18 (pt, 2H, ferrocene-H), 5.59 (bs, 1H, NH), 7.63-7.66 (m, 1H, pyridyl-H), 7.06-7.09 (m, 1H, pyridyl-H), 7.73 (d, 1H, $J_{H-H}$=8.1 Hz, pyridyl-H), 8.45 (d, 1H, $J_{H-H}$=4.8 Hz, pyridyl-H). $^{13}C\{^1H\}$ NMR ($CDCl_3$): δ 26.0, 28.6, 29.1, 29.3, 29.5, 29.5, 29.5, 29.6, 37.0, 39.0, 39.2, 68.4, 68.5, 68.8, 85.0, 119.7, 120.7, 137.1, 149.8, 160.9, 172.6.

11-(11-Amino-undecyldisulfanyl)-undecanoic acid ferrocenylmethyl-amide (7). Compound 6 (0.060 g, 0.11 mmol), 11-aminoundecanethiol-HCl (0.032 g, 0.13 mmol), and 4-dimethylaminopyridine (0.030 g, 0.24 mmol) were combined in THF (4 mL) and DMF (1 mL) for 5 h at r.t. under Ar. The solvent was removed in vacuo and the crude residue was purified by column chromatography on silica gel (0.3:0.7:9, TEA:MeOH:DCM) to yield the pure product as a pale yellow solid (0.065 g, 0.10 mmol, 91%). ESI-MS (MeOH) m/z: 617.77 (M+H)$^+$. $^1H$ NMR consistent with the structure of 7.

3-Maleimido-N-{11-[10-(ferrocenylmethyl-carbamoyl)-decyldisulfanyl]-undecyl}-benzamide (1)

Compound 7 (0.024 g, 0.039 mmol) and 3-maleimidobenzoic acid-N-hydroxysuccinimide ester (0.024 g, 0.078 mmol) were combined in N,N-dimethylacetamide (3 mL). Triethylamine (0.100 mL) was added and the reaction set to stir at r.t. for 4 h under an atmosphere of Ar. The solvent was removed in vacuo and the crude residue was dissolved in dichloromethane (100 mL), washed with $H_2O$ (3×50 mL), dried over $Na_2SO_4$, and concentrated. The crude residue was purified by column chromatography on silica gel (0.1:0.9:9, MeOH:EtOAc:DCM) to yield the pure product as an orange solid (0.028 g, 0.034 mmol, 87%). $^1H$ NMR consistent with the structure of 1.

We claim:

1. A method for detecting for the presence of a protease in a test sample, said method comprising:
   (a) adding a test sample to a solid support comprising an electrode comprising:
      (i) a self-assembled monolayer (SAM);
      (ii) a covalently attached electroactive active moiety (EAM) comprising a transition metal complex with an $E^0$, wherein said EAM comprises a ferrocene; and
      (iii) a plurality of proteins attached to said electrode, wherein said proteins are arranged so that the EAM is at least partially shielded by the proteins from exposure to a solution and comprise a cleavage site of said protease, wherein the cleavage site is near the height of said EAM;
   (b) cleaving a plurality of said proteins with said protease, if said protease is present, such that when the proteins are cleaved at the cleavage site, the EAM is exposed to the solution; and
   (c) determining the presence of said protease by measuring a change of said $E^0$.

2. The method according to claim 1, wherein said protease is an endopeptidase neurotoxin.

3. The method according to claim 2, wherein said endopeptidase neurotoxin is selected from the group consisting of *Clostridium botulinum* A, B or E.

4. The method according to claim 1, wherein said EAM and said proteins are attached separately to said electrode.

5. The method according to claim 1, wherein said solid support comprises an array of electrodes.

6. The method according to claim 1, wherein the proteins are polypeptides, peptides or oligopeptides.

7. The method according to claim 1, wherein the proteins contain non-naturally occurring amino acids, amino acid analogs and/or peptidomimetic structures.

8. A method for detecting for the presence of a protease in a test sample, said method comprising:
   (a) adding a test sample to a solid support comprising an electrode, said electrode comprising:
      (i) a self-assembled monolayer (SAM);
      (ii) a covalently attached electroactive active moiety (EAM) comprising a transition metal complex with an $E^0$, wherein said EAM comprises osmium and at least one cyano ligand; and
(iii) a plurality of proteins attached to said electrode, wherein said proteins are arranged so that the EAM is at least partially shielded by the proteins from exposure to a solution and comprises a cleavage site of said protease, wherein the cleavage site is near the height of said EAM;
(b) cleaving a plurality of said proteins with said protease, if the protease is present, such that when the proteins are cleaved at the cleavage site, the EAM is exposed to the solution; and
(c) determining the presence of said protease by measuring a change of said $E^0$.

9. The method according to claim 8, wherein said protease is an endopeptidase neurotoxin.

10. The method according to claim 9, wherein said endopeptidase neurotoxin is selected from the group consisting of *Clostridium botulinum* A, B or E.

11. The method according to claim 8, wherein said EAM and said proteins are attached separately to said electrode.

12. The method according to claim 8, wherein said solid support comprises an array of electrodes.

13. The method according to claim 8, wherein the proteins are polypeptides, peptides, or oligopeptides.

14. The method according to claim 8, wherein the proteins contain non-naturally occurring amino acids, amino acid analogs and/or peptidomimetic structures.

* * * * *

SEQUENCE LISTING

```
<160> NUMBER OF SEQ ID NOS: 34

<210> SEQ ID NO 1
<211> LENGTH: 17
<212> TYPE: PRT
<213> ORGANISM: Artificial
<220> FEATURE:
<223> OTHER INFORMATION: Residues 187 to 203 of SNAP-25

<400> SEQUENCE: 1

Ser Asn Lys Thr Arg Ile Asp Glu Ala Asn Gln Arg Ala Thr Lys Met
1               5                   10                  15

Leu

<210> SEQ ID NO 2
<211> LENGTH: 17
<212> TYPE: PRT
<213> ORGANISM: Artificial
<220> FEATURE:
<223> OTHER INFORMATION: Residues 187 to 203 of SNAP-25 modified

<400> SEQUENCE: 2

Ser Asn Arg Thr Arg Ile Asp Glu Ala Asn Gln Arg Ala Thr Arg Met
1               5                   10                  15

Leu

<210> SEQ ID NO 3
<211> LENGTH: 35
<212> TYPE: PRT
<213> ORGANISM: Artificial
<220> FEATURE:
<223> OTHER INFORMATION: Residues 60 to 94 of human VAMP-2

<400> SEQUENCE: 3

Leu Ser Glu Leu Asp Asp Arg Ala Asp Ala Leu Gln Ala Gly Ala Ser
1               5                   10                  15

Gln Phe Glu Thr Ser Ala Ala Lys Leu Lys Arg Lys Tyr Trp Trp Lys
            20                  25                  30

Asn Leu Lys
        35

<210> SEQ ID NO 4
<211> LENGTH: 39
<212> TYPE: PRT
<213> ORGANISM: Artificial
<220> FEATURE:
<223> OTHER INFORMATION: Residues 37 to 75 of human VAMP-2

<400> SEQUENCE: 4

Ala Gln Val Asp Glu Val Val Asp Ile Met Arg Val Asn Val Asp Lys
1               5                   10                  15

Val Leu Glu Arg Asp Gln Lys Leu Ser Glu Leu Asp Asp Arg Ala Asp
            20                  25                  30

Ala Leu Gln Ala Gly Ala Ser
        35

<210> SEQ ID NO 5
<211> LENGTH: 5
<212> TYPE: PRT
<213> ORGANISM: Artificial
<220> FEATURE:
<223> OTHER INFORMATION: Protein kinase C (PKC) Recognition Motif

<400> SEQUENCE: 5
```

```
Ser Thr Pro Arg Arg
1               5

<210> SEQ ID NO 6
<211> LENGTH: 7
<212> TYPE: PRT
<213> ORGANISM: Artificial
<220> FEATURE:
<223> OTHER INFORMATION: cyclic-AMP dependent kinase (PKA) Recognition
      Motif

<400> SEQUENCE: 6

Leu Arg Arg Ala Ser Thr Leu
1               5

<210> SEQ ID NO 7
<211> LENGTH: 6
<212> TYPE: PRT
<213> ORGANISM: Artificial
<220> FEATURE:
<223> OTHER INFORMATION: Abelson kinase (Abl) Recognition Motif

<400> SEQUENCE: 7

Ile Tyr Ala Ala Pro Phe
1               5

<210> SEQ ID NO 8
<211> LENGTH: 6
<212> TYPE: PRT
<213> ORGANISM: Artificial
<220> FEATURE:
<223> OTHER INFORMATION: Calmodulin-dependent protein kinase II
      Consensus phosphorylation site motif
<220> FEATURE:
<221> NAME/KEY: misc_feature
<222> LOCATION: (1)..(1)
<223> OTHER INFORMATION: Xaa can be any naturally ocurring amino acid
<220> FEATURE:
<221> NAME/KEY: misc_feature
<222> LOCATION: (3)..(4)
<223> OTHER INFORMATION: Xaa can be any naturally ocurring amino acid

<400> SEQUENCE: 8

Xaa Arg Xaa Xaa Ser Thr
1               5

<210> SEQ ID NO 9
<211> LENGTH: 7
<212> TYPE: PRT
<213> ORGANISM: Artificial
<220> FEATURE:
<223> OTHER INFORMATION: Calmodulin-dependent protein kinase II
      Consensus phosphorylation site motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally ocurring amino acid

<400> SEQUENCE: 9

Xaa Arg Xaa Xaa Ser Thr Val
1               5

<210> SEQ ID NO 10
<211> LENGTH: 5
<212> TYPE: PRT
```

```
<213> ORGANISM: Artificial
<220> FEATURE:
<223> OTHER INFORMATION: Casein kinase I Consensus phosphorylation site
      motif
<220> FEATURE:
<221> NAME/KEY: misc_feature
<222> LOCATION: (2)..(3)
<223> OTHER INFORMATION: Xaa can be any naturally occurring amino acid

<400> SEQUENCE: 10

Ser Xaa Xaa Ser Thr
1               5

<210> SEQ ID NO 11
<211> LENGTH: 6
<212> TYPE: PRT
<213> ORGANISM: Artificial
<220> FEATURE:
<223> OTHER INFORMATION: Casein kinase II Consensus phosphorylation site
      motif
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 11

Ser Thr Xaa Xaa Glu Xaa
1               5

<210> SEQ ID NO 12
<211> LENGTH: 6
<212> TYPE: PRT
<213> ORGANISM: Artificial
<220> FEATURE:
<223> OTHER INFORMATION: Casein kinase II Consensus phosphorylation site
      motif
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 12

Ser Thr Xaa Xaa Asp Xaa
1               5

<210> SEQ ID NO 13
<211> LENGTH: 4
<212> TYPE: PRT
<213> ORGANISM: Artificial
<220> FEATURE:
<223> OTHER INFORMATION: c-AMP-dependent protein kinase Consensus
      phosphorylation site motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 13

Arg Arg Xaa Ser
1

<210> SEQ ID NO 14
<211> LENGTH: 4
```

```
<212> TYPE: PRT
<213> ORGANISM: Artificial
<220> FEATURE:
<223> OTHER INFORMATION: c-AMP-dependent protein kinase Consensus
      phosphorylation site motif
<220> FEATURE:
<221> NAME/KEY: misc_feature
<222> LOCATION: (2)..(3)
<223> OTHER INFORMATION: Xaa can be any naturally occurring amino acid

<400> SEQUENCE: 14

Arg Xaa Xaa Ser
1

<210> SEQ ID NO 15
<211> LENGTH: 5
<212> TYPE: PRT
<213> ORGANISM: Artificial
<220> FEATURE:
<223> OTHER INFORMATION: c-AMP-dependent protein kinase Consensus
      phosphorylation site motif
<220> FEATURE:
<221> NAME/KEY: misc_feature
<222> LOCATION: (3)..(4)
<223> OTHER INFORMATION: Xaa can be any naturally occurring amino acid

<400> SEQUENCE: 15

Lys Arg Xaa Xaa Ser
1               5

<210> SEQ ID NO 16
<211> LENGTH: 5
<212> TYPE: PRT
<213> ORGANISM: Artificial
<220> FEATURE:
<223> OTHER INFORMATION: c-GMP-dependent protein kinase Consensus
      phosphorylation site motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 16

Arg Lys Xaa Ser Thr
1               5

<210> SEQ ID NO 17
<211> LENGTH: 6
<212> TYPE: PRT
<213> ORGANISM: Artificial
<220> FEATURE:
<223> OTHER INFORMATION: c-GMP-dependent protein kinase Consensus
      phosphorylation site motif
<220> FEATURE:
<221> NAME/KEY: misc_feature
<222> LOCATION: (3)..(4)
<223> OTHER INFORMATION: Xaa can be any naturally occurring amino acid

<400> SEQUENCE: 17

Arg Lys Xaa Xaa Ser Thr
1               5

<210> SEQ ID NO 18
<211> LENGTH: 7
<212> TYPE: PRT
<213> ORGANISM: Artificial
<220> FEATURE:
<223> OTHER INFORMATION: c-GMP-dependent protein kinase Consensus
      phosphorylation site motif
<220> FEATURE:
<221> NAME/KEY: misc_feature
```

-continued

```
<222> LOCATION: (5)..(5)
<223> OTHER INFORMATION: Xaa can be any naturally occurring amino acid

<400> SEQUENCE: 18

Arg Lys Arg Lys Xaa Ser Thr
1               5

<210> SEQ ID NO 19
<211> LENGTH: 7
<212> TYPE: PRT
<213> ORGANISM: Artificial
<220> FEATURE:
<223> OTHER INFORMATION: c-GMP-dependent protein kinase Consensus
      phosphorylation site motif
<220> FEATURE:
<221> NAME/KEY: misc_feature
<222> LOCATION: (3)..(5)
<223> OTHER INFORMATION: Xaa can be any naturally occurring amino acid

<400> SEQUENCE: 19

Arg Lys Xaa Xaa Xaa Ser Thr
1               5

<210> SEQ ID NO 20
<211> LENGTH: 5
<212> TYPE: PRT
<213> ORGANISM: Artificial
<220> FEATURE:
<223> OTHER INFORMATION: c-GMP-dependent protein kinase Consensus
      phosphorylation site motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 20

Ser Thr Xaa Arg Lys
1               5

<210> SEQ ID NO 21
<211> LENGTH: 5
<212> TYPE: PRT
<213> ORGANISM: Artificial Sequence
<220> FEATURE:
<223> OTHER INFORMATION: Glycogen synthase kinase-3 Consensus
      phosphorylation site motif
<220> FEATURE:
<221> NAME/KEY: misc_feature
<222> LOCATION: (2)..(4)
<223> OTHER INFORMATION: Xaa can be any naturally occurring amino acid

<400> SEQUENCE: 21

Ser Xaa Xaa Xaa Ser
1               5

<210> SEQ ID NO 22
<211> LENGTH: 6
<212> TYPE: PRT
<213> ORGANISM: Artificial
<220> FEATURE:
<223> OTHER INFORMATION: Growth-associated histone H1 kinase (MPF,
      cdc2+/ CDC28 protein kinases) Consensus phosphorylation site motif
<220> FEATURE:
<221> NAME/KEY: misc_feature
<222> LOCATION: (4)..(4)
<223> OTHER INFORMATION: Xaa can be any naturally occurring amino acid

<400> SEQUENCE: 22

Ser Thr Pro Xaa Lys Arg
1               5
```

```
<210> SEQ ID NO 23
<211> LENGTH: 5
<212> TYPE: PRT
<213> ORGANISM: Artificial
<220> FEATURE:
<223> OTHER INFORMATION: Growth-associated histone H1 kinase (MPF,
      cdc2+/ CDC28 protein kinases) Consensus phosphorylation site motif

<400> SEQUENCE: 23

Lys Arg Ser Thr Pro
1               5

<210> SEQ ID NO 24
<211> LENGTH: 5
<212> TYPE: PRT
<213> ORGANISM: Artificial
<220> FEATURE:
<223> OTHER INFORMATION: Growth-associated histone H1 kinase (MPF,
      cdc2+/ CDC28 protein kinases) Consensus phosphorylation site motif

<400> SEQUENCE: 24

Ser Thr Pro Lys Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Phosphorylase kinase Consensus phosphorylation
      site motif
<220> FEATURE:
<221> NAME/KEY: misc_feature
<222> LOCATION: (3)..(4)
<223> OTHER INFORMATION: Xaa can be any naturally occurring amino acid

<400> SEQUENCE: 25

Lys Arg Xaa Xaa Ser Val Ile
1               5

<210> SEQ ID NO 26
<211> LENGTH: 5
<212> TYPE: PRT
<213> ORGANISM: Artificial Sequence
<220> FEATURE:
<223> OTHER INFORMATION: Protein kinase C Consensus phosphorylation site
      motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 26

Ser Thr Xaa Lys Arg
1               5

<210> SEQ ID NO 27
<211> LENGTH: 6
<212> TYPE: PRT
<213> ORGANISM: Artificial Sequence
<220> FEATURE:
<223> OTHER INFORMATION: Protein kinase C Consensus phosphorylation site
      motif
<220> FEATURE:
<221> NAME/KEY: misc_feature
<222> LOCATION: (3)..(4)
<223> OTHER INFORMATION: Xaa can be any naturally occurring amino acid

<400> SEQUENCE: 27
```

```
Lys Arg Xaa Xaa Ser Thr
1               5

<210> SEQ ID NO 28
<211> LENGTH: 9
<212> TYPE: PRT
<213> ORGANISM: Artificial Sequence
<220> FEATURE:
<223> OTHER INFORMATION: Protein kinase C Consensus phosphorylation site
      motif
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 28

Lys Arg Xaa Xaa Ser Thr Xaa Lys Arg
1               5

<210> SEQ ID NO 29
<211> LENGTH: 5
<212> TYPE: PRT
<213> ORGANISM: Artificial
<220> FEATURE:
<223> OTHER INFORMATION: Protein kinase C Consensus phosphorylation site
      motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 29

Lys Arg Xaa Ser Thr
1               5

<210> SEQ ID NO 30
<211> LENGTH: 8
<212> TYPE: PRT
<213> ORGANISM: Artificial sequence
<220> FEATURE:
<223> OTHER INFORMATION: Protein Kinase C Consensus phosphorylation site
      motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 30

Lys Arg Xaa Ser Thr Xaa Lys Arg
1               5

<210> SEQ ID NO 31
<211> LENGTH: 5
<212> TYPE: PRT
<213> ORGANISM: Artificial sequence
<220> FEATURE:
<223> OTHER INFORMATION: Tyrosine kinase/EGF- receptor kinase Consensus
      phosphorylation site motif
<220> FEATURE:
<221> NAME/KEY: misc_feature
<222> LOCATION: (1)..(1)
<223> OTHER INFORMATION: Xaa can be any naturally occurring amino acid
<220> FEATURE:
```

```
<221> NAME/KEY: misc_feature
<222> LOCATION: (5)..(5)
<223> OTHER INFORMATION: Xaa can be any naturally occurring amino acid

<400> SEQUENCE: 31

Xaa Glu Asp Tyr Xaa
1               5

<210> SEQ ID NO 32
<211> LENGTH: 7
<212> TYPE: PRT
<213> ORGANISM: Artificial
<220> FEATURE:
<223> OTHER INFORMATION: Tyrosine kinase/EGF- receptor kinase Consensus
      phosphorylation site motif
<220> FEATURE:
<221> NAME/KEY: misc_feature
<222> LOCATION: (1)..(1)
<223> OTHER INFORMATION: Xaa can be any naturally occurring amino acid

<400> SEQUENCE: 32

Xaa Glu Asp Tyr Ile Leu Val
1               5

<210> SEQ ID NO 33
<211> LENGTH: 7
<212> TYPE: PRT
<213> ORGANISM: Artificial
<220> FEATURE:
<223> OTHER INFORMATION: PSA substrate peptide

<400> SEQUENCE: 33

His Ser Ser Lys Leu Gln Cys
1               5

<210> SEQ ID NO 34
<211> LENGTH: 13
<212> TYPE: PRT
<213> ORGANISM: Artificial
<220> FEATURE:
<223> OTHER INFORMATION: Protein kinase C substrate peptide

<400> SEQUENCE: 34

Ser Ile Tyr Arg Arg Gly Ser Arg Arg Trp Arg Lys Leu
1               5                   10
```